US010836739B2

(12) United States Patent
Inoue et al.

(10) Patent No.: US 10,836,739 B2
(45) Date of Patent: Nov. 17, 2020

(54) EPOXYCYCLOHEXANE DICARBOXYLIC ACID DIESTER, PLASTICIZER, STABILIZER AND RESIN COMPOSITION

(71) Applicant: New Japan Chemical Co., Ltd., Kyoto (JP)

(72) Inventors: Takahiro Inoue, Kyoto (JP); Taiki Tsuji, Kyoto (JP); Masahiro Morikawa, Kyoto (JP); Minako Tsujimoto, Kyoto (JP); Shoki Yoshichika, Kyoto (JP); Ken-ichi Miyazaki, Kyoto (JP); Yuka Sato, Kyoto (JP)

(73) Assignee: NEW JAPAN CHEMICAL CO., LTD, Kyoto (JP)

( * ) Notice: Subject to any disclaimer, the term of this patent is extended or adjusted under 35 U.S.C. 154(b) by 120 days.

(21) Appl. No.: 15/576,651

(22) PCT Filed: May 25, 2016

(86) PCT No.: PCT/JP2016/065456
§ 371 (c)(1),
(2) Date: Nov. 22, 2017

(87) PCT Pub. No.: WO2016/190354
PCT Pub. Date: Dec. 1, 2016

(65) Prior Publication Data
US 2018/0127390 A1    May 10, 2018

(30) Foreign Application Priority Data

| May 27, 2015 | (JP) | 2015-107693 |
| Jun. 30, 2015 | (JP) | 2015-130534 |
| Jul. 15, 2015 | (JP) | 2015-141136 |
| Aug. 7, 2015 | (JP) | 2015-156987 |
| Feb. 24, 2016 | (JP) | 2016-032560 |
| Mar. 22, 2016 | (JP) | 2016-056500 |
| Mar. 23, 2016 | (JP) | 2016-057876 |

(51) Int. Cl.
| C07D 303/42 | (2006.01) |
| C08K 5/00 | (2006.01) |
| C08K 5/1515 | (2006.01) |
| C08L 27/06 | (2006.01) |
| C07D 301/12 | (2006.01) |

(52) U.S. Cl.
CPC .......... *C07D 303/42* (2013.01); *C08K 5/0016* (2013.01); *C08K 5/1515* (2013.01); *C08L 27/06* (2013.01); *C07D 301/12* (2013.01)

(58) Field of Classification Search
CPC .. C07D 303/42; C07D 301/12; C08K 5/0016; C08K 5/1515; C08L 27/06
See application file for complete search history.

(56) References Cited

U.S. PATENT DOCUMENTS

| 2,963,490 | A | 12/1960 | Rowland et al. |
| 4,207,224 | A | 6/1980 | Randell et al. |
| 6,284,917 | B1 | 9/2001 | Brunner et al. |
| 2010/0256278 | A1 | 10/2010 | Harada et al. |
| 2013/0089728 | A1 | 4/2013 | Kobayashi et al. |
| 2017/0015810 | A1 | 1/2017 | Miyazaki et al. |

FOREIGN PATENT DOCUMENTS

| EP | 0479166 | 4/1992 |
| GB | 796391 | 6/1958 |
| JP | S36-004741 | 5/1961 |
| JP | S47-045096 | 11/1972 |
| JP | S53-099251 | 8/1978 |
| JP | S56-061448 | 5/1981 |
| JP | H02-155941 | 6/1990 |
| JP | H05-170753 | 7/1993 |
| JP | H06-001901 | 1/1994 |
| JP | H08-024329 | 1/1996 |
| JP | H08-176383 | 7/1996 |
| JP | H08-228997 | 9/1996 |
| JP | H08-253642 | 10/1996 |
| JP | H10-176089 | 6/1998 |
| JP | H11-158486 | 6/1999 |
| JP | 2000-226482 | 8/2000 |
| JP | 2001-081259 | 3/2001 |

(Continued)

OTHER PUBLICATIONS

Mukhamedova et al., The Synthesis and Properties of Dialkyl Epoxyhexahydrophthalates, Institute of Organic Chemistry USSR, vol. 1 No. 1, (1962), pp. 67-73 (Year: 1962).*
L A Mukhamedova et al, "The Synthesis and Properties of Dialkyl Epoxyhexahydrophthalates", Institute of Organic Chemistry U.S.S.R., vol. 1, No. 1, Jan. 1, 1962, pp. 67-73.
The European Search Report, dated Oct. 31, 2018, in International Patent Application No. PCT/JP2016 065456.
Japanese Office Action, dated Apr. 23, 2019, in corresponding Japanese Patent Application No. 2015-156987.
Van Cleve, et al., Derivatives of Cyclohexene Oxide as Plasticizers and Stabilizers for Vinyl Chloride Resins, Industrial and Engineering Chemistry, Jun. 1958, pp. 873-876, vol. 50, No. 6.
Japanese Office action, dated Nov. 19, 2019, in corresponding Japanese Patent Application No. 2016-056500.

(Continued)

*Primary Examiner* — Robert D Harlan
(74) *Attorney, Agent, or Firm* — Knobbe Martens Olson & Bear, LLP

(57) ABSTRACT

The purpose of the present invention is to provide a novel compound which is useful as a plasticizer that has improved heat resistance and cold resistance, while having good inherent plasticization performance as a plasticizer, or which is useful as a stabilizer for chlorine-containing resins. The inventors have found that a novel epoxycyclohexane dicarboxylic acid diester having a specific structure, which has an epoxy group in the molecular structure and has improved cold resistance and heat resistance, enables the achievement of the above-described purpose, and have been able to achieve a novel compound that is useful as a plasticizer and as a stabilizer.

19 Claims, No Drawings

(56) References Cited

FOREIGN PATENT DOCUMENTS

| JP | 2001-526252 | | 12/2001 |
|----|-------------|---|---------|
| JP | 2002-194159 | | 7/2002 |
| JP | 2003-165881 | | 6/2003 |
| JP | 2004-107477 | * | 4/2004 |
| JP | 2005-040397 | | 2/2005 |
| JP | 2006-063102 | | 3/2006 |
| JP | 2006-239026 | | 9/2006 |
| JP | 2012-7184 | * | 1/2012 |
| JP | 2012-007184 | | 1/2012 |
| JP | 2013-119622 | | 6/2013 |
| JP | 2013-147520 | | 8/2013 |
| JP | 2015-030773 | | 2/2015 |
| JP | 2015-030774 | | 2/2015 |
| WO | WO 2008/033197 | | 3/2008 |
| WO | WO 2009/069491 | | 6/2009 |
| WO | WO 2012/020618 | | 2/2012 |
| WO | WO 2015/147300 | | 10/2015 |

OTHER PUBLICATIONS

Japanese Office action, dated Nov. 19, 2019, in corresponding Japanese Patent Application No. 2016-057876.
Chinese Office Action, dated Aug. 26, 2020, in corresponding Chinese Patent Application No. 201680030614.1.

* cited by examiner

EPOXYCYCLOHEXANE DICARBOXYLIC ACID DIESTER, PLASTICIZER, STABILIZER AND RESIN COMPOSITION

TECHNICAL FIELD

The present invention relates to a novel epoxycyclohexane dicarboxylic acid diester having an epoxy group in the molecular structure, which is suitable as a plasticizer or as a stabilizer for chlorine-containing resins.

The present invention also relates to a novel plasticizer for vinyl chloride-based resins and a vinyl chloride-based resin composition containing the same. More particularly, the present invention relates to a plasticizer for vinyl chloride-based resins, containing an epoxycyclohexane dicarboxylic acid diester having a specific structure, which has less discoloration and less deterioration in physical properties due to heat and light, good flexibility, and further improved cold resistance and heat resistance, and also relates to a vinyl chloride-based resin composition containing the plasticizer suitable for long-term outdoor use etc.

The present invention further relates to a novel stabilizer for chlorine-containing resins and a stabilized chlorine-containing resin composition containing the same. More particularly, the present invention relates to a stabilizer containing a novel epoxycyclohexane dicarboxylic acid diester for chlorine-containing resins, the stabilizer being excellent in compatibility with a resin and capable of suppressing discoloration and deterioration of physical properties due to heat and light stably over a long period; relates to a chlorine-containing resin composition containing the stabilizer; and further relates to a method for stabilizing a chlorine-containing resin composition by using the stabilizer.

The present invention further relates to a vinyl chloride-based resin composition for automotive interiors, the composition having improved cold resistance and volatility resistance, particularly fogging resistance, and being excellent in light resistance and heat-aging resistance, as well as relates to an automotive interior material containing the resin composition. More specifically, the present invention relates to not only a vinyl chloride-based resin composition for automotive interiors, containing a novel epoxycyclohexane dicarboxylic acid diester having a specific structure, but also an automotive interior material.

The present invention further relates to a medical vinyl chloride-based resin composition and a medical material, which are less susceptible to flexibility deterioration and discoloration after sterilization and disinfection treatment, the composition further having good processability and flexibility as well as improved heat resistance and cold resistance. More specifically, the present invention relates to a medical vinyl chloride-based resin composition containing a plasticizer containing an epoxycyclohexane dicarboxylic acid diester having a specific structure, which has good processability and flexibility as well as improved heat resistance and cold resistance, and also relates to a material for medical use, in particular, a medical vinyl chloride-based resin composition and a medical material suitable for a medical instrument requiring sterilization and disinfection treatment.

BACKGROUND ART

In general, plasticizers are often used for resins and rubbers for the purpose of improving moldability and imparting flexibility. As the plasticizer, various compounds are used depending on the type of resins or rubbers to be treated, and depending on the intended use and purpose thereof. Among them, ester compounds are known as those that are most frequently used. There are aliphatic, alicyclic, or aromatic compounds as such ester compounds, and monoesters, diesters, triesters, tetraesters, polyesters, and the like can be used in a wide variety of types, but at present the most versatile plasticizer is an aromatic diester, and aliphatic diesters, aromatic triesters, tetraesters, and the like are also widely used for applications requiring cold resistance and heat resistance. In recent years, use of alicyclic diesters has also increased from the viewpoint of environmental problems and the like.

Although needless to say that performance required for such a plasticizer is a superiority in compatibility with a target resin, not only plasticization performances such as impartment of flexibility and improvement of processability, which are an essential performance as a plasticizer, but also heat resistance and cold resistance that can withstand the use at high temperatures and withstand the use at low temperatures are required. Recently such demands for heat resistance and cold resistance are becoming stronger. However, with the conventionally known plasticizers, such requirements cannot be sufficiently satisfied at present, and further improvements in heat resistance and cold resistance are required.

On the other hand, most of resins and rubbers are generally used by blending various stabilizers in order to improve heat resistance and light resistance as well as to prevent deterioration during processing at high temperatures. Among these, chlorine-containing resins exhibit excellent performances in moldability and physical properties as well as in flame retardancy due to the inclusion of chlorine, while chlorine is a cause of degradation such as discoloration and deterioration of physical properties due to heat and light. Thus, suppression of such degradation is necessary, and various stabilizers have been investigated so far and have been actually used. For example, representative ones include well-known versatile stabilizers, not limited to those used for chlorine-containing resins, including fatty acid soaps of metals such as calcium, barium, zinc, magnesium, etc. and antioxidants such as phenol-type antioxidants, phosphorus type antioxidants, sulfur-type antioxidants, etc. Particularly, in applications requiring light resistance, there are cases where ultraviolet absorbers and the like are blended. Furthermore, an epoxy compound is known to be effective for inhibiting the above-mentioned degradation due to chlorine, and epoxidized natural oils such as epoxidized soybean oil and the like are widely used. However, in recent years, chlorine-containing resins have been reexamined from the above-mentioned superiority in excellent performances, and development of new stabilizers is awaited because conventionally known stabilizers have not been sufficiently satisfied.

A molded body of a vinyl chloride-based resin is often produced by adding a plasticizer to a vinyl chloride-based resin and molding the soft vinyl chloride-based resin composition.

Various performances such as flexibility, cold resistance, heat resistance, electric characteristics, etc. are required for a molded body (molded article) obtained by molding a soft vinyl chloride-based resin composition containing such a plasticizer. Representative plasticizers for vinyl chloride-based resins are phthalic acid ester-based esters including, for example, di-2-ethylhexyl phthalate (hereinafter referred to as "DOP") and diisononyl phthalate (hereinafter referred to as "DINP"), and these plasticizers are versatilely used.

However, in recent years, when DOP is administered to a rodent in large quantities in the course of attracting attention on safety against chemical substances, toxicity is recognized. Thus, in accordance with the precautionary principle, the use of phthalate ester compounds such as DOP have been restricted in infants as the main protection target in the region of Japan, Europe, and America. Accordingly, non-phthalate ester type plasticizers are desired also in the market in the plasticizer field.

To date, plasticizers such as acetyl tributyl citrate (hereinafter referred to as "ATBC"), di-2-ethylhexyl adipate (hereinafter referred to as "DOA"), and tri-2-ethylhexyl trimellitate (hereinafter referred to as "TOTM") have been developed as a non-phthalate ester plasticizer (Patent Documents 1 to 3). Among these plasticizers, ATBC and DOA have a problem that their heat resistance was largely short in comparison with phthalate ester plasticizers. In addition, TOTM has heat resistance equal to or higher than that of phthalate ester, and is expected as a plasticizer with good heat resistance, which can substitute for phthalate ester plasticizer, but TOTM has a disadvantage of poor flexibility. Therefore, it has not yet been possible to completely replace phthalate ester plasticizers with non-phthalate ester plasticizers.

Under such circumstances, in recent years, an alicyclic dicarboxylic acid diester plasticizer typified by diisononyl 1,2-cyclohexane dicarboxylate (hereinafter referred to as "DINCH") has flexibility, heat resistance, cold resistance, all being close to phthalate ester plasticizers, and has attracted attention as a non-phthalate ester plasticizer with good balance (Patent Document 4).

An epoxycyclohexane dicarboxylic acid diester typified by di-2-ethylhexyl 4,5-epoxycyclohexane-1,2-dicarboxylate (hereinafter referred to as "E-DEHCH"), which is a kind of alicyclic dicarboxylic acid diester, is also known as an advantageous plasticizer that is more excellent in compatibility with a vinyl chloride-based resin, is superior in plasticizing efficiency, i.e., good flexibility, and is further advantageous in view of bleeding property and migration, as compared with a cyclohexane dicarboxylic acid diester such as DINCH not containing an epoxy group. In particular, in applications intended for long-term outdoor use etc., the epoxy group contained in the structure has an effect of scavenging hydrogen chloride generated by decomposition of vinyl chloride-based resin by heat or light. Thus, such epoxycyclohexane dicarboxylic acid diester can be used as a plasticizer capable of suppressing aging caused by heat or light, that is, suppressing deterioration of physical properties and discoloration of the product, singly or in combination with other plasticizers, and is expected as one of non-phthalate ester plasticizers in the future (Patent Document 5).

On the other hand, in recent years, demands for cold resistance and volatility resistance are getting more severe in electric wire coating applications and so on, and there are increased cases that cannot be handled with non-phthalate ester plasticizers such as conventional DINCH and E-DEHCH. Thus, development of a non-phthalic acid ester plasticizer that satisfies the above requirements, that is, improved cold resistance and volatility resistance, has been eagerly awaited.

Chlorine-containing resins such as vinyl chloride-based resins are excellent in mechanical properties and the like, and further have features such as flame retardancy, because of which they are widely used for various purposes, but at the time of molding processing and in use, degradation such as deterioration of physical properties and discoloration as a result of dehydrochlorination reaction mainly due to heat or light easily occurs. Thus, in the chlorine-containing resins, there is a drawback in that it is difficult to obtain stable product quality. It is also pointed out that hydrogen chloride generated during molding process may cause corrosion of equipment or the like.

For this reason, various studies have been made so far to improve the stability of chlorine-containing resins. For example, various stabilizers such as organic acid metal salts, organotin compounds, organophosphite compounds, β-diketone compounds, polyol compounds, epoxy compounds, antioxidants, ultraviolet absorbers, etc. have been proposed for such purpose (Patent Documents 6 and 7). Among them, in the epoxy compounds, the epoxy group in the molecule has a function to scavenge the hydrogen chloride generated in the dehydrochlorination reaction, and as a result, has a function to suppress degradation of the resin such as deterioration of physical properties and discoloration. Since, in the epoxy compound, there is no concern about environmental problems caused by heavy metal compounds such as cadmium compounds or lead compounds to obtain stable effects, epoxy compounds are widely used in combination with an organic acid metal salt and the like (Patent Document 8).

As the epoxy compound, epoxidized natural oils such as epoxidized soybean oil (hereinafter referred to as "ESBO") and epoxidized linseed oil are well known and widely used. However, epoxidized natural oils such as ESBO etc. have drawbacks in compatibility with chlorine-containing resins and also have problems such as bleeding, and thus attempts to improve such drawbacks and solve such problem have been made (Patent Document 9), but sufficiently satisfactory epoxidized natural oils have not yet been obtained. Therefore, an attempt has been made to use a polymer epoxy compound that does not bleed, such as an epoxy resin, in some applications. Although, in the epoxy resin, there is no problem of bleeding, its performance as a stabilizer is not sufficient, because of which its use is limited.

An alicyclic E-DEHCH excellent in compatibility is attracting attention as an epoxy-based stabilizer excellent in compatibility with a resin and free from concerns such as bleeding, migration, and the like. In particular, by adding to a versatile plasticizer composition of an aliphatic polycarboxylic acid ester, an aromatic polycarboxylic acid ester, an alicyclic polycarboxylic acid ester, a polyester, and a polyether, E-DEHCH can be applied to various uses as a stabilizer having a plasticizer effect (Patent Documents 10 and 11).

In applications requiring heat resistance such as volatility resistance which has become increasingly severe in recent years, a method responding to the demand for the heat resistance is widely used by using a plasticizer excellent in heat resistance, such as heat resistant phthalate esters including diisodecyl phthalate (DIDP), diundecyl phthalate (DUP), dialkyl phthalate (C9 to C11) (trade name "PL-200", manufactured by CG Ester Corporation), dialkyl phthalate (C10 to C13) (trade name "VINYCIZER 124", manufactured by Kao Corporation), and ditridecyl phthalate (trade name "VINYCIZER 20", manufactured by Kao Corporation), and trimellitic acid esters such as tri-2-ethylhexyl trimellitate (TOTM), tri-n-octyl trimellitate (trade name "TRIMEX New NSK", manufactured by Kao Corporation), tri-n-alkyl (C8, C10) trimellitate (trade name "TRIMEX N-08", manufactured by Kao Corporation), isononyl trimellitate (trade name "C-9N", manufactured by ADEKA Corporation), and a trimellitic acid triester of a saturated aliphatic alcohol containing 90% or more of a saturated aliphatic alcohol having 9 carbon atoms and having a ratio of 50 to 99% of a linear-chain saturated aliphatic alcohol (trinonyl trimellitate (branched and linear chain), hereinafter referred to as "TL9TM").

Even with the plasticizer composition having excellent heat resistance as described above, the problems such as discoloration peculiar to the chlorine-containing resin as described above are the same, and an improvement in discoloration is demanded.

However, in the conventional alicyclic epoxy compounds such as E-DEHCH, the alicyclic epoxy compound added is a cause of fogging and the like in applications requiring such strict heat resistance as described above, making it impossible to satisfy the requirement of heat resistance. Thus, at present, it has been impossible to blend such an alicyclic epoxy compound.

On the other hand, various interior materials are used in the interior of automobiles to make the drive comfortable. In general, interior materials for automobiles are composed of a skin layer for producing design property such as soft feeling and luxury feeling and a base material layer for maintaining the structure. Furthermore, in order to give a softer feeling to the skin layer, a foamed layer such as urethane is often used after being lined.

As the skin layer, a polyvinyl chloride-based resin and a polyolefin foam such as a thermoplastic elastomer and a polyethylene are used. Among them, the polyvinyl chloride-based resin is widely used because it can give various tactile sensations from semi-hard one to soft one depending on the blending amount of a plasticizer and because it is excellent in designing property based on easiness of its molding processability.

Commonly used plasticizers for vinyl chloride-based resins can be used as the above plasticizer, and phthalate ester plasticizers typified by relatively inexpensive DINP and DIDP have been most versatilely used. Further, in some members, in order to prevent degradation at high temperatures such asunder the blazing sun, as well as in order to maintain the flexibility at low temperatures in a cold district, a trimellitic acid ester plasticizer (e.g. TOTM, etc.) and an aliphatic dibasic acid ester plasticizer (e.g. DOA, etc.) have also been used. However, in the case of DOA, its cold resistance and flexibility are excellent, but its heat resistance is poor. In the case of TOTM, its heat resistance is excellent, but its cold resistance and flexibility cannot be satisfactory, and TOTM was often used in combination with a phthalate ester plasticizer.

When DOP is administered to a rodent in large quantities under the circumstances where safety against chemical substances attracts attention in recent years, toxicity is observed. Thus, in areas of Japan, Europe, and America, there is a tendency to replace phthalate ester plasticizers such as DOP etc. with another plasticizer, that is, with a non-phthalate ester plasticizer, as part of precautionary measures, and a non-phthalate ester plasticizer which can be substituted for automotive interior materials is desired. In general, ATBC, DINCH and the like in addition to DOA and TOTM are known as the non-phthalate ester plasticizer, but none of them has sufficient performance in view of heat resistance and the like.

As a recent trend, demands for weight reduction and durability are becoming increasingly severe for all automobile parts, and it is strongly desired to improve performances of individual members such as automotive interior materials. Specifically, problems such as deterioration due to heat and light under the blazing sun, that is, deterioration of performances due to volatilization of plasticizers and other additives, and deterioration of physical properties and discoloration due to heat and light peculiar to vinyl chloride-based resins are serious problems. In addition, cloud of windshields etc. due to volatile components, i.e., fogging, is also an important issue. Destruction due to reduced flexibility in a cold district is also a major problem, and cold resistance is an important performance, too.

Up to now, improving only cold resistance or only heat resistance can be done by using, for example, the above-mentioned aliphatic dibasic ester plasticizer or trimellitate ester plasticizer, but it is currently difficult to satisfy both performances at the same time.

It is said that deterioration due to heat and light peculiar to the vinyl chloride-based resin is attributable to hydrogen chloride generated by decomposition in the molecule, in particular, it is known that such deterioration remarkably appears frequently in an interior skin where a lined urethane foam material is used, which is a serious problem when using a vinyl chloride-based resin for the skin of automotive interior materials (Patent Documents 12 and 13). Therefore, various stabilizers have been investigated so far, but one of them, an epoxy-based compound, is very effective as a scavenger for hydrogen chloride, and such an epoxy compound is known to prevent the deterioration of the product itself. As the epoxy compound, epoxidized vegetable oils such as ESBO and epoxidized linseed oil are well known (Patent Documents 11 and 14). However, in the case of the epoxidized vegetable oil, there is a problem in compatibility with a vinyl chloride-based resin, and when mixing is insufficient, the epoxidized vegetable oil becomes non-uniform in the resin, resulting in failure to obtain sufficient performances, and also causes problems such as bleeding. Thus, improvement of such problems was desired.

On the other hand, the vinyl chloride-based resin composition has good processability as well as excellent chemical resistance and durability, and can be adjusted to various hardness by blending a plasticizer. For example, a soft vinyl chloride-based resin material blended with several tens of parts of a plasticizer is superior in kink resistance as compared with polyolefin and the like and can be widely used as medical materials such as medical tubes (e.g. catheters, etc.) and medical bags (e.g. blood bags, infusion bags, etc.). In addition, a semi-hard vinyl chloride-based resin material containing a small amount of a plasticizer is widely used as a medical material such as a connecting member, a branch valve, and a speed adjusting component, which are used in connection with the soft vinyl chloride material.

In addition to the above performances, for example, soft vinyl chloride-based resin materials used for medical materials are required to have good flexibility, excellent heat resistance to withstand heat treatment, and excellent cold resistance to withstand cold storage. Further, from the viewpoint of durability and safety, it is also necessary that dissolution property and migration property of additives be small, so that selection of the plasticizer blended in the largest amount becomes very important. Similarly, in the case of a semi-hard vinyl chloride-based resin composition material, it is necessary to have a hardness that shows appropriate followability, and it is important that heat resistance and cold resistance as well as durability is excellent as with a soft material.

As the plasticizer, phthalate ester plasticizers typified by DOP and DINP have been versatilely used (Patent Document 15). However, with the phthalate ester plasticizer, it is difficult to obtain sufficient heat resistance at the time of heat treatment and the like, and improvement in dissolution property and migration property is also required. Therefore, studies using a trimellitate ester plasticizer (e.g. TOTM, etc.) and a polyester plasticizer are also in progress (Patent Documents 16 and 17).

However, in the case of a medical material using a trimellitate ester plasticizer or a polyester plasticizer, although such a plasticizer is excellent in heat resistance, its processability is inferior and furthermore its plasticization efficiency and cold resistance are not necessarily satisfactory performances. In particular, in order to obtain sufficient flexibility and cold resistance in a soft material, it is necessary to blend a large amount of a plasticizer, and as a result, there is a concern that problems may arise in terms of safety and the like.

In addition, cyclohexane dicarboxylate ester plasticizers typified by DINCH are attracting attention as a non-phthalate ester plasticizer (Patent Document 18).

However, DINCH and the like have problems in heat resistance, particularly discoloration property upon heating, and furthermore, processability was not necessarily satisfactory. Accordingly, development of a plasticizer suitable for a vinyl chloride-based resin composition excellent in processability, the plasticizer being able to provide a medical material having good flexibility and excellent heat resistance and cold resistance, as well as a plasticizer suitable for materials and resin compositions having such performances are awaited.

In the case of medical materials, it is also necessary to perform sterilization and disinfection treatment before use in many applications in consideration of hygiene. Examples of such treatment method include heat treatment such as dry heating, boiling, and pressurized hot water treatment; irradiation with ultraviolet light or radiation; chemical treatment with ethylene oxide gas; and the like. When chemical treatment is performed, there is a concern that toxic ethylene oxide gas may remain, so that heat treatment or irradiation with ultraviolet rays or radiation is mainly used.

In recent years, due to an increase in medical accidents at hospitals and the like, thorough hygiene control in a medical site is becoming stricter, and conditions for sterilization and disinfection treatment are also becoming more severe. However, as such conditions become severe, for example, in the case of heat treatment, deterioration of flexibility due to volatilization of the plasticizer or the like causes destruction of the material, and it is getting impossible for DOP and DINCH to meet the requirements. Also, even in the treatment by irradiation with ultraviolet rays or radiation, deterioration in the discrimination of contents due to discoloration causes a medical accident, which is a big problem, and improvement in this respect is desired. As a method of suppressing the discoloration, for example, it is known that such discoloration can be improved by blending a large amount of a stabilizer (Patent Document 19). However, formulation of a large amount of a stabilizer is problematic in terms of safety and the like, and such a formulation is impossible in practice. At present, it is not yet possible to find an effective improvement method.

As one of the stabilizers, an epoxy compound is known to be effective as a stabilizer having no problem in terms of safety and prevents deterioration such as discoloration. As the epoxy compound, epoxidized vegetable oils (e.g. ESBO, epoxidized linseed oil, etc.) are well known specifically (Patent Documents 20 and 21). However, in the case of the epoxidized vegetable oil, there is a problem in compatibility with a vinyl chloride-based resin, and when mixing is insufficient, such an epoxidized vegetable oil becomes non-uniform in the resin, resulting in failure to obtain sufficient performances and also causes problems such as bleeding. Thus, it is currently difficult to use the epoxidized vegetable oil for medical materials for which particularly severe safety is demanded.

Recently, an alicyclic E-DEHCH that is excellent in compatibility has been attracting attention as an epoxy compound having excellent compatibility with a resin and little bleeding and migration, and it has also been reported that such E-DEHCH exhibits, as a medical material, an excellent effect of suppressing deterioration during treatment by irradiation with ultraviolet rays and by radiation, particularly an excellent effect of suppressing discoloration (Patent Document 22).

PRIOR ART DOCUMENT

Patent Documents

Patent Document 1: JP-A-2000-226482
Patent Document 2: JP-A-2002-194159
Patent Document 3: JP-A-2013-147520
Patent Document 4: JP-A-2001-526252
Patent Document 5: JP-A-2001-081259
Patent Document 6: JP-A-H2-155941
Patent Document 7: WO2009/069491
Patent Document 8: JP-A-H11-158486
Patent Document 9: JP-A-2013-119622
Patent Document 10: JP-B-S36-4741
Patent Document 11: JP-A-H8-253642
Patent Document 12: WO2008/033197
Patent Document 13: WO2012/020618
Patent Document 14: JP-A-H6-1901
Patent Document 15: JP-A-H10-176089
Patent Document 16: JP-A-2003-165881
Patent Document 17: JP-A-2006-239026
Patent Document 18: JP-A-2005-40397
Patent Document 19: JP-A-H8-24329
Patent Document 20: JP-A-H8-176383
Patent Document 21: JP-A-S56-61448
Patent Document 22: JP-A-2015-30773

SUMMARY OF THE INVENTION

Problems to be Solved by the Invention

An object of the first embodiment of the present invention is, in view of the above-described circumstances, to provide a novel useful compound as a plasticizer that is inherently excellent in plasticizing performance and has improved heat resistance and cold resistance and as a stabilizer for chlorine-containing resins.

An object of the second embodiment of the present invention is to provide a plasticizer for vinyl chloride-based resins containing a novel epoxycyclohexane dicarboxylic acid diester capable of solving the above problems, that is, satisfying stricter requirements for cold resistance and volatility resistance and having better flexibility, and also to provide a vinyl chloride-based resin composition containing the plasticizer.

An object of the third embodiment of the present invention is to provide a stabilizer for chlorine-containing resins, the stabilizer being capable of solving the above problems, that is, being environmentally safe and capable of obtaining a stable effect, and more specifically, an object of the third embodiment of the present invention is to provide a stabilizer for chlorine-containing resins, the stabilizer being excellent in the effect as a stabilizer, having good compatibility with a resin, and having improved volatility resistance.

An object of the fourth embodiment of the present invention is, in view of the above-described circumstances, to provide a vinyl chloride-based resin composition for automotive interior materials, which has an improved cold resistance, an improved volatility resistance, especially an improved fogging resistance and is excellent in light resistance and heat-aging resistance, wherein the resin composition contains a plasticizer or a stabilizer for automotive interior materials, the plasticizer or stabilizer being excellent in compatibility with a resin and easy to mix with a resin as well as having improved cold resistance, improved volatile resistance, especially improved fogging resistance; and also to provide an automotive interior material containing the resin composition.

An object of the fifth embodiment of the present invention is to provide a vinyl chloride-based resin composition for medical use and a medical material, capable of solving the above-mentioned problems, that is, having little deterioration such as discoloration after sterilization and disinfection treatment, having good processability and flexibility, and having improved heat resistance and improved cold resistance.

Means for Solving the Problems

In order to solve the above problems, the present inventors focused attention on the alicyclic diesters and the epoxy compounds and conducted intensive studies thereon. As a result, they have found that a novel epoxycyclohexane dicarboxylic acid diester having a specific structure with an epoxy group in the molecular structure satisfies such purpose, and have completed the first embodiment of the present invention.

That is, the epoxycyclohexane dicarboxylic acid diester having a specific structure with an epoxy group in the molecular structure according to the first embodiment of the present invention is characterized by having the chemical structure shown below.

[Item 1] An epoxycyclohexane dicarboxylic acid diester comprising a 4,5-epoxycyclohexane-1,2-dicarboxylic acid diester represented by the following general formula (1), wherein the ratio (molar ratio) of the linear-chain alkyl group with respect to the total amount of the alkyl groups constituting the dicarboxylic acid diester is 50 to 99%:

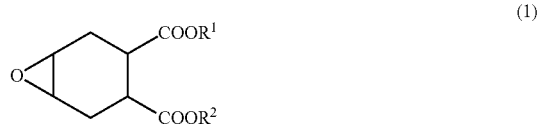

(1)

wherein $R^1$ and $R^2$ are the same or different and each represents a linear or branched-chain alkyl group having 7 to 13 carbon atoms.

[Item 2] The epoxycyclohexane dicarboxylic acid diester according to [item 1], wherein the alkyl group has 8 to 12 carbon atoms.

[Item 3] The epoxycyclohexane dicarboxylic acid diester according to [item 1] or [item 2], wherein the alkyl group is mainly composed of an alkyl group having 9 to 11 carbon atoms, in which the ratio (molar ratio) of alkyl group having 9 carbon atoms/alkyl group having 10 carbon atoms/alkyl group having 11 carbon atoms is in the range of 10 to 25/35 to 50/30 to 45.

[Item 4] The epoxycyclohexane dicarboxylic acid diester according to [item 1] or [item 2], wherein the alkyl group contains an alkyl group having 9 carbon atoms in an amount of 90% or more (molar ratio).

[Item 5] The epoxycyclohexane dicarboxylic acid diester according to any one of [item 1] to [item 4], wherein the ratio (molar ratio) of the linear-chain alkyl group in the alkyl groups is 55 to 95%.

[Item 6] The epoxycyclohexane dicarboxylic acid diester according to any one of [item 1] to [item 4], wherein the ratio (molar ratio) of the linear-chain alkyl group in the alkyl groups is 60 to 95%.

[Item 7] The epoxycyclohexane dicarboxylic acid diester according to any one of [item 1] to [item 4], wherein the ratio (molar ratio) of the linear-chain alkyl group in the alkyl groups is 70 to 95%.

[Item 8] The epoxycyclohexane dicarboxylic acid diester according to anyone of [item 1] to [item 7], wherein the isomer ratio (cis-form/trans form, molar ratio) of the oxirane ring and the alkyloxycarbonyl group via the cyclohexane ring measured by proton nuclear magnetic resonance spectroscopy is 5/95 to 35/65.

[Item 9] The epoxycyclohexane dicarboxylic acid diester according to [item 8], wherein the isomer ratio is 10/90 to 30/70.

[Item 10] The epoxycyclohexane dicarboxylic acid diester according to [item 8], wherein the isomer ratio is 15/85 to 25/75.

[Item 11] The epoxycyclohexane dicarboxylic acid diester according to any one of [item 1] to [item 10] used in a plasticizer.

[Item 12] The epoxycyclohexane dicarboxylic acid diester according to any one of [item 1] to [item 10] used in a stabilizer of a chlorine-containing resin.

[Item 13] A chlorine-containing resin composition comprising the epoxycyclohexane dicarboxylic acid diester according to any one of [item 1] to [item 12].

[Item 14] The chlorine-containing resin composition according to [item 13], wherein the chlorine-containing resin is a vinyl chloride-based resin.

As a result of intensive studies in order to solve the above problems in view of such current situation, the present inventors have found that an epoxycyclohexane dicarboxylic acid diester having a specific structure is excellent in compatibility with a resin, which is a characteristic of the present invention, that is, they have found that cold resistance and volatility resistance of the dicarboxylic acid diester can be improved without impairing the plasticizing efficiency and flexibility. Thus, the second embodiment of the present invention has been completed based on these findings.

Namely, the second embodiment of the present invention provides the following novel plasticizer for vinyl chloride-based resins and a vinyl chloride-based resin composition containing the same.

[Item 1] A plasticizer for vinyl chloride-based resins comprising a 4,5-epoxycyclohexane-1,2-dicarboxylic acid diester represented by the following general formula (1), wherein the ratio (molar ratio) of the linear-chain alkyl group with respect to the total amount of the alkyl groups constituting the dicarboxylic acid diester is 50 to 99%:

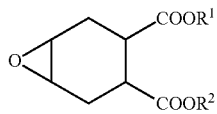

wherein $R^1$ and $R^2$ are the same or different and each represents a linear or branched-chain alkyl group having 7 to 13 carbon atoms.

[Item 2] The plasticizer for vinyl chloride-based resins according to [item 1], wherein the alkyl group has 8 to 12 carbon atoms.

[Item 3] The plasticizer for vinyl chloride-based resins according to [item 1] or [item 2], wherein the alkyl group is mainly composed of an alkyl group having 9 to 11 carbon atoms, in which the ratio (molar ratio) of alkyl group having 9 carbon atoms/alkyl group having 10 carbon atoms/alkyl group having 11 carbon atoms is in the range of 10 to 25/35 to 50/30 to 45.

[Item 4] The plasticizer for vinyl chloride-based resins according to [item 1] or [item 2], wherein the alkyl group contains an alkyl group having 9 carbon atoms in an amount of 90% or more (molar ratio).

[Item 5] The plasticizer for vinyl chloride-based resins according to any one of [item 1] to [item 4], wherein the ratio of the linear-chain alkyl group in the alkyl groups is 55 to 95%.

[Item 6] The plasticizer for vinyl chloride-based resins according to any one of [item 1] to [item 4], wherein the ratio of the linear-chain alkyl group in the alkyl groups is 60 to 95%.

[Item 7] The plasticizer for vinyl chloride-based resins according to any one of [item 1] to [item 4], wherein the ratio of the linear-chain alkyl group in the alkyl groups is 70 to 95%.

[Item 8] The plasticizer for vinyl chloride-based resins according to any one of [item 1] to [item 7], wherein the 4,5-epoxycyclohexane-1,2-dicarboxylic acid diester is obtained by epoxidation reaction of a 4-cyclohexene-1,2-dicarboxylic acid diester.

[Item 9] The plasticizer for vinyl chloride-based resins according to [item 8], wherein the 4-cyclohexene-1,2-dicarboxylic acid diester is obtained by esterification reaction of 4-cyclohexene-1,2-dicarboxylic acid or an acid anhydride thereof with a saturated aliphatic alcohol having 7 to 13 carbon atoms, and wherein the saturated aliphatic alcohol contains a saturated aliphatic alcohol having 9 to 11 carbon atoms as a main component and the linear chain ratio (molar ratio) of the saturated aliphatic alcohol is 50 to 95%.

[Item 10] A vinyl chloride-based resin composition comprising a vinyl chloride-based resin and the plasticizer for vinyl chloride-based resins according to any one of [item 1] to [item 9].

[Item 11] The vinyl chloride-based resin composition according to [item 10], wherein the content of the plasticizer for vinyl chloride-based resins is 1 to 200 parts by weight with respect to 100 parts by weight of the vinyl chloride-based resin.

[Item 12] The vinyl chloride-based resin composition according to [item 10], wherein the content of the plasticizer for vinyl chloride-based resins is 20 to 200 parts by weight with respect to 100 parts by weight of the vinyl chloride-based resin, and the vinyl chloride-based resin composition is a soft vinyl chloride-based resin composition.

[Item 13] The vinyl chloride-based resin composition according to [item 12], wherein the content of the plasticizer for vinyl chloride-based resins is 30 to 150 parts by weight with respect to 100 parts by weight of the vinyl chloride-based resin.

[Item 14] A vinyl chloride-based molded body obtained from the vinyl chloride-based resin composition according to any one of [item 10] to [item 13].

The present inventors focused on the superiority of the epoxy compound as a stabilizer, and as a result of intensive investigation toward development of an epoxy type stabilizer which exhibits the effect as a stabilizer even in a small amount so as to cope with stringent demands of recent years and does not cause problems such as volatility even if the blending amount is much more increased, the inventors have found that an epoxycyclohexane dicarboxylic acid diester having a specific structure is effective as a stabilizer excellent in compatibility with a resin and in volatility resistance. The third embodiment of the present invention has been completed based on these findings.

That is, the third embodiment of the present invention relates to a stabilizer for chlorine-containing resins, containing a novel epoxycyclohexane dicarboxylic acid diester having the following specific structure, as well as a stabilized chlorine-containing resin composition containing the stabilizer and a method for stabilizing a chlorine-containing resin composition.

[Item 1] A stabilizer for chlorine-containing resins comprising a 4,5-epoxycyclohexane-1,2-dicarboxylic acid diester represented by the following general formula (1), wherein the ratio (molar ratio) of the linear-chain alkyl group with respect to the total amount of the alkyl groups constituting the dicarboxylic acid diester is 50 to 99%:

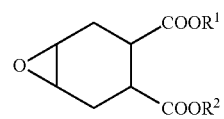

wherein $R^1$ and $R^2$ are the same or different and each represents a linear or branched-chain alkyl group having 7 to 13 carbon atoms.

[Item 2] The stabilizer for chlorine-containing resins according to [item 1], wherein the alkyl group has 8 to 12 carbon atoms.

[Item 3] The stabilizer for chlorine-containing resins according to [item 1] or [item 2], wherein the alkyl group is mainly composed of an alkyl group having 9 to 11 carbon atoms, in which the ratio (molar ratio) of alkyl group having 9 carbon atoms/alkyl group having 10 carbon atoms/alkyl group having 11 carbon atoms is in the range of 10 to 25/35 to 50/30 to 45.

[Item 4] The stabilizer for chlorine-containing resins according to [item 1] or [item 2], wherein the alkyl group contains an alkyl group having 9 carbon atoms in an amount of 90% or more (molar ratio).

[Item 5] The stabilizer for chlorine-containing resins according to any one of [item 1] to [item 4], wherein the ratio of the linear-chain alkyl group in the alkyl groups is 55 to 95%.

[Item 6] The stabilizer for chlorine-containing resins according to any one of [item 1] to [item 4], wherein the ratio of the linear-chain alkyl group in the alkyl groups is 60 to 95%.

[Item 7] The stabilizer for chlorine-containing resins according to any one of [item 1] to [item 4], wherein the ratio of the linear-chain alkyl group in the alkyl groups is 70 to 95%.

[Item 8] The stabilizer for chlorine-containing resins according to any one of [item 1] to [item 7], wherein the 4,5-epoxycyclohexane-1,2-dicarboxylic acid diester is obtained by epoxidation reaction of a 4-cyclohexene-1,2-dicarboxylic acid diester.

[Item 9] The stabilizer for chlorine-containing resins according to [item 8], wherein the 4-cyclohexene-1,2-dicarboxylic acid diester is obtained by esterification reaction of 4-cyclohexene-1,2-dicarboxylic acid or an acid anhydride thereof with a saturated aliphatic alcohol having 7 to 13 carbon atoms, and wherein the saturated aliphatic alcohol contains a saturated aliphatic alcohol having 9 to 11 carbon atoms as a main component and the linear chain ratio (molar ratio) of the saturated aliphatic alcohol is 50 to 99%.

[Item 10] A stabilized chlorine-containing resin composition comprising a chlorine-containing resin and the stabilizer according to any one of [item 1] to [item 9].

[Item 11] The chlorine-containing resin composition according to [item 10], wherein the content of the stabilizer is 1 to 30 parts by weight with respect to 100 parts by weight of the chlorine-containing resin.

[Item 12] The chlorine-containing resin composition according to [item 10], wherein the content of the stabilizer is 1 parts by weight or more and less than 20 parts by weight with respect to 100 parts by weight of the chlorine-containing resin.

[Item 13] The chlorine-containing resin composition according to [item 10], wherein the content of the stabilizer is 5 parts by weight or more and less than 20 parts by weight with respect to 100 parts by weight of the chlorine-containing resin.

[Item 14] The chlorine-containing resin composition according to any one of [item 11] to [item 13], wherein the chlorine-containing resin is a vinyl chloride-based resin.

[Item 15] The chlorine-containing resin composition according to any one of [item 11] to [item 14], further comprising a plasticizer.

[Item 16] The chlorine-containing resin composition according to [item 15], wherein the content of the plasticizer is 5 to 150 parts by weight with respect to 100 parts by weight of the chlorine-containing resin.

[Item 17] The chlorine-containing resin composition according to [item 15] or [item 16], wherein the plasticizer is one or two or more kinds selected from the group consisting of an aliphatic polycarboxylic acid ester, an aromatic polycarboxylic acid ester, an alicyclic polycarboxylic acid ester, a polyester, and a polyether.

[Item 18] The chlorine-containing resin composition according to [item 15] or [item 16], wherein the plasticizer is one or two or more kinds selected from the group consisting of a phthalic acid ester, a trimellitic acid ester, and a cyclohexane dicarboxylic acid ester.

[Item 19] The chlorine-containing resin composition according to [item 15] or [item 16], wherein the plasticizer is one or two or more kinds selected from the group consisting of diisodecyl phthalate (DIDP), di(2-propylheptyl) phthalate (DPHP), diundecyl phthalate (DUP), dialkyl (C9 to C11) phthalate (PL-200), dialkyl(C10 to C13) phthalate (VINYCIZER 124), ditridecyl phthalate (VINYCIZER 20), tri-n-alkyl(C8, C10) trimellitate (TRIMEX N-08), tri-n-octyl trimellitate (TRIMEX New NSK), isononyl trimellitate (C-9N), and a trimellitic acid triester of a saturated aliphatic alcohol containing 90% or more of a saturated aliphatic alcohol having 9 carbon atoms wherein the ratio of the linear-chain saturated aliphatic alcohol is from 50 to 99% (trinonyl trimellitate (branched and linear chain), TL9TM).

[Item 20] The chlorine-containing resin composition according to anyone of [item 15] to [item 19], which is obtained by a method in which the stabilizer for chlorine-containing resins and a plasticizer are previously mixed and then added to a chlorine-containing resin.

[Item 21] A chlorine-containing resin molded body obtained from the chlorine-containing resin composition according to any one of [item 10] to [item 20].

[Item 22] A method for stabilizing a chlorine-containing resin by containing at least one member selected from 4,5-epoxycyclohexane-1,2-dicarboxylic acid diesters represented by the following general formula (1) in a chlorine-containing resin, wherein the ratio (molar ratio) of the linear-chain alkyl group with respect to the total amount of the alkyl groups constituting the dicarboxylic acid diester is 50 to 99%:

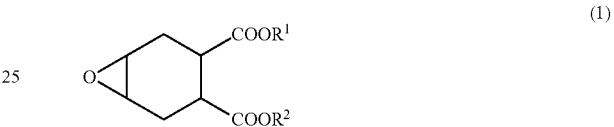

wherein $R^1$ and $R^2$ are the same or different and each represents a linear or branched-chain alkyl group having 7 to 13 carbon atoms.

[Item 23] The method according to [item 22], wherein the alkyl group is mainly composed of an alkyl group having 9 to 11 carbon atoms, in which the ratio (molar ratio) of alkyl group having 9 carbon atoms/alkyl group having 10 carbon atoms/alkyl group having 11 carbon atoms is in the range of 10 to 25/35 to 50/30 to 45.

[Item 24] The method according to [item 22], wherein the alkyl group contains an alkyl group having 9 carbon atoms in an amount of 90% or more (molar ratio).

[Item 25] The method according to any one of [item 22] to [item 24], wherein the ratio of the linear-chain alkyl group in the alkyl groups is 55 to 95%.

[Item 26] The method according to any one of [item 22] to [item 25], wherein the 4,5-epoxycyclohexane-1,2-dicarboxylic acid diester is obtained by epoxidation reaction of a 4-cyclohexene-1,2-dicarboxylic acid diester.

[Item 27] The method according to [item 26], wherein the 4-cyclohexene-1,2-dicarboxylic acid diester is obtained by esterification reaction of 4-cyclohexene-1,2-dicarboxylic acid or an acid anhydride thereof with a saturated aliphatic alcohol having 7 to 13 carbon atoms, and wherein the saturated aliphatic alcohol contains a saturated aliphatic alcohol having 9 to 11 carbon atoms as a main component and the linear chain ratio (molar ratio) of the saturated aliphatic alcohol is 50 to 99%.

[Item 28] A method for producing a 4,5-epoxycyclohexane-1,2-dicarboxylic acid diester used in the stabilizer for a chlorine-containing resin according to any one of [items 1] to [item 7], including a step of esterifying 4-cyclohexene-1,2-dicarboxylic acid or an acid anhydride thereof with a saturated aliphatic alcohol having 7 to 13 carbon atoms, optionally in the presence of a catalyst and optionally under an atmosphere or in an air stream of inert gas, and a step of epoxidizing the obtained esterified 4-cyclohexene-1,2-dicarboxylic acid diester in the presence of an epoxidizing agent.

[Item 29] The production method according to [item 28], wherein the saturated aliphatic alcohol is composed mainly of a saturated aliphatic alcohol having 9 to 11 carbon atoms, and the ratio (molar ratio) of saturated aliphatic alcohol having 9 carbon atoms/saturated aliphatic alcohol having 10 carbon atoms/saturated aliphatic alcohol having 11 carbon atoms is in the range of 10 to 25/35 to 50/30 to 45 or the ratio (molar ratio) of the saturated aliphatic alcohol having 9 carbon atoms is in the range of 90% or more.

[Item 30] The production method according to [item 28] or [item 29], wherein the linear chain ratio (molar ratio) of the saturated aliphatic alcohol is 50 to 99%.

As a result of extensive studies to solve the above problems, the present inventors have found that a novel epoxycyclohexane dicarboxylic acid diester having a specific structure is excellent in compatibility with a vinyl chloride-based resin, and a vinyl chloride-based resin composition containing the epoxycyclohexane dicarboxylic acid diester is excellent in effect of suppressing deterioration of physical properties and discoloration due to heat and light peculiar to the vinyl chloride resin and also can greatly improve the problems of cold resistance and volatility resistance, especially fogging resistance. Thus, such a vinyl chloride-based resin composition containing the dicarboxylic acid diester is found to be very useful as an interior material for automobiles, leading to complete the fourth embodiment of the present invention.

That is, the fourth embodiment of the present invention relates to a vinyl chloride-based resin composition for automotive interior materials, containing a novel epoxycyclohexane dicarboxylic acid diester having a specific structure; an automotive interior material containing the vinyl chloride-based resin composition; and a plasticizer and a stabilizer for vinyl chloride-based resins for automotive interior materials, the plasticizer and stabilizer containing a novel epoxycyclohexane dicarboxylic acid diester having a specific structure.

[Item 1] A vinyl chloride-based resin composition for automotive interior materials, containing a vinyl chloride-based resin and an epoxycyclohexane dicarboxylic acid diester, wherein the epoxycyclohexane dicarboxylic acid diester is a 4,5-epoxycyclohexane-1,2-dicarboxylic acid diester represented by the following general formula (1), and wherein the ratio (molar ratio) of the linear-chain alkyl group is 50 to 99% with respect to the total amount of the alkyl groups constituting the dicarboxylic acid diester:

(1)

wherein $R^1$ and $R^2$ are the same or different and each represents a linear or branched-chain alkyl group having 7 to 13 carbon atoms.

[Item 2] The vinyl chloride-based resin composition for automotive interior materials according to [item 1], wherein the alkyl group has 8 to 12 carbon atoms.

[Item 3] The vinyl chloride-based resin composition for automotive interior materials according to [item 1] or [item 2], wherein the alkyl group is mainly composed of an alkyl group having 9 to 11 carbon atoms, in which the ratio (molar ratio) of alkyl group having 9 carbon atoms/alkyl group having 10 carbon atoms/alkyl group having 11 carbon atoms is in the range of 10 to 25/35 to 50/30 to 45.

[Item 4] The vinyl chloride-based resin composition for automotive interior materials according to [item 1] or [item 2], wherein the alkyl group contains an alkyl group having 9 carbon atoms in an amount of 90% or more (molar ratio).

[Item 5] The vinyl chloride-based resin composition for automotive interior materials according to any one of [item 1] to [item 4], wherein the ratio of the linear-chain alkyl group in the alkyl groups is 55 to 95%.

[Item 6] The vinyl chloride-based resin composition for automotive interior materials according to any one of [item 1] to [item 4], wherein the ratio of the linear-chain alkyl group in the alkyl groups is 60 to 95%.

[Item 7] The vinyl chloride-based resin composition for automotive interior materials according to any one of [item 1] to [item 4], wherein the ratio of the linear-chain alkyl group in the alkyl groups is 70 to 95%.

[Item 8] The vinyl chloride-based resin composition for automotive interior materials according to any one of [item 1] to [item 7], wherein the 4,5-epoxycyclohexane-1,2-dicarboxylic acid diester is obtained by epoxidation reaction of a 4-cyclohexene-1,2-dicarboxylic acid diester.

[Item 9] The vinyl chloride-based resin composition for automotive interior materials according to [item 8], wherein the 4-cyclohexene-1,2-dicarboxylic acid diester is obtained by esterification reaction of 4-cyclohexene-1,2-dicarboxylic acid or an acid anhydride thereof with a saturated aliphatic alcohol having 7 to 13 carbon atoms, and wherein the linear chain ratio (molar ratio) of the saturated aliphatic alcohol is 50 to 99%.

[Item 10] The vinyl chloride-based resin composition for automotive interior materials according to any one of [item 1] to [item 9], wherein the content of the epoxycyclohexane dicarboxylic acid diester is 1 to 200 parts by weight with respect to 100 parts by weight of the vinyl chloride-based resin.

[Item 11] The vinyl chloride-based resin composition for automotive interior materials according to any one of [item 1] to [item 9], wherein the content of the epoxycyclohexane dicarboxylic acid diester is 5 to 150 parts by weight with respect to 100 parts by weight of the vinyl chloride-based resin.

[Item 12] The vinyl chloride-based resin composition for automotive interior materials according to anyone of [item 1] to [item 9], wherein the content of the epoxycyclohexane dicarboxylic acid diester is 1 to 30 parts by weight with respect to 100 parts by weight of the vinyl chloride-based resin.

[Item 13] The vinyl chloride-based resin composition for automotive interior materials according to any one of [item 1] to [item 9], wherein the content of the epoxycyclohexane dicarboxylic acid diester is 30 to 150 parts by weight with respect to 100 parts by weight of the vinyl chloride-based resin.

[Item 14] The vinyl chloride-based resin composition for automotive interior materials according to any one of [item 1] to [item. 13], further containing one or two or more plasticizers selected from the group consisting of a phthalic acid ester, a trimellitic acid ester, and a cyclohexane dicarboxylic acid ester.

[Item 15] The vinyl chloride-based resin composition for automotive interior according to [item 14], wherein the plasticizer is one or two or more kinds selected from the group consisting of diisodecyl phthalate, di(2-propylheptyl) phthalate, diundecyl phthalate, dialkyl(C9 to C11) phthalate, dialkyl(C10 to C13) phthalate, ditridecyl phthalate, tri-n- alkyl(C8, C10) trimellitate, tri-n-octyl trimellitate, tri-isononyl trimellitate, and trimellitic acid triester, and wherein the trimellitic acid triester is obtained from trimellitic acid and a saturated aliphatic alcohol having a ratio (molar ratio) of 90% or more of a saturated aliphatic alcohol having 9 carbon atoms and a ratio (molar ratio) of 50 to 99% of a linear-chain saturated aliphatic alcohol.

[Item 16] The vinyl chloride-based resin composition for automotive interior according to any one of [item 1] to [item 15], further containing a metal soap compound of an organic acid.

[Item 17] The vinyl chloride-based resin composition for automotive interior according to [item 16], wherein the metal soap compound is one or two or more fatty acid metal soaps selected from the group consisting of fatty acid calcium salt, fatty acid zinc salt, and fatty acid barium.

[Item 18] An automotive interior material comprising the vinyl chloride-based resin composition for automotive interior according to any one of [item 1] to [item 17].

[Item 19] A plasticizer for vinyl chloride-based resins for automotive interior materials comprising a 4,5-epoxycyclohexane-1,2-dicarboxylic acid diester represented by the following general formula (1), wherein the ratio (molar ratio) of the linear-chain alkyl group with respect to the total amount of the alkyl groups constituting the dicarboxylic acid diester is 50 to 99%:

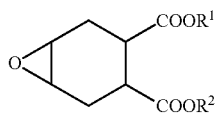

(1)

wherein $R^1$ and $R^2$ are the same or different and each represents a linear or branched-chain alkyl group having 7 to 13 carbon atoms.

[Item 20] A stabilizer for vinyl chloride-based resins for automotive interior materials comprising a 4,5-epoxycyclohexane-1,2-dicarboxylic acid diester represented by the following general formula (1), wherein the ratio (molar ratio) of the linear-chain alkyl group with respect to the total amount of the alkyl groups constituting the dicarboxylic acid diester is 50 to 99%:

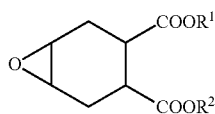

(1)

wherein $R^1$ and $R^2$ are the same or different and each represents a linear or branched-chain alkyl group having 7 to 13 carbon atoms.

As a result of intensive investigation in order to solve the above problem in view of such current situation, the present inventors have found that by blending an epoxycyclohexane dicarboxylic acid diester having a specific structure, there is obtained a medical vinyl chloride-based resin composition which has little deterioration after sterilization and disinfection treatment, can be stably used, has good processability and flexibility, and has improved heat resistance and cold resistance. It has been also found that a medical material made of the medical vinyl chloride-based resin composition is effective as a medical material with less deterioration after sterilization and disinfection treatment, can be stably used, and has good mechanical performance such as flexibility as well as improved heat resistance and cold resistance. The fifth embodiment of the present invention has been completed based on these findings.

That is, the fifth embodiment of the present invention provides a medical vinyl chloride-based resin composition and a medical material, containing a novel epoxycyclohexane dicarboxylic acid diester having a specific structure shown below.

[Item 1] A medical vinyl chloride-based resin composition comprising an epoxycyclohexane dicarboxylic acid diester, wherein the epoxycyclohexane dicarboxylic acid diester contains a 4,5-epoxycyclohexane-1,2-dicarboxylic acid diester represented by the following general formula (1), wherein the ratio (molar ratio) of the linear-chain alkyl group with respect to the total amount of the alkyl groups constituting the dicarboxylic acid diester is 50 to 99%:

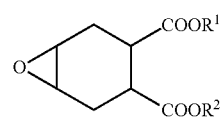

(1)

wherein $R^1$ and $R^2$ are the same or different and each represents a linear or branched-chain alkyl group having 7 to 13 carbon atoms.

[Item 2] The medical vinyl chloride-based resin composition according to [item 1], wherein the alkyl group has 8 to 12 carbon atoms.

[Item 3] The medical vinyl chloride-based resin composition according to [item 1] or [item 2], wherein the alkyl group is mainly composed of an alkyl group having 9 to 11 carbon atoms, in which the ratio (molar ratio) of alkyl group having 9 carbon atoms/alkyl group having 10 carbon atoms/alkyl group having 11 carbon atoms is in the range of 10 to 25/35 to 50/30 to 45.

[Item 4] The medical vinyl chloride-based resin composition according to [item 1] or [item 2], wherein the alkyl group contains an alkyl group having 9 carbon atoms in an amount of 90% or more (molar ratio).

[Item 5] The medical vinyl chloride-based resin composition according to any one of [item 1] to [item 4], wherein the ratio of the linear-chain alkyl group in the alkyl groups is 55 to 98%.

[Item 6] The medical vinyl chloride-based resin composition according to any one of [item 1] to [item 4], wherein the ratio of the linear-chain alkyl group in the alkyl groups is 55 to 95%.

[Item 7] The medical vinyl chloride-based resin composition according to any one of [item 1] to [item 4], wherein the ratio of the linear-chain alkyl group in the alkyl groups is 60 to 95%.

[Item 8] The medical vinyl chloride-based resin composition according to any one of [item 1] to [item 4], wherein the ratio of the linear-chain alkyl group in the alkyl groups is 70 to 95%.

[Item 9] The medical vinyl chloride-based resin composition according to any one of [item 1] to [item 8], wherein the 4,5-epoxycyclohexane-1,2-dicarboxylic acid diester is an epoxy compound of a 4-cyclohexene-1,2-dicarboxylic acid diester.

[Item 10] The medical vinyl chloride-based resin composition according to [item 9], wherein the 4-cyclohexene-1, 2-dicarboxylic acid diester is an ester compound of 4-cyclohexene-1,2-dicarboxylic acid or an acid anhydride thereof with a saturated aliphatic alcohol having 7 to 13 carbon atoms, and wherein the saturated aliphatic alcohol contains a saturated aliphatic alcohol having 9 to 11 carbon atoms as a main component and the linear chain ratio (molar ratio) of the saturated aliphatic alcohol is 50 to 99%.

[Item 11] The medical vinyl chloride-based resin composition according to any one of [item 1] to [item 10], wherein the content of the epoxycyclohexane dicarboxylic acid diester is 5 to 200 parts by weight with respect to 100 parts by weight of the vinyl chloride-based resin.

[Item 12] The medical vinyl chloride-based resin composition according to any one of [item 1] to [item 10], wherein the blending amount of the epoxycyclohexane dicarboxylic acid diester is 30 to 150 parts by weight with respect to 100 parts by weight of the vinyl chloride-based resin, and the medical vinyl chloride-based resin composition is a medical soft vinyl chloride-based resin composition.

[Item 13] The medical vinyl chloride-based resin composition according to [item 12], wherein the content of the epoxycyclohexane dicarboxylic acid diester is 40 to 100 parts by weight with respect to 100 parts by weight of the vinyl chloride-based resin.

[Item 14] The medical vinyl chloride-based resin composition according to any one of [item 1] to [item 10], wherein the blending amount of the epoxycyclohexane dicarboxylic acid diester is 5 parts by weight or more and less than 30 parts by weight with respect to 100 parts by weight of the vinyl chloride-based resin, and the medical vinyl chloride-based resin composition is a medical semi-hard vinyl chloride-based resin composition.

[Item 15] The medical vinyl chloride-based resin composition according to [item 14], wherein the content of the epoxycyclohexane dicarboxylic acid diester is 5 parts by weight or more and less than 20 parts by weight with respect to 100 parts by weight of the vinyl chloride-based resin.

[Item 16] The medical vinyl chloride-based resin composition according to any one of [item 1] to [item 15], further comprising a fatty acid calcium salt and/or a fatty acid zinc salt.

[Item 17] The medical vinyl chloride-based resin composition according to [item 16], wherein the blending amount of the fatty acid calcium salt and/or the fatty acid zinc salt (when either one is used, the amount of either, or when both are used, the total amount) is 0.1 to 10 parts by weight with respect to 100 parts by weight of the vinyl chloride-based resin.

[Item 18] The medical vinyl chloride-based resin composition according to any one of [item 1] to [item 17], further comprising a silane compound.

[Item 19] The medical vinyl chloride-based resin composition according to [item 18], wherein the content of the silane compound is 0.1 to 15 parts by weight with respect to 100 parts by weight of the vinyl chloride-based resin.

[Item 20] A medical material comprising the medical vinyl chloride-based resin composition according to any one of [item 1] to [item 19].

According to the first embodiment of the present invention, it is possible to obtain a novel epoxy group-containing epoxycyclohexane dicarboxylic acid diester that can be suitably used as a plasticizer and as a stabilizer in a chlorine-containing resin. Further, when the epoxycyclohexane dicarboxylic acid diester is used as a plasticizer, such diester can be used as a plasticizer which has good inherent plasticizing performance, is excellent in heat resistance and cold resistance, and meets more severe requirements in recent years. When the epoxycyclohexane dicarboxylic acid diester is used as a stabilizer, the diester is also excellent as a stabilizer in chlorine-containing resin system.

The plasticizer for vinyl chloride-based resin in accordance with the second embodiment of the present invention is superior in plasticizing efficiency and flexibility because it is excellent in compatibility with a vinyl chloride-based resin, and has greatly improved cold resistance and volatility resistance as compared with the conventional one. The use of such a plasticizer is extremely useful for obtaining a vinyl chloride-based resin molded body that meets the demands for heat resistance and cold resistance becoming increasingly severer in recent years. In addition, by the effect of the epoxy group contained in the compound, the plasticizer is expected to have an ability to prevent aging by heat and light. Thus, such plasticizer is particularly useful for applications such as long-term outdoor use.

The stabilizer for chlorine-containing resins of the third embodiment of the present invention can be used as a stabilizer for chlorine-containing resins, which has excellent effect (stabilizing effect) as a stabilizer, good compatibility with the resin, improved volatility resistance, less bleeding and migration to a laminated resin, and stable effect for a long time. Further, the chlorine-containing resin composition blended with the stabilizer is a stabilized chlorine-containing resin composition that can be stably used without fear of fogging and the like. In addition, a molded body of the stabilized chlorine-containing resin composition is extremely useful for applications such as electric wire coating. Furthermore, by adopting the stabilization method using the stabilizer according to the present invention, the possibility of using a chlorine-containing resin can be expanded even in applications such as long-term outdoor use, which was considered to be difficult to use so far.

By containing a plasticizer or a stabilizer for automotive interior materials which is excellent in compatibility with a resin, is easy to be mixed with a resin, and has improved cold resistance, volatility resistance, especially fogging resistance, it is possible to obtain a vinyl chloride-based resin composition for automotive interior materials according to the fourth embodiment of the present invention, the composition having improvements in cold resistance, volatility resistance, especially fogging resistance, and being excellent in light resistance and heat aging resistance. Thus, the automotive interior material containing the vinyl chloride-based resin composition for automotive interior material has excellent light resistance and heat aging resistance, is stable without causing problems such as deterioration of physical properties and discoloration even under severe conditions such as blazing sun, can maintain its stable quality, and is extremely useful as an automotive interior material that can be used without causing problems such as cracking during use in a cold district or without fogging at high temperatures such as in the blazing sun.

The medical vinyl chloride-based resin composition of the fifth embodiment of the present invention is good in mechanical properties typified by processability and flexibility; has improved heat resistance and cold resistance; has a remarkably small decrease in the content of plasticizer due to volatilization even after heat sterilization treatment of the composition; maintains good mechanical properties; and shows almost no discoloration even in sterilization or disinfection treatment by ultraviolet rays or irradiation. A medical material obtained from the vinyl chloride-based resin composition has good mechanical properties such as flexibility, improved heat resistance and cold resistance, little deterioration of mechanical properties after various sterilization and disinfection treatments, and almost no discoloration. Therefore, the medical vinyl chloride-based resin composition can be used stably.

MODE FOR CARRYING OUT THE INVENTION

<Epoxycyclohexane Dicarboxylic Acid Diester>

The epoxycyclohexane dicarboxylic acid diester of the present invention is characterized by being a 4,5-epoxycyclohexane-1,2-dicarboxylic acid diester represented by the following general formula (1).

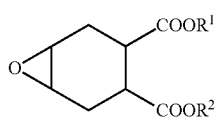
(1)

In the formula, $R^1$ and $R^2$ are the same or different and each represents a linear or branched-chain alkyl group having 7 to 13 carbon atoms, preferably 8 to 12 carbon atoms, and the ratio (molar ratio) of the linear-chain alkyl group with respect to the total amount of the alkyl groups represented by $R^1$ and $R^2$ in the formula is from 50 to 99%, preferably from 55 to 98%, more preferably from 55 to 95%, even more preferably from 60 to 95%, particularly preferably from 70 to 95%. Please note that satisfying this ratio means to include the case where the epoxycyclohexane dicarboxylic acid diester of the present invention is a mixture of 4,5-epoxycyclohexane-1,2-dicarboxylic acid diesters. The ratio in the case of the mixture means the ratio (molar ratio) of the linear-chain alkyl group with respect to the total amount of the alkyl groups of the whole mixture.

As a preferable embodiment, there is recommended an embodiment such that the alkyl group is preferably composed mainly of an alkyl group having 9 to 11 carbon atoms, and the ratio (molar ratio) of alkyl group having 9 carbon atoms/alkyl group having 10 carbon atoms/alkyl group having 11 carbon atoms is in the range of 10 to 25/35 to 50/30 to 45, or an embodiment such that an alkyl group having 9 carbon atoms occupies 90% or more (molar ratio) with respect to the total amount of the alkyl groups constituting the epoxycyclohexane dicarboxylic acid diester.

In the 4,5-epoxycyclohexane-1,2-dicarboxylic acid diesters, stereoisomers may exist in the cyclohexane ring (chair conformation, boat conformation), the oxirane ring (cis form, transform) to the cyclohexane ring, the alkyloxycarbonyl group (cis form, trans form) to the cyclohexane ring, and the oxirane ring and the alkyloxycarbonyl group (cis form, trans form) via the cyclohexane ring, respectively. In the present invention, there is no particular limitation to such stereoisomers as long as the desired performance can be obtained, and either cis form alone, trans form alone, or a mixture of cis form and trans form can be used. As described below, in general, in the production by esterification with 4-cyclohexene-1,2-dicarboxylic anhydride as a starting material at a reaction temperature lower than the reaction temperature around 210° C., followed by epoxidation, the isomeric structure of the alkyloxycarbonyl group to the cyclohexane ring is dominant in the cis form.

There is recommended an embodiment of a mixture of a cis form and a trans form, wherein the isomer structure of the oxirane ring and the alkyloxycarbonyl group via the cyclohexane ring has an isomer ratio (cis form/trans form, molar ratio) measured by proton nuclear magnetic resonance spectroscopy in the range of preferably 5/95 to 35/65, more preferably 10/90 to 30/70, particularly preferably 15/85 to 25/75.

Please note that the isomer structure of the oxirane ring and the alkyloxycarbonyl group via the cyclohexane ring as referred to herein means that the cis form exists in such a case where the oxirane ring and the alkyloxycarbonyl group are located to the cyclohexane ring in the same direction as shown in the following structural formula (2), and the trans form exists when the oxirane ring and the alkyloxycarbonyl group are located to the cyclohexane ring in the different direction as shown in the structural formula (3). Its isomer ratio, that is, the isomer ratio of cis form and trans form, can be obtained from the results of nuclear magnetic resonance spectroscopic analysis ($^1$H-NMR). The measurement can be easily carried out, for example, by dissolving the sample in deuterated chloroform solvent or the like and using a versatile nuclear magnetic resonance spectrometer. Further, among the two peaks attributed to the methine hydrogen at the oxirane ring site existing in the vicinity of 3.2 ppm of the analysis chart obtained by the above measurement, the peak shifted to the lower magnetic field side is assigned to as the peak of the trans form and the peak not shifted to the low magnetic field side is assigned to as the peak of the cis form, and the isomer ratio is calculated from the integral value of each peak using the following formula.

Isomer ratio of cis form/trans form=[{Integral value of cis form/(Integral value of cis form+Integral value of trans form)}×100]/[{Integral value of trans form/(Integral value of cis form+Integral value of trans form)×100]}

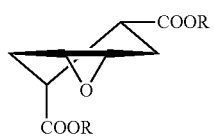
(2)

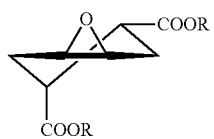
(3)

The above isomer structure can be isomerized to the desired isomer structure, i.e., isomer ratio, by heat or chemical agents depending on the purpose.

The 4,5-epoxycyclohexane-1,2-dicarboxylic acid diester (hereinafter referred to as "present diester" in some cases) according to the present invention is not particularly limited by the production method thereof as long as the present diester has the above-mentioned specific structure. However, the 4,5-epoxycyclohexane-1,2-dicarboxylic acid diester can be easily obtained, for example, by esterifying a 4-cyclohexene-1,2-dicarboxylic acid or an acid anhydride thereof with a saturated aliphatic alcohol having a specific structure and epoxidizing the obtained 4-cyclohexene-1,2-dicarboxylic acid diester (hereinafter sometimes referred to as the "raw material ester") under predetermined conditions. Alternatively, the 4,5-epoxycyclohexane-1,2-dicarboxylic acid diester can be obtained by a method of esterification between the obtained 4,5-epoxycyclohexane-1,2-dicarboxylic acid or an acid anhydride thereof and a saturated aliphatic alcohol having a specific structure after epoxidation of 4-cyclohexene-1,2-dicarboxylic acid or an acid anhydride thereof. Depending on the type of the saturated aliphatic alcohol, there is also a method in which a lower alcohol having about 1 to 6 carbon atoms is esterified in advance and then the saturated aliphatic alcohol is added for carrying out the transesterification to obtain the 4,5-epoxycyclohexane-1,2-dicarboxylic acid diester. From the viewpoint of convenience and practical utility, the method of epoxidation after esterification is most preferable.

That is, the 4,5-epoxycyclohexane-1,2-dicarboxylic acid diester according to the present invention is characterized by having a structure formed by epoxidation of the unsaturated bond on the cyclohexene ring in the 4-cyclohexene-1,2-dicarboxylic acid diester which is obtained by esterification reaction between 4-cyclohexene-1,2-dicarboxylic acid or an acid anhydride thereof and a saturated aliphatic alcohol.

[Saturated Aliphatic Alcohol]

The saturated aliphatic alcohol used for the above esterification reaction or transesterification reaction is a linear or branched-chain saturated aliphatic alcohol having 7 to 13 carbon atoms, preferably 8 to 12 carbon atoms, more preferably 9 to 11 carbon atoms, and is particularly preferably (i) a linear or branched-chain saturated aliphatic alcohol containing a saturated aliphatic alcohol having 9 carbon atoms in a ratio (molar ratio) of 90% or more, more preferably 95% or more, or (ii) a saturated aliphatic alcohol composed mainly of a saturated aliphatic alcohol having 9 to 11 carbon atoms, wherein the ratio (molar ratio) of alkyl group having 9 carbon atoms/alkyl group having 10 carbon atoms/alkyl group having 11 carbon atoms is in the range of 10 to 25/35 to 50/30 to 45. The above "mainly" means that the ratio (molar ratio) of the saturated aliphatic alcohol having 9 to 11 carbon atoms in the whole saturated aliphatic alcohol is 90% or more, preferably 95% or more. The saturated aliphatic alcohol is a raw material alcohol to be a saturated aliphatic alkyl group constituting the 4,5-epoxycyclohexane-1,2-dicarboxylic acid diester represented by the general formula (1), that is, the explanation of such alcohol is synonymous with the explanation of the alkyl group.

In addition, the saturated aliphatic alcohol is characterized in that the ratio (molar ratio) of the linear-chain saturated aliphatic alcohol in the saturated aliphatic alcohol is from 50 to 99%, preferably from 55 to 98%, more preferably from 55 to 95%, even more preferably 60 to 95%, particularly preferably 70 to 95%.

Details of preferred embodiments of the saturated aliphatic alcohol include (i) a linear or branched-chain saturated aliphatic alcohol having 7 to 13 carbon atoms, wherein the ratio (molar ratio) of the saturated aliphatic alcohol having 9 carbon atoms is 90% or more, preferably 95% or more, and the ratio (molar ratio) of the linear-chain saturated aliphatic alcohol is from 50 to 99%, preferably from 55 to 98%, more preferably from 55 to 95%, even more preferably from 60 to 95%, particularly preferably from 70 to 95%, or (ii) a mixture of linear or branched-chain saturated aliphatic alcohols having 7 to 13 carbon atoms, composed mainly of saturated aliphatic alcohols having 9 to 11 carbon atoms, wherein the ratio (molar ratio) occupied by each alcohol having 9, 10 or 11 carbon atoms is in the range of 10 to 25/35 to 50/30 to 45, and the ratio (molar ratio) occupied by the linear-chain saturated aliphatic alcohol is from 50 to 99%, preferably from 55 to 98%, more preferably from 55 to 95%, even more preferably from 60 to 95%, particularly preferably from 70 to 95%. These embodiments are recommended.

If a saturated aliphatic alcohol having less than 7 carbon atoms is contained, not only it is difficult to obtain a sufficient cold resistance or stabilizing effect but also the volatility resistance is lowered and problems such as fogging may occur. In addition, if a saturated aliphatic alcohol having more than 13 carbon atoms is contained, the compatibility with the resin tends to be poor, resulting in the deterioration of processability or plasticization efficiency, and uneven mixing with the resin occurs. As a result, there is a concern that variations may occur in the stabilizing effect, which is not desirable. Similarly, when the ratio of the linear-chain saturated aliphatic alcohol is less than 50%, the cold resistance or volatility resistance tends to be lowered, and when the ratio of the linear-chain saturated aliphatic alcohol exceeds 99%, the compatibility with the resin becomes worse and there are concerns that the plasticization efficiency or the like is lowered or the effect of stabilization varies, which is not desirable either.

The saturated aliphatic alcohol containing 90% or more of a saturated aliphatic alcohol having 9 carbon atoms and having a ratio of linear-chain saturated aliphatic alcohol of from 50 to 99% can be produced by a production method including (1) a step of producing an aldehyde having 9 carbon atoms by a hydroformylation reaction of 1-octene, carbon monoxide, and hydrogen, and (2) a step of reducing the aldehyde having 9 carbon atoms to an alcohol by hydrogenation. The saturated aliphatic alcohol can be employed by directly using the saturated aliphatic alcohol obtained in the production method, or by formulating the saturated aliphatic alcohol obtained in the production method.

In the hydroformylation reaction in the step (1), an aldehyde having 9 carbon atoms can be produced, for example, by reacting 1-octene, carbon monoxide, and hydrogen in the presence of a cobalt catalyst or a rhodium catalyst.

In the hydrogenation of the step (2), an aldehyde having 9 carbon atoms can be reduced to an alcohol by hydrogenation under hydrogen pressure in the presence of a noble metal catalyst such as a nickel catalyst or a palladium catalyst. Specific examples of commercially available products include LINEVOL 9 manufactured by Shell Chemicals Co., Ltd. and n-Nonanol manufactured by Oxea Corporation.

Likewise, the saturated aliphatic alcohol containing mainly a saturated aliphatic alcohol having 9 to 11 carbon atoms and having a ratio (molar ratio) of alkyl group having 9 carbon atoms/alkyl group having 10 carbon atoms/alkyl group having 11 carbon atoms in the range of 10 to 25/35 to 50/30 to 45, wherein the ratio of a linear-chain saturated aliphatic alcohol is from 50 to 99%, can be produced by a production method including (1) a step of producing an aldehyde having 9 to 11 carbon atoms by a hydroformylation reaction of 1-octene, 1-nonene, 1-decene, carbon monoxide, and hydrogen and (2) a step of reducing the aldehyde having 9 to 11 carbon atoms to an alcohol by hydrogenation. The saturated aliphatic alcohol can be employed by directly using the saturated aliphatic alcohol obtained in the production method, or by formulating the saturated aliphatic alcohol obtained in the production method.

The hydroformylation reaction in the step (1) can be carried out, for example, by reacting 1-octene, 1-nonene, 1-decene, carbon monoxide, and hydrogen in the presence of a cobalt catalyst or a rhodium catalyst to obtain an aldehyde having 9 to 11 carbon atoms.

In the hydrogenation of the step (2), the aldehyde having 9 to 11 carbon atoms can be reduced to an alcohol by hydrogenation under hydrogen pressure in the presence of a noble metal catalyst such as a nickel catalyst or a palladium catalyst. Specific examples of commercially available products include NEODOL 911 manufactured by Shell Chemicals Co., Ltd. and the like.

[Esterification Reaction]

The esterification reaction as used herein means an esterification reaction between the raw material alcohol and 4-cyclohexene-1,2-dicarboxylic acid or an acid anhydride thereof to obtain a 4-cyclohexene-1,2-dicarboxylic acid diester (raw material ester) which is a raw material in the epoxidation reaction for obtaining the present diester. In performing the esterification reaction, the raw material alcohol is recommended to be used in an amount of, for example, preferably from 2.00 moles to 5.00 moles, more preferably 2.01 moles to 3.00 moles, especially from 2.02 moles to 2.50 moles, with respect to 1 mole of the 4-cyclohexene-1,2-dicarboxylic acid or an acid anhydride thereof.

In the case of using a catalyst for the esterification reaction, examples of the catalyst include a mineral acid, an organic acid, a Lewis acid, and the like. More specifically, examples of the mineral acid include sulfuric acid, hydrochloric acid, phosphoric acid, and the like. Examples of the organic acid include p-toluenesulfonic acid, methanesulfonic acid, and the like. Examples of the Lewis acid include an aluminum derivative, a tin derivative, a titanium derivative, a lead derivative, a zinc derivative, and the like, and one or two or more kinds of these can be used singly or in combination.

Among them, p-toluenesulfonic acid, tetraalkyl titanate having 3 to 8 carbon atoms, titanium oxide, titanium hydroxide, tin fatty acid having 3 to 12 carbon atoms, tin oxide, tin hydroxide, zinc oxide, zinc hydroxide, lead oxide, lead hydroxide, aluminum oxide, and aluminum hydroxide are particularly preferable. The amount of the catalyst to be used is recommended to be preferably from 0.01% by weight to 5.0% by weight, more preferably from 0.02% by weight to 4.0% by weight, particularly preferably from 0.03% by weight to 3.0% by weight, with respect to the total weight of the acid component and the alcohol component which are each a raw material for synthesizing the ester.

The esterification temperature is exemplified by 100° C. to 230° C., and the reaction is usually completed within 3 hours to 30 hours.

The 4-cyclohexene-1,2-dicarboxylic acid or its acid anhydride, which is a raw material for the starting ester, is not particularly limited, and those produced by known methods, commercially available products, available reagents, and the like can be used. For example, RIKACID TH (trade name, manufactured by New Japan Chemical Co., Ltd.) and the like are exemplified as a commercially available product. The 4-cyclohexene-1,2-dicarboxylic anhydride is usually obtained by Diels-Alder reaction of maleic anhydride and 1,3-butadiene. From the viewpoint of esterification reaction, 4-cyclohexene-1,2-dicarboxylic anhydride is recommended to be used.

In the esterification reaction, a water entraining agent such as benzene, toluene, xylene, and cyclohexane can be used to accelerate the distillation of water produced by the reaction.

When an oxygen-containing organic compound such as an oxide, a peroxide, and a carbonyl compound is produced due to oxidative deterioration of the raw material, the produced ester and the organic solvent (water entraining agent) during the esterification reaction, the oxygen-containing organic compound exerts an adverse effect on heat resistance, light resistance, and the like. Thus, it is desirable to carry out the reaction in an inert gas atmosphere such as nitrogen gas or in an inert gas stream at normal pressure or under reduced pressure. After completion of the esterification reaction, it is recommended to distill off the excess alcohol or the raw material alcohol under reduced pressure or atmospheric pressure.

The raw material ester obtained by the esterification method may be subsequently purified by base treatment (neutralization treatment)→water washing treatment, liquid-liquid extraction, distillation (depressurization, dehydration treatment), adsorption treatment and the like as needed.

The base used in the base treatment is not particularly limited as long as the base is a basic compound, and examples thereof include sodium hydroxide, sodium carbonate, and the like.

Examples of the adsorbent used in the adsorption treatment include activated carbon, activated clay, activated alumina, hydrotalcite, silica gel, silica alumina, zeolite, magnesia, calcia, diatomaceous earth, and the like. These adsorbents can be used singly or in appropriate combination of two or more kinds thereof.

The purification treatment after the esterification may be carried out at normal temperature, but the purification treatment may also be carried out by heating at about 40 to 90° C.

[Epoxidation Reaction]

The epoxidation reaction as used herein means an epoxidation reaction of an unsaturated bond on the cyclohexene ring in the raw material ester for obtaining the present diester and is usually carried out easily by a method described in "Yuki Gosei Kagaku (Synthetic Organic Chemistry) Vol. 23, No. 7, pp 612-619 (1985)" or the like. For example, there are exemplified by (i) a method in which an organic peracid such as peracetic acid and performic acid is used as the epoxidizing agent and (ii) a method in which hydrogen peroxide is used as the epoxidizing agent.

More specifically, in the case of the method (i), the reaction is completed, for example, by adding peracetic acid obtained by reacting hydrogen peroxide with acetic anhydride or acetic acid in the presence of a strong acid such as sulfuric acid as a catalyst to the raw material ester, stirring the mixture at 20 to 30° C. for several hours, gradually raising the temperature to reach the temperature of 50 to 60° C., and maintaining the temperature for 2 to 3 hours. As the organic peracid, monoperphthalic acid, m-chloroperbenzoic acid, trifluoroperacetic acid and the like can also be used in addition to the above peracids.

In the case of the method (ii), the epoxidation can be carried out, for example, by reacting hydrogen peroxide with a raw material ester in the co-presence of an oxygen carrier such as formic acid and a strong acid catalyst such as sulfuric acid. More specifically, using acetic acid or formic acid in a small amount of 0.5 moles or less and sulfuric acid as a catalyst in a small amount of 0.05 moles or less with respect to 1 mole of hydrogen peroxide, the reaction is carried out by maintaining the mixture at 40 to 70° C. for 2 to 15 hours. Thereby, the raw material ester can be easily epoxidized. As the catalyst, phosphoric acid, hydrochloric acid, nitric acid, boric acid, or salts thereof are well known in addition to the above catalysts, and sulfonic acid type strongly acidic cation exchange resins, aluminum oxides, and the like are also effective.

The present diester obtained by the epoxidation method may be subsequently purified by aqueous phase removal, water washing treatment, liquid-liquid extraction, dehydration treatment, vacuum distillation, adsorption treatment or the like as needed.

Examples of the adsorbent used in the adsorption treatment include activated carbon, activated clay, activated alumina, hydrotalcite, silica gel, silica alumina, zeolite, magnesia, calcia, diatomaceous earth and the like. These adsorbents can be used singly or in appropriate combination of two or more kinds thereof.

The purification treatment after the epoxidation may be carried out at normal temperature, but such purification may also be carried out by heating to about 40 to 100° C.

It has been confirmed from the results of proton nuclear magnetic resonance spectroscopy that most of compounds having the isomer structure of the alkyloxycarbonyl group with respect to the cyclohexane ring of the present diester obtained within the above-mentioned method and conditions exist in the cis form.

<Use as Plasticizer>

The present diester can be suitably used as a plasticizer, particularly as a plasticizer for vinyl chloride-based resins. That is, the plasticizer is characterized by comprising the epoxycyclohexane dicarboxylic acid diester having a specific structure according to the present invention. As a preferred embodiment, it is recommended to use, as a plasticizer, an epoxycyclohexane dicarboxylic acid diester compound having an isomer ratio (cis form/trans form, molar ratio) of the oxirane ring and the alkyloxycarbonyl group via the cyclohexane ring of from 5/95 to 35/65 measured by proton nuclear magnetic resonance spectroscopy.

<Use as Stabilizer for Chlorine-Containing Resins>

The present diester can be suitably used as a stabilizer for chlorine-containing resins. That is, the stabilizer is characterized by containing the epoxycyclohexane dicarboxylic acid diester having a specific structure according to the present invention. In a preferred embodiment, it is recommended to use an epoxycyclohexane dicarboxylic acid diester compound as the stabilizer having an isomer ratio (cis form/trans form, molar ratio) of the oxirane ring site of from 5/95 to 35/65 measured by proton nuclear magnetic resonance spectroscopy.

The resin composition containing the epoxycyclohexane dicarboxylic acid diester having a specific structure according to the present invention and the molded body thereof can be suitably used for automobile mountings (e.g. automobile underbody coat, instrument panel, console, door sheet, under carpet, trunk sheet, door trim, etc.), various leathers, decorative sheets, agricultural films, films for food packaging, electric wire coating, various foam products, hoses, medical tubes, tubes for food materials, gaskets for refrigerators, packings, wallpaper, flooring materials, boots, curtains, shoe soles, gloves, water sealing plates, toys, decorative boards, blood bags, infusion bags, tarpaulins, mats, sealing materials, waterproof sheets, civil engineering sheets, roofing, waterproof sheets, insulating sheets, industrial tapes, glass films, erasing of letters, and the like.

<Vinyl Chloride-Based Resin Composition>

The vinyl chloride-based resin composition of the present invention can be obtained by blending the present diester as a plasticizer or as a stabilizer with a vinyl chloride-based resin. The content of the present diester in the vinyl chloride-based resin composition according to the present invention is appropriately selected depending on the applications, but is preferably 1 to 200 parts by weight with respect to 100 parts by weight of the vinyl chloride-based resin.

[Vinyl Chloride-Based Resin]

The vinyl chloride-based resin used in the present invention is a homopolymer of vinyl chloride or vinylidene chloride, and a copolymer of vinyl chloride or vinylidene chloride, and the production method thereof is carried out by a conventionally known polymerization method. For example, in the case of a versatile vinyl chloride-based resin, a method of suspension polymerization in the presence of an oil-soluble polymerization catalyst and the like can be mentioned. In the case of a vinyl chloride paste resin, a method of emulsion polymerization in an aqueous medium in the presence of a water-soluble polymerization catalyst and the like can be mentioned. The degree of polymerization of these vinyl chloride-based resins is usually from 300 to 5000, preferably from 400 to 3500, even more preferably from 700 to 3000. If the degree of polymerization is too low, the heat resistance and the like are deteriorated, whereas if the degree of polymerization is too high, the molding processability tends to decrease.

In the case of a copolymer, examples thereof include copolymers of a vinyl chloride monomer and an α-olefin having 2 to 30 carbon atoms (e.g. ethylene, propylene, 1-butene, 1-pentene, 1-hexene, 1-heptene, 1-octene, 1-nonene, 1-decene, 1-undecene, 1-dodecene, 1-tridecene, 1-tetradecene, etc.), acrylic acid or esters thereof, methacrylic acid and esters thereof, maleic acid and esters thereof, a vinyl compound (e.g. vinyl acetate, vinyl propionate, alkyl vinyl ether, etc.), a polyfunctional monomer (e.g. diallyl phthalate, etc.), or a mixture thereof; ethylene-acrylate ester copolymers (e.g. ethylene-ethyl acrylate copolymer, etc.); ethylene-methacrylate ester copolymers; ethylene-vinyl acetate copolymers (EVA); chlorinated polyethylene; butyl rubber; crosslinked acrylic rubber; polyurethane; butadiene-styrene-methyl methacrylate copolymers (MBS); butadiene-acrylonitrile-(α-methyl) styrene copolymers (ABS); styrene-butadiene copolymers; and graft copolymers obtained by grafting a vinyl chloride monomer to polyethylene, polymethyl methacrylate or a mixture thereof; and the like.

<Soft Vinyl Chloride-Based Resin Composition>

The soft vinyl chloride-based resin composition of the present invention can be obtained by blending the present diester as the plasticizer with the vinyl chloride-based resin. The content of the present diester of the present invention in the soft vinyl chloride-based resin composition is appropriately selected depending on the applications, but the content is preferably from 20 to 200 parts by weight, more preferably from 30 to 150 parts by weight, with respect to 100 parts by weight of the vinyl chloride-based resin. When the content of the present diester is 20 parts by weight or more, sufficient flexibility can be obtained even in the applications requiring flexibility, and in the applications requiring much more flexibility, flexibility is imparted by appropriately adjusting the blended amount. In the applications in which bleeding or the like to the surface of a molded product is feared, if the content of the present diester is 200 parts by weight or less, there is no fear of bleeding or the like, and the present diester can be preferably used. However, when a filler or the like is added to the vinyl chloride-based resin composition, the filler itself may absorb oil, so that the plasticizer may be blended beyond the above range. For example, when 100 parts by weight of calcium carbonate is blended as a filler with respect to 100 parts by weight of the vinyl chloride-based resin, the plasticizer may be blended up to about 500 parts by weight.

For the vinyl chloride-based resin composition or the soft vinyl chloride-based resin composition, other known plasticizers may be used together with the present diester. In addition, if necessary, additives such as a flame retardant, a stabilizer, a stabilizing aid, a coloring agent, a processing aid, a filler, an antioxidant (an aging inhibitor), an ultraviolet absorber, a light stabilizer (e.g. a hindered amine, etc.), a lubricant, or an antistatic agent or the like is appropriately blended and used in many cases.

Other plasticizers and additives other than the present diester may be used singly or in combination of two or more kinds thereof together with the present diester.

As other plasticizers that can be used in combination with the present diester, known plasticizers conventionally used in the technical field can be used and include, for example, benzoic acid esters (e.g. diethylene glycol dibenzoate, etc.); phthalic acid esters (e.g. dibutyl phthalate (DBP), di-2-ethylhexyl phthalate (DOP), diisononyl phthalate (DINP), diisodecyl phthalate (DIDP), di(2-propylheptyl) phthalate (DPHP), diundecyl phthalate (DUP), ditridecyl phthalate (DTDP), bis(2-ethylhexyl) terephthalate (DOTP), bis(2-ethylhexyl) isophthalate (DOIP), etc.); cyclohexane dicarboxylic acid esters (e.g. bis(2-ethylhexyl) cyclohexane-1,2-dicarboxylate (DOCH), diisononyl cyclohexane-1,2-dicarboxylate (DINCH), etc.); alicyclic dibasic acid esters such as tetrahydrophthalic acid esters (e.g. bis(2-ethylhexyl) 4-cyclohexene-1,2-dicarboxylate (DOTH), etc.); aliphatic dibasic acid esters (e.g. di-2-ethylhexyl adipate (DOA), diisononyl adipate (DINA), diisodecyl adipate (DIDA), di-2-ethylhexyl sebacate (DOS), diisononyl sebacate (DINS), etc.); trimellitic acid esters (e.g. tri-2-ethylhexyl trimellitate (TOTM), triisononyl trimellitate (TINTM), triisodecyl trimellitate (TIDTM), tri-n-alkyl(C8, C10) trimellitate (TRIMEX N-08), trimellitic acid triesters of a saturated aliphatic alcohol containing 90% or more of a saturated aliphatic alcohol having 9 carbon atoms wherein the ratio of the linear-chain saturated aliphatic alcohol is from 50 to 99% (trinonyl trimellitate (branched and linear chain), TL9TM); pyromellitic acid esters (e.g. tetra-2-ethylhexyl pyromellitate (TOPM), etc.); phosphoric acid esters (e.g. tri-2-ethylhexyl phosphate (TOP), tricresyl phosphate (TCP), etc.); alkyl esters of polyhydric alcohols such as pentaerythritol; polyesters having a molecular weight of from 800 to 4000 synthesized by polyesterification of a dibasic acid (e.g. adipic acid, etc.) and a glycol; polyethers; epoxidized esters (e.g. epoxidized soybean oil, epoxidized linseed oil, etc.); fatty acid glycol esters (e.g. 1,4-butanediol dicaprate, etc.); citric acid esters (e.g. acetyl tributyl citrate (ATBC), acetyl trihexyl citrate (ATHC), acetyl triethylhexyl citrate (ATEHC), butyryl trihexyl citrate (BTHC), etc.); isosorbide diesters; chlorinated paraffins obtained by chlorinating paraffin wax or n-paraffin; chlorinated fatty acid esters (e.g. chlorinated stearic acid ester, etc.); higher fatty acid esters (e.g. butyl oleate, etc.); and the like. In the case of blending other plasticizers that can be used in combination, the blending amount is appropriately selected within the range not to impair the effect of the plasticizer of the present invention, and is recommended to be usually about 1 to 100 parts by weight with respect to 100 parts by weight of the vinyl chloride-based resin.

Examples of the flame retardant include inorganic compounds such as aluminum hydroxide, antimony trioxide, magnesium hydroxide, and zinc borate; phosphorus compounds such as cresyl diphenyl phosphate, trischloroethyl phosphate, trischloropropyl phosphate, and trisdichloropropyl phosphate; halogen compounds such as chlorinated paraffin, and the like. When the flame retardant is blended, the blending amount is recommended to be about 0.1 to 20 parts by weight with respect to 100 parts by weight of the vinyl chloride-based resin.

Examples of the stabilizer include metal soap compounds of an organic acid compound containing a metal, such as lithium stearate, magnesium stearate, magnesium laurate, calcium ricinoleate, calcium stearate, barium laurate, barium ricinoleate, barium stearate, zinc octoate, zinc laurate, zinc ricinoleate, and zinc stearate; metal soap compounds of an organic acid compound containing a composite metal, such as barium-zinc stearate, barium-zinc laurate, barium-zinc ricinoleate, barium-zinc octoate, calcium-zinc stearate, calcium-zinc laurate, calcium-zinc ricinoleate, and calcium-zinc octoate; organotin-based compounds such as dimethyltin bis(2-ethylhexyl thioglycolate), dibutyltin maleate, dibutyltin bis(butyl maleate), and dibutyltin dilaurate; antimony mercaptide compounds; epoxy compounds other than the present diester, such as epoxidized soybean oil, epoxidized linseed oil, and epoxy resin; and the like. When the stabilizer is blended, the blending amount is recommended to be about 0.1 to 20 parts by weight with respect to 100 parts by weight of the vinyl chloride-based resin.

Examples of the stabilizing aid include phosphite-based compounds such as triphenyl phosphite, monooctyl diphenyl phosphite, and tridecyl phosphite; beta-diketone compounds such as acetylacetone and benzoylacetone; polyol compounds such as glycerin, sorbitol, pentaerythritol, and polyethylene glycol; perchlorate compounds such as barium perchlorate and sodium perchlorate; hydrotalcite compounds; zeolites; and the like. When a stabilizing aid is blended, the blending amount is recommended to be about 0.1 to 20 parts by weight with respect to 100 parts by weight of the vinyl chloride-based resin.

Examples of the coloring agent include carbon black, lead sulfide, white carbon, titanium white, lithopone, red oxide, antimony sulfide, chrome yellow, chrome green, phthalocyanine green, cobalt blue, phthalocyanine blue, and molybdenum orange. When a coloring agent is blended, the blending amount is recommended to be about from 1 to 100 parts by weight per 100 parts by weight of the vinyl chloride-based resin.

Examples of the processing aid include liquid paraffin, polyethylene wax, stearic acid, stearic acid amide, ethylene bis(stearic acid amide), butyl stearate, and calcium stearate. When a processing aid is blended, the blending amount is recommended to be about from 0.1 to 20 parts by weight with respect to 100 parts by weight of the vinyl chloride-based resin.

Examples of the filler include metal oxides such as calcium carbonate, silica, alumina, clay, talc, diatomaceous earth, and ferrite; fibers and powders of glass, carbon, metal, or the like; glass beads; graphite; aluminum hydroxide; barium sulfate; magnesium oxide; magnesium carbonate; magnesium silicate; calcium silicate; and the like. When a filler is blended, the blending amount is recommended to be about from 1 to 100 parts by weight with respect to 100 parts by weight of the vinyl chloride-based resin.

Examples of the antioxidant include phenol-based compounds (e.g. 2,6-di-tert-butylphenol, tetrakis[methylene-3-(3,5-tert-butyl-4-hydroxyphenol) propionate]methane, 2-hydroxy-4-methoxybenzophenone, etc.); sulfur compounds (e.g. alkyl disulfides, thiodipropionate esters, benzothiazoles, etc.); phosphate-based compounds (e.g. tris(nonylphenyl) phosphite, diphenyl isodecyl phosphite, triphenyl phosphite, tris(2,4-di-t-butylphenyl) phosphite, etc.); organometallic compounds (e.g. zinc dialkyl dithiophosphate, zinc diaryl dithiophosphate, etc.); and the like. When an antioxidant is blended, the blending amount is recommended to be about from 0.2 to 20 parts by weight with respect to 100 parts by weight of the vinyl chloride-based resin.

Examples of the ultraviolet absorber include salicylate-based compounds such as phenyl salicylate and p-tert-butylphenyl salicylate; benzophenone-based compounds such as 2-hydroxy-4-n-octoxybenzophenone and 2-hydroxy-4-methoxybenzophenone; benzotriazole-based compounds such as 5-methyl-1H-benzotriazole, 1-dioctylaminomethyl-benzotriazole; cyanoacrylate-based compounds; and the like. When an ultraviolet absorber is blended, the blending amount is recommended to be about from 0.1 to 10 parts by weight with respect to 100 parts by weight of the vinyl chloride-based resin.

Examples of the hindered amine-based light stabilizer include bis(2,2,6,6-tetramethyl-4-piperidyl) sebacate, bis(1,2,2,6,6-pentamethyl-4-piperidyl) sebacate and 1,2,2,6,6-pentamethyl-4-piperidyl sebacate (mixture), bis(1,2,2,6,6-pentamethyl-4-piperidyl) [[3,5-bis(1,1-dimethylethyl)-4-hydroxyphenyl]methyl]butyl malonate, decanedioic acid bis (2,2,6,6-tetramethyl-1(octyloxy)-4-piperidyl)ester, and a reaction product of 1,1-dimethylethyl hydroperoxide and octane, 4-benzoyloxy-2,2,6,6-tetramethylpiperidine, an ester mixture of 2,2,6,6-tetramethyl-4-piperidinol and a higher fatty acid, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, a polycondensation product of dimethyl succinate and 4-hydroxy-2,2,6,6-tetramethyl-1-piperidine ethanol, poly[{(6-(1,1,3,3-tetramethylbutyl)amino-1,3,5-triazine-2,4-diyl}{(2,2,6,6-tetramethyl-4-piperidyl)imino)hexamethylene {(2,2,6,6-tetramethyl-4-piperidyl)imino}}, a polycondensation product of dibutylamine/1,3,5-triazine/N,N'-bis(2,2,6,6-tetramethyl-4-piperidyl-1,6-hexamethylenediamine and N-(2,2,6,6-tetramethyl-4-piperidyl)butylamine, N,N',N'',N'''-tetrakis-(4,6-bis-(butyl-(N-methyl-2,2,6,6-tetramethylpiperidine-4-yl)amino)-triazine-2-yl)-4,7-diazadecane-1,10-diamine, and the like. When a light stabilizer is blended, the blending amount is recommended to be about from 0.1 to 10 parts by weight with respect to 100 parts by weight of the vinyl chloride-based resin.

Examples of the lubricant include silicone; liquid paraffin; paraffin wax; fatty acid metal salts such as metal stearate and metal laurate; fatty acid amide; fatty acid wax; and higher fatty acid wax. When a lubricant is blended, the blending amount is recommended to be about from 0.1 to 10 parts by weight with respect to 100 parts by weight of the vinyl chloride-based resin.

Examples of the antistatic agent include anionic antistatic agents such as alkyl sulfonate antistatic agents, alkyl ether carboxylic acid antistatic agents, or dialkyl sulfosuccinate antistatic agents; nonionic antistatic agents such as polyethylene glycol derivatives, sorbitan derivatives or diethanolamine derivatives; quaternary ammonium salts such as alkylamide amine antistatic agents or alkyl dimethylbenzyl antistatic agents; cationic antistatic agents such as alkyl pyridinium organic acid salt or hydrochloride; and amphoteric antistatic agents such as alkylbetaine antistatic agents or alkylimidazoline antistatic agents. When an antistatic agent is blended, the blending amount is recommended to be about from 0.1 to 10 parts by weight with respect to 100 parts by weight of the vinyl chloride-based resin.

The vinyl chloride-based resin composition or the soft vinyl chloride-based resin composition of the present invention can be converted into a mixed powder by mixing and stirring the present diester, the vinyl chloride-based resin, and if necessary, various additives, using a stirrer such as a mortar mixer, a Henschel mixer, a Banbury mixer, or a ribbon blender.

The present diester, the vinyl chloride-based resin, and if necessary, various additives can be subjected to melt molding using a kneading machine such as a conical twin screw extruder, a parallel twin screw extruder, a single screw extruder, a co-kneader type kneading machine, a roll kneader, etc, thereby to obtain a pellet form of the vinyl chloride-based resin composition or the soft vinyl chloride-based resin composition.

In addition, the present diester, a vinyl chloride-based paste resin, and if necessary, other plasticizers other than the present diester, and various additives are mixed homogeneously by a pony mixer, a butterfly mixer, a planetary mixer, a ribbon blender, a kneader, a dissolver, a twin screw mixer, a Henschel mixer, a triple roll mill, and the like, and defoaming treatment is optionally carried out under reduced pressure to be able to obtain a pasty soft vinyl chloride-based resin composition.

[Vinyl Chloride-Based Molded Body]

The vinyl chloride-based resin composition or the soft vinyl chloride-based resin composition (powder formulation or pellet formulation) according to the present invention can be molded into a desired shape by melt-molding using a conventionally known method such as vacuum molding, compression molding, extrusion molding, injection molding, calender molding, press molding, blow molding, and powder molding.

On the other hand, the pasty soft vinyl chloride-based resin composition can be formed into a desired shape by molding processing using a conventionally known method such as spread molding, dipping molding, gravure molding, slush molding, and screen processing.

The shape of the molded body is not particularly limited, and examples thereof include rod shape, sheet shape, film shape, plate shape, cylindrical shape, round shape, elliptical shape, or particular shapes of toys, ornaments, and the like (for example, star shape or polygon shape).

<Chlorine-Containing Resin Composition>

The stabilized chlorine-containing resin composition of the present invention is obtained by blending the present diester as a stabilizer into a chlorine-containing resin.

[Chlorine-Containing Resin]

The chlorine-containing resin used in the present invention is not particularly limited as long as it is a resin containing chlorine in the structure thereof, and examples thereof include homopolymers such as polyvinyl chloride, polyvinylidene chloride, chlorinated polyolefins (e.g. chlorinated polyethylene, chlorinated polypropylene), chlorinated polyvinyl chloride, and further copolymers such as vinyl chloride-ethylene copolymer, vinyl chloride-propylene copolymer, vinyl chloride-vinyl acetate copolymer, vinyl chloride-styrene copolymer, vinyl chloride-isobutylene copolymer, vinyl chloride-butadiene copolymer, vinyl chloride-vinylidene chloride copolymer, vinyl chloride-chlorinated propylene copolymer, vinyl chloride-maleic acid ester copolymer, allyl chloride copolymer, vinyl chloride-methacrylic acid ester copolymer, ethylene-vinyl acetate-vinyl chloride copolymer, vinyl chloride-styrene-maleic anhydride terpolymer, vinyl chloride-styrene-acrylonitrile copolymer, vinyl chloride-isoprene copolymer, vinyl chloride-vinylidene chloride-vinyl acetate terpolymer, vinyl chloride-acrylonitrile copolymer, and vinyl chloride-various vinyl ethers copolymer.

The stabilizer according to the present invention can also be used in a system of chloroprene-based synthetic rubber, epichlorohydrin rubber and copolymer thereof, and a chlorine-containing rubber or elastomer such as hydrochloric acid rubber and chlorinated rubber.

The chlorine-containing resin may be a single type or a blend type with another compatible resin, for example, with a resin such as polyester resin, acrylic resin, urethane resin, and acrylonitrile-styrene-butadiene copolymer.

Among them, the vinyl chloride-based resin is a chlorine-containing resin that is easy to process, excellent in characteristics of the obtained molded body, and is widely used.

Since the vinyl chloride-based resin is as described above, its explanation will be omitted.

[Chlorine-Containing Resin Composition]

The content of the present diester in the stabilized chlorine-containing resin composition according to the present invention is appropriately selected depending on the type of the resin to be blended and the application to be used, but the content is preferably from 1 to 30 parts by weight, more preferably from 1 part by weight or more but less than 20 parts by weight, particularly preferably 5 parts by weight or more but less than 20 parts by weight, with respect to 100 parts by weight of the chlorine-containing resin. If the content is 1 part by weight or more, it is possible to obtain a more favorable stabilizing effect, and such a content is advantageous particularly in view of long-term stabilizing effect. If the content is 30 parts by weight or less, there are less concerns about various problems such as bleeding to the surface of the molded article even in any use environment, migration to the laminated resin or to the oil to be contacted, and furthermore the occurrence of fogging due to volatilization, and thus the content in the above range of the present diester is preferred.

For the chlorine-containing resin composition, other known stabilizers may be used in combination with the present diester. Further, if necessary, additives such as a stabilizing aid, an antioxidant (an aging inhibitor), an ultraviolet absorber, a light stabilizer such as a hindered amine, a plasticizer, a flame retardant, a coloring agent, a processing aid, a filler, a lubricant or an antistatic agent is appropriately blended and frequently used.

Other stabilizers other than the present diesters, and additives may be blended singly or in combination of two or more kinds thereof together with the present diester.

As the stabilizer that can be used in combination with the present diester, the above-mentioned ones are exemplified. Among them, the combined use of the metal soap compound shows an effect of amplifying the stabilizing effect of the present diester due to a synergistic effect, so that such combination use is particularly preferable. In the case of blending other stabilizers that can be used in combination, the blending amount thereof is appropriately selected within the range not to impair the effect of the stabilizing agent according to the present invention, and is usually recommended to use about 0.1 to 20 parts by weight with respect to 100 parts by weight of the chlorine-containing resin.

Combination use of a stabilizing aid is also effective as a method of making the effect of the present diester more effective. As the stabilizing aid, the above-mentioned ones are exemplified. When a stabilizing aid is blended, the blending amount is appropriately selected within the range not to impair the effect of the stabilizing agent of the present invention, and is usually recommended to use about 0.1 to 20 parts by weight with respect to 100 parts by weight of the chlorine-containing resin.

It is also effective as a method of making the effect of the present diester more effective to use an antioxidant, an ultraviolet absorber antioxidant, a light stabilizer and the like in combination with the present diester. As the antioxidant, the above-mentioned ones are exemplified. When blending an antioxidant, the blending amount is recommended to be about 0.2 to 20 parts by weight with respect to 100 parts by weight of the chlorine-containing resin.

As the ultraviolet absorber, the above-mentioned ones are exemplified. When blending an ultraviolet absorber, the blending amount is recommended to be about 0.1 to 10 parts by weight with respect to 100 parts by weight of the chlorine-containing resin.

As the hindered amine-based light stabilizer, the above-mentioned ones are exemplified. When blending a light stabilizer, the blending amount is recommended to be about 0.1 to 10 parts by weight with respect to 100 parts by weight of the chlorine-containing resin.

As the plasticizer, known plasticizers that have been conventionally used can be used, and the above-mentioned ones are exemplified.

Among them, there are exemplified aromatic polycarboxylic acid esters such as phthalic acid esters and trimellitic acid esters; alicyclic polycarboxylic acid esters such as alicyclic dibasic acid esters; polyesters; polyethers; and the like. More specifically, phthalic acid esters, trimellitic acid esters, cyclohexanedicarboxylic acid esters and the like are exemplified as particularly preferable plasticizers. Specific examples of the preferable plasticizer include diisodecyl phthalate (DIDP), di(2-propylheptyl) phthalate (DPHP), diundecyl phthalate, dialkyl(C9 to C11) phthalate (PL-200), dialkyl(C10 to C13) phthalate (VINYCIZER 124), ditridecyl phthalate (VINYCIZER 20), tri-2-ethylhexyl trimellitate (TOTM), tri-n-octyl trimellitate (TRIMEX New NSK), tri-isonyl trimellitate (TINTM), triisodecyl trimellitate (TIDTM), tri-n-alkyl(C8, C10) trimellitate (TRIMEX N-08), trinonyl trinellitate (branched and linear chain) (TL9TM), and the like.

In the case where the plasticizer is contained, its content is appropriately selected according to the hardness required for the application to be used, but 1 to 200 parts by weight, preferably about 5 to 150 parts by weight, with respect to 100 parts by weight of the chlorine-containing resin is usually recommended.

The stabilizer for chlorine-containing resins according to the present invention and the plasticizer may be separately added to the chlorine-containing resin, but it is more preferable to add them after mixing in advance, to the chlorine-containing resin. By premixing, compatibilization of a plasticizer having poor compatibility with a resin (that is, an addition effect of improving plasticization efficiency of the plasticizer having poor plasticization efficiency), or improvement in the uniformity of the stabilizer in the resin when the content of the stabilizer is small, that is, an effect of preventing unevenness of stabilizing effect of the stabilizer and the like is expected.

As the flame retardant, the above-mentioned ones are exemplified. When blending a flame retardant, the blending amount is recommended to be about 0.1 to 20 parts by weight with respect to 100 parts by weight of the chlorine-containing resin.

As the coloring agent, the above-mentioned ones are exemplified. When blending a coloring agent, the blending amount is recommended to be about 1 to 100 parts by weight with respect to 100 parts by weight of the chlorine-containing resin.

As the processing aid, the above-mentioned ones are exemplified. When blending a processing aid, the blending amount is recommended to be about 0.1 to 20 parts by weight with respect to 100 parts by weight of the chlorine-containing resin.

As the filler, the above-mentioned ones are exemplified. When blending a filler, the blending amount is recommended to be about 1 to 100 parts by weight with respect to 100 parts by weight of the chlorine-containing resin.

As the lubricant, the above-mentioned ones are exemplified. When blending a lubricant, the blending amount is recommended to be about 0.1 to 10 parts by weight with respect to 100 parts by weight of the chlorine-containing resin.

As the antistatic agent, the above-mentioned ones are exemplified. When blending an antistatic agent, the blending amount is recommended to be about 0.1 to 10 parts by weight with respect to 100 parts by weight of the chlorine-containing resin.

The chlorine-containing resin composition of the present invention can be converted into a mixed powder by stirring and mixing the present diester, the chlorine-containing resin, and if necessary, various additives, using a stirrer such as a mortar mixer, a Henschel mixer, a Banbury mixer, and a ribbon blender.

The present diester, a chlorine-containing resin, and if necessary, various additives can be subjected to melt molding with use of a kneader such as a conical twin screw extruder, a parallel twin-screw extruder, a single screw extruder, a co-kneader type kneading machine, and a roll kneader, so that a pelletized chlorine-containing resin composition can be obtained.

In addition, the present diester, a plasticizer, a vinyl chloride-based paste resin, and if necessary, various additives are mixed homogeneously by a mixer such as a pony mixer, a butterfly mixer, a planetary mixer, a ribbon blender, a kneader, a dissolver, a twin screw mixer, a Henschel mixer, a triple roll mill, and the like, and defoaming treatment is optionally carried out under reduced pressure to be able to obtain a pasty vinyl chloride-based resin composition.

[Chlorine-Containing Resin Molded Body]

The chlorine-containing resin composition (powder formulation or pellet formulation) can be molded into a desired shape by melt-molding processing using a conventionally known method such as vacuum molding, compression molding, extrusion molding, injection molding, calender molding, press molding, blow molding, and powder molding.

On the other hand, the pasty chlorine-containing resin composition can be formed into a desired shape by molding processing using a conventionally known method such as spread molding, dipping molding, gravure molding, slush molding, and screen processing.

The shape of the molded body is not particularly limited, and examples thereof include rod shape, sheet shape, film shape, plate shape, cylindrical shape, round shape, elliptical shape; and particular shapes of toys, ornaments, and the like, such as star shape or polygon shape.

<Vinyl Chloride-Based Resin Composition for Automotive Interior>

The greatest feature of the vinyl chloride-based resin composition for automotive interior of the present invention resides in that the resin contains the above-mentioned diester as a plasticizing component (plasticizer) or a stabilizing component (stabilizer), and such composition can be obtained by blending the present diester as a plasticizer or as a stabilizer with a vinyl chloride-based resin.

[Vinyl Chloride-Based Resin]

Since the vinyl chloride-based resin used in the present invention is as described above, its explanation will be omitted.

[Vinyl Chloride-Based Resin Composition for Automotive Interior]

The content of the present diester in the vinyl chloride-based resin composition for automotive interior of the present invention is appropriately selected according to its use, but is preferably from 1 to 200 parts by weight, more preferably 5 to 150 parts by weight, with respect to 100 parts by weight of the vinyl chloride-based resin. The present diester has also an effect as a plasticizer as well as an effect as a stabilizer regardless of its blending amount. More specifically, when an effect as a plasticizer is desired, the blending amount is preferably from 20 to 200 parts by weight, more preferably from 30 to 150 parts by weight. When a stabilizer effect is mainly desired, the blending amount as a stabilizer is preferably from 1 to 30 parts by weight, more preferably from 5 to 20 parts by weight.

When the content of the present diester is 1 part by weight or more with respect to 100 parts by weight of the vinyl chloride-based resin, the effect as the stabilizer of the present diester can be sufficiently exerted, and if the content of the present diester is 200 parts by weight or less, there is no concern about bleeding to the surface of the molded article when used. Thus, such molded article can be used with confidence.

In addition, when the present diester is desired to have an effect as a plasticizer, sufficient flexibility can be obtained according to the purpose of use if the content is 20 parts by weight or more with respect to 100 parts by weight of the vinyl chloride-based resin.

Further, in the case where an effect as a stabilizer (stabilizing effect) is mainly desired, if the content is 1 part by weight or more with respect to 100 parts by weight of the vinyl chloride-based resin, sufficient stabilizing effect, especially long-term stabilization effect can be obtained. In addition, if the content is 30 parts by weight or less, the stabilizing effect becomes dominant over the effect as a plasticizer, so that it is also possible to maintain the target hardness for inherently intended use without becoming soft.

For the vinyl chloride-based resin composition for automotive interior material according to the present invention, other known plasticizers or stabilizers can be used in combination with the present diester, and such combination use is recommended from the viewpoint of plasticizing effect and stabilizing effect. From the viewpoint of the stabilizing effect, it is also recommended that if necessary, a stabilizing aid, an antioxidant (an aging inhibitor), an ultraviolet absorber, a light stabilizer such as a hindered amine, and the like be used in combination. Further, in many cases, additives such as a flame retardant, a coloring agent, a processing aid, a filler, a lubricant, or an antistatic agent are appropriately blended and used frequently according to the intended use.

Other plasticizers and stabilizers except for the present diester, and other additives may be blended singly or in combination of two or more kinds thereof together with the present diester.

As other plasticizers that can be used in combination with the present diester, known plasticizers conventionally used in the state of the art can be used, and include the above-mentioned ones. In the case of blending other plasticizer that can be used in combination, the blending amount is appropriately selected within the range not to impair the effect of the plasticizer according to the present invention, and about 1 to 100 parts by weight with respect to 100 parts by weight of the vinyl chloride-based resin is usually recommended.

Among them, aromatic polycarboxylic acid esters such as phthalic acid esters and trimellitic acid esters; alicyclic polycarboxylic acid esters such as alicyclic dibasic acid esters; polyesters; and polyethers are exemplified as preferable plasticizers. Further, phthalic acid esters, trimellitic acid esters, cyclohexane dicarboxylic acid esters and the like are exemplified as particularly preferable plasticizers. Specific examples of the particularly preferable plasticizers include diisodecyl phthalate (DIDP), di(2-propylheptyl) phthalate (DPHP), diundecyl phthalate, dialkyl(C9 to C11) phthalate (PL-200), dialkyl(C10 to C13) phthalate (VINYCIZER 124), ditridecyl phthalate (VINYCIZER 20), tri-2-ethylhexyl trimellitate (TOTM), tri-n-octyl trimellitate (TRIMEX New NSK), triisonyl trimellitate (TINTM), triisodecyl trimellitate (TIDTM), tri-n-alkyl(C8, C10) trimellitate (TRIMEX N-08), a trimellitic acid triester of a saturated aliphatic alcohol containing 90% or more of a saturated aliphatic alcohol having 9 carbon atoms and having a ratio of linear-chain saturated aliphatic alcohol of from 50 to 99% (trinonyl trimellitate (branched and linear chain), TL9TM), and the like.

When the plasticizer is used in combination, the content thereof is appropriately selected according to the hardness required for the intended use, but the recommended blending content is usually from 1 to 200 parts by weight, preferably 5 to 150 parts by weight, with respect to 100 parts by weight of the vinyl chloride-based resin.

The present diester and the plasticizer according to the present invention may be separately added to the vinyl chloride-based resin, but it is more preferable to add the present diester and the plasticizer to the vinyl chloride-based resin after mixing together in advance. By premixing, it becomes easy to obtain a compatibilization effect of the plasticizer having poor compatibility with the resin (that is, a plasticizer having poor plasticization efficiency), namely to obtain an improving effect of plasticization efficiency, or it becomes easy to obtain a preventive effect of unevenness in the stabilizing effect of the stabilizer as a result of maintaining the uniformity in the resin when the present diester is used as the stabilizer even if the content is small.

As the stabilizer that can be used in combination with the present diester, the above-mentioned ones are exemplified. Among them, the combination use of the above-mentioned metal soap compound shows an effect of amplifying the stabilizing effect of the present diester due to a synergistic effect, and is therefore particularly preferable. In the case of blending other stabilizer that can be used in combination, the blending amount is appropriately selected within the range not to impair the effect of the stabilizer of the present invention, and about 0.1 to 20 parts by weight is usually recommended with respect to 100 parts by weight of the vinyl chloride-based resin.

Combination use of a stabilizing aid is also effective as a method of making the effect of the present diester more effective. As the stabilizing aid, the above-mentioned ones are exemplified. When a stabilizing aid is blended, the blending amount is appropriately selected within the range not to impair the effect of the stabilizer according to the present invention, and about 0.1 to 20 parts by weight is usually recommended with respect to 100 parts by weight of the vinyl chloride-based resin.

Combination use of an antioxidant, an ultraviolet absorber antioxidant, a light stabilizer, and the like is also effective as a method of making the effect of the present diester more effective. As the antioxidant, the above-mentioned ones are exemplified. When an antioxidant is blended, the blending amount is recommended to be about 0.2 to 20 parts by weight with respect to 100 parts by weight of the vinyl chloride-based resin.

As the ultraviolet absorber, the above-mentioned ones are exemplified. When blending an ultraviolet absorber, the blending amount is recommended to be about 0.1 to 10 parts by weight with respect to 100 parts by weight of the vinyl chloride-based resin.

As the hindered amine-based light stabilizer, the above-mentioned ones are exemplified. When blending a light stabilizer, the blending amount is recommended to be about 0.1 to 10 parts by weight with respect to 100 parts by weight of the vinyl chloride-based resin.

As the flame retardant, the above-mentioned ones are exemplified. When blending a flame retardant, the blending amount is recommended to be about 0.1 to 20 parts by weight with respect to 100 parts by weight of the vinyl chloride-based resin.

As the coloring agent, the above-mentioned ones are exemplified. When blending a coloring agent, the blending amount is recommended to be about 1 to 100 parts by weight with respect to 100 parts by weight of the vinyl chloride-based resin.

As the processing aid, the above-mentioned ones are exemplified. When blending a processing aid, the blending amount is recommended to be about 0.1 to 20 parts by weight with respect to 100 parts by weight of the vinyl chloride-based resin.

As the filler, the above-mentioned ones are exemplified. When blending a filler, the blending amount is recommended to be about 1 to 100 parts by weight with respect to 100 parts by weight of the vinyl chloride-based resin.

As the lubricant, the above-mentioned ones are exemplified. When blending a lubricant, the blending amount is recommended to be about 0.1 to 10 parts by weight with respect to 100 parts by weight of the vinyl chloride-based resin.

As the antistatic agent, the above-mentioned ones are exemplified. When blending an antistatic agent, the blending amount is recommended to be about 0.1 to 10 parts by weight with respect to 100 parts by weight of the vinyl chloride-based resin.

The vinyl chloride-based resin composition for automotive interior materials of the present invention can be converted into a mixed powder of the vinyl chloride-based resin composition for automotive interior materials by stirring and mixing the present diester, the vinyl chloride-based resin, and various additives as needed, using a stirrer such as a mortar mixer, a Henschel mixer, a Banbury mixer, and a ribbon blender.

The present diester, a vinyl chloride-based resin, and if necessary, various additives can be melt-molded into a pelletized vinyl chloride-based resin composition for automotive interior by a kneading machine such as a conical twin-screw extruder, a parallel twin-screw extruder, a single screw extruder, a co-kneader kneading machine, and a roll kneader.

Further, the present diester, a pasty vinyl chloride-based resin, and if necessary, various additives can be mixed homogenously with each other by a mixer such as a pony mixer, a butterfly mixer, a planetary mixer, a ribbon blender, a kneader, a dissolver, a twin screw mixer, a Henschel mixer, and a triple roll mill, and defoaming treatment is optionally carried out under reduced pressure to be able to obtain a pasty vinyl chloride-based resin composition for automotive interior.

[Automotive Interior Material]

The vinyl chloride-based resin composition (powder formulation or pellet formulation) for automotive interiors according to the present invention can be melt-molded into a desired shape of an automotive interior material by using a conventionally known method such as vacuum molding, compression molding, extrusion molding, injection molding, calender molding, press molding, blow molding, and powder molding.

On the other hand, the above pasty vinyl chloride-based resin composition for automotive interior can be molded into a desired shape of an automotive interior material by using a conventionally known method such as spread molding, dipping molding, gravure molding, slush molding, and screen processing.

The automotive interior material thus obtained can be suitably used as an interior material for automobiles, such as instrument panel, door trim, trunk trim, seat sheet, pillar cover, ceiling material, rear tray, console box, airbag cover, armrest, headrest, meter cover, crash pad, and floor carpet.

<Medical Vinyl Chloride-Based Resin Composition>

The greatest feature of the vinyl chloride-based resin composition of the present invention resides in that it contains the present diester as a plasticizing component (plasticizer) or a stabilizing component (stabilizer), and the vinyl chloride-based resin composition can be obtained by blending the present diester with a vinyl chloride-based resin.

[Vinyl Chloride-Based Resin]

Since the vinyl chloride-based resin used in the present invention is as described above, its explanation will be omitted.

[Medical Vinyl Chloride-Based Resin Composition]

The content of the present diester in the medical vinyl chloride-based resin composition of the present invention is appropriately selected according to the applications, but the content of the present diester is usually 5 to 200 parts by weight, preferably 5 to 100 parts by weight, with respect to 100 parts by weight of the vinyl chloride-based resin. Even when the content of the present diester is in the above range, the content of the present diester is recommended to be preferably in the range of 30 to 200 parts by weight, more preferably in the range of 30 to 150 parts by weight, particularly preferably in the range of 40 to 100 parts by weight, depending on the method of use (application) of the medical vinyl chloride-based resin composition of the present invention, for example, in the case of the composition used as a soft material. When the medical vinyl chloride-based resin composition is used as a semi-hard material, the recommended content of the present diester is preferably in the range of 5 parts by weight or more but less than 30 parts by weight, more preferably in the range of 5 parts by weight or more but less than 20 parts by weight. If the content of the present diester is less than 5 parts by weight, the mechanical properties and the deterioration preventing effect at the time of sterilization and disinfection may be insufficient in some cases. When the present diester is added in an amount exceeding 200 parts by weight, bleeding to the surface of the molded article is severe. Both cases may be undesirable. When a filler or the like is added to the vinyl chloride-based resin composition, the filler itself absorbs oil, so that the present diester can be added beyond the above-mentioned range. For example, when 100 parts by weight of calcium carbonate is blended as a filler with respect to 100 parts by weight of the vinyl chloride-based resin, the plasticizer may be blended in an amount of about 5 to 500 parts by weight.

In order to much more suppress deterioration after sterilization and disinfection treatment, inclusion of only the present diester may be sufficient for such purpose, but further inclusion of a stabilizer such as a metal soap compound and a radiation-resistant material of a silane compound type is much better for such suppression.

As the stabilizer, the above-mentioned ones are exemplified. When blending a stabilizer, the blending amount is recommended to be about 0.1 to 20 parts by weight with respect to 100 parts by weight of the vinyl chloride-based resin. The metal soap compound may exert a function as a processing aid or as a lubricant together with a function as a stabilizer in some cases.

Among the stabilizers, a combination of calcium stearate and zinc stearate is most preferably used from the viewpoint of safety and the like. Further, the total blending amount is recommended to be about 0.1 to 10 parts by weight, preferably about 0.2 to 6 parts by weight, and the blending ratio is not particularly limited as long as such blending ratio is in a range capable of showing a stabilization effect, but such combination is usually used in the range of 5:1 to 1:5 in many cases.

Examples of the silane compound-based radiation-resistant material include monoalkoxysilane compounds such as trimethylmethoxysilane, trimethylethoxysilane, triethylmethoxysilane, and triethylethoxysilane; dialkoxysilane compounds such as dimethyldimethoxysilane, diethyldimethoxysilane, dimethyldiethoxysilane, diphenyldimethoxysilane, diphenyldiethoxysilane, methylaminoethoxypropyldialkoxysilane, N-(β-aminoethyl)-α-aminopropylmethyldimethoxysilane, γ-glycidoxypropylmethyldimethoxysilane, and γ-methacryloxypropylmethyldimethoxysilane; trialkoxysilane compounds such as methyltrimethoxysilane, methyltriethoxysilane, hexyltrimethoxysilane, phenyltrimethoxysilane, phenyltriethoxysilane, vinyltrimethoxysilane, vinyltriethoxysilane, γ-chloropropyltrimethoxysilane, γ-aminopropyltriethoxysilane, N-(β-aminoethyl)-γ-aminopropyltrimethoxysilane, N-(phenyl)-γ-aminopropyltrimethoxysilane, γ-glycidoxypropyltrimethoxysilane, 3-methacryloxypropyltrimethoxysilane, 3-methacryloxypropyltriethoxysilane, γ-mercaptopropyltrimethoxysilane, γ-(polyethyleneamino)propyltrimethoxysilane, γ-ureidopropyltriethoxysilane, heptadecafluorodecyltrimethoxysilane, tridecafluorooctyltrimethoxysilane, vinyltris(β-methoxyethoxy)silane, and β-(3,4-epoxycyclohexyl)ethyltrimethoxysilane; tetraalkoxysilane compounds such as tetramethoxysilane and tetraethoxysilane; acetoxysilane compounds such as vinyltriacetoxysilane; chlorosilane compounds such as trimethylchlorosilane, dimethyldichlorosilane, methyltrichlorosilane, vinyltrichlorosilane, and γ-chloropropylmethyldichlorosilane; organosilane compounds such as triisopropylsilane, triisopropylsilyl acrylate, allyltrimethylsilane, and methyl trimethylsilylacetate; and the like. When blending a radiation resistant material, the blending amount is recommended to be about 0.1 to 15 parts by weight with respect to 100 parts by weight of the vinyl chloride-based resin.

In the medical vinyl chloride-based resin composition of the present invention, other known plasticizers can be used together with the present diester. In addition, it is also possible to blend, if necessary, additives such as stabilizing aid, antioxidants (aging inhibitors), ultraviolet absorbers, hindered amine-based light stabilizers, fillers, diluents, viscosity reducing agents, thickeners, processing aids, lubricants, antistatic agents, flame retardants, foaming agents, adhesives, and coloring agents.

Other plasticizers other than the above diester, and additives may be blended singly or in combination of two or more kinds thereof in appropriate combination with the present diester.

As the known plasticizer that can be used in combination with the present diester, the above-mentioned ones are exemplified. When blending a plasticizer that can be used in combination, the blending amount is recommended to be about 1 to 100 parts by weight with respect to 100 parts by weight of the vinyl chloride-based resin.

As the stabilizing aid, the above-mentioned ones are exemplified. When blending a stabilizing aid, the blending amount is recommended to be about 0.1 to 20 parts by weight with respect to 100 parts by weight of the vinyl chloride-based resin.

As the antioxidant, the above-mentioned ones are exemplified. When blending an antioxidant, the blending amount is recommended to be about 0.2 to 20 parts by weight with respect to 100 parts by weight of the vinyl chloride-based resin.

As the ultraviolet absorber, the above-mentioned ones are exemplified. When blending an ultraviolet absorber, the blending amount is recommended to be about 0.1 to 10 parts by weight with respect to 100 parts by weight of the vinyl chloride-based resin.

As the hindered amine-based light stabilizer, the above-mentioned ones are exemplified. When blending a light stabilizer, the blending amount is recommended to be about 0.1 to 10 parts by weight with respect to 100 parts by weight of the vinyl chloride-based resin.

As the filler, the above-mentioned ones are exemplified. When blending a filler, the blending amount is recommended to be about 1 to 100 parts by weight with respect to 100 parts by weight of the vinyl chloride-based resin.

Examples of the diluent include 2,2,4-trimethyl-1,3-pentanediol diisobutyrate, and aliphatic or aromatic hydrocarbons having a low boiling point. When blending a diluent, the blending amount is recommended to be about 1 to 50 parts by weight with respect to 100 parts by weight of the vinyl chloride-based resin.

Examples of the viscosity reducing agent include various non-ionic surfactants, sulfosuccinate-based anionic surfactants, silicone-based compounds having surface activity, soybean oil lecithin, monohydric alcohols, glycol ethers, polyethylene glycols, and the like. When blending a viscosity reducing agent, the blending amount is recommended to be about 0.1 to 20 parts by weight with respect to 100 parts by weight of the vinyl chloride-based resin.

Examples of the thickener include synthetic fine powder silica-based thickeners, bentonite-based thickeners, superfine precipitated calcium carbonates, metal soap-based thickeners, hydrogenated castor oil, polyamide wax, polyethylene oxide-based thickeners, vegetable oil-based thickeners, sulfate-based surfactants, non-ionic surfactants, and the like. When blending a thickener, the blending amount is recommended to be about 1 to 50 parts by weight with respect to 100 parts by weight of the vinyl chloride-based resin.

As the processing aid, the above-mentioned ones are exemplified. When blending a processing aid, the blending amount is recommended to be about 0.1 to 20 parts by weight with respect to 100 parts by weight of the vinyl chloride-based resin.

As the lubricant, the above-mentioned ones are exemplified. When blending a lubricant is, the blending amount is recommended to be about 0.1 to 10 parts by weight with respect to 100 parts by weight of the vinyl chloride-based resin.

As the antistatic agent, the above-mentioned ones are exemplified. When blending an antistatic agent, the blending amount is recommended to be about 0.1 to 10 parts by weight with respect to 100 parts by weight of the vinyl chloride-based resin.

As the flame retardant, the above-mentioned ones are exemplified. When blending a flame retardant, the blending amount is recommended to be about 0.1 to 20 parts by weight with respect to 100 parts by weight of the vinyl chloride-based resin.

Examples of the foaming agent include organic foaming agents such as azodicarbonamide and oxybisbenzenesulfonyl hydrazide, and inorganic foaming agents such as sodium bicarbonate. When blending a foaming agent, the blending amount is recommended to be about 0.1 to 30 parts by weight with respect to 100 parts by weight of the vinyl chloride-based resin.

As the coloring agent, the above-mentioned ones are exemplified. When blending a coloring agent, the blending amount is recommended to be about 1 to 20 parts by weight with respect to 100 parts by weight of the vinyl chloride-based resin.

The medical vinyl chloride-based resin composition of the present invention can be converted into a powder form, a pellet form or a paste form, for example, by mixing the present diester, the vinyl chloride-based resin, the stabilizer, the silane compound, and as necessary, various additives by hand, depending on purpose of use and applications, or by stirring/mixing them or melt mixing them using an agitation mixer such as a pony mixer, a butterfly mixer, a planetary mixer, a dissolver, a biaxial mixer, a three-roll mill, a mortar mixer, a Henschel mixer, a Banbury mixer, and a ribbon blender, or using a kneader such as a conical twin-screw extruder, a parallel twin-screw extruder, a single screw extruder, a co-kneader, and a roll kneader.

[Medical Material]

The medical vinyl chloride-based resin composition according to the present invention can be molded into a medical material that is a molded body having a desired shape, by molding process using a conventionally known method such as vacuum molding, compression molding, extrusion molding, injection molding, calender molding, press molding, blow molding, powder molding, spread coating, dip coating, spray coating, paper casting, extrusion coating, gravure printing, screen printing, slush molding, rotational molding, casting, dip molding, and welding.

The shape of the molded body that is a medical material is not particularly limited, but may include, for example, a rod shape, a sheet shape, a film shape, a plate shape, a cylindrical shape, a circular shape, an elliptical shape or the like or a special shape such as a star shape and a polygonal shape.

The molded body thus obtained, which is a material for medical use, is very useful as a medical material such as tubes (e.g. chest tubes, dialysis tubes, artificial respiration tubes, endotracheal tubes, respiration apparatus tubes, nutrition tubes, extension tubes, etc.); catheters (e.g. urinary catheters, suction catheters, intravenous injection catheters, digestive tract catheters, etc.); bags (e.g. blood bags, transfusion bags, liquid medicine bags, drain bags, etc.); circuit apparatus parts (e.g. blood component separators, hemodialysis circuits, peritoneal dialysis circuits, artificial heart-lung circuits, etc.); connector members (e.g. connection members, branch valves, speed adjusting members, etc.); medical materials (e.g. transfusion sets, blood transfusion sets, intravenous injection sets, cardiopulmonary bypasses, surgical gloves, packaging materials for pharmaceutical products, medical films, sanitary materials, respiration masks, etc.).

EXAMPLES

Examples are shown below to more specifically explain the present invention. The present invention is not limited to these examples. Abbreviations of the compounds and measurements of the respective characteristics in examples and application examples are shown below.

First Embodiment of the Present Invention (1) Number of Carbon Atoms of Alkyl Group and Ratio of Linear-Chain Alkyl Group As to the number of carbon atoms of the alkyl group and the ratio of the linear-chain alkyl group in the 4-cyclohexene-1,2-dicarboxylic acid diester and the 4,5-epoxycyclohexane dicarboxylic acid diester used in examples and application examples, composition in the raw material alcohol used for the production of such diester compound was measured by gas chromatography (hereinafter abbreviated as GC) and the results were defined as the number of carbon atoms of the alkyl group and the ratio of the linear-chain alkyl group in the raw material ester or in the present diester. The method of measuring the raw material alcohol by GC is as follows.

<<GC Measurement Conditions>>
Apparatus: Gas chromatograph GC-17A (manufactured by Shimadzu Corporation)
Detector: FID
Column: Capillary column ZB-1 30 m
Column temperature: raised from 60° C. to 290° C., temperature rise rate: 13° C./min
Carrier gas: Helium
Sample: 50% acetone solution
Injection volume: 1 μL
Quantitative determination: Quantitative determination was performed using n-propyl benzoate as an internal standard substance.

In selecting the internal standard substance, it has been confirmed in advance that n-propyl benzoate in the raw material alcohol is below the detection limit by GC.

In the above-mentioned esterification reaction, there is no difference in reactivity depending on the structure of the raw material alcohol within the scope of the present invention, and it has been confirmed beforehand that there is no difference between the composition ratio of the raw material alcohol used and the composition ratio of the alkyl group in the raw material ester and in the present diester.

(2) Analysis of Raw Material Ester and Diester

The present diester obtained in the following examples was analyzed by the following method. For the raw material ester as the intermediate material, the following analysis method was also applied.
Element Analysis
<Carbon/Hydrogen>
Organic element analyzer: trade name "CHN Coder MT-5", manufactured by Yanako Bunseki Kogyo KK
Sample amount: 2 mg
Burning furnace temperature: 970° C.
Oxidizing furnace temperature: 850° C.
Reducing furnace temperature: 590° C.
Gas flow rate during combustion: He gas 200 ml/min.
$O_2$ gas 20 ml/min.
<Oxygen>
Organic element analyzer: trade name "Element Analyzer JM-10", manufactured by J-Science Lab Co., Ltd.
Sample amount: 2 mg
Burning furnace temperature: 950° C.
Oxidizing furnace temperature: 850° C.
Reducing furnace temperature: 550° C.
Gas flow ratio during combustion: He gas 200 ml/min.
$O_2$ gas 20 ml/min.

Nuclear Magnetic Resonance Spectroscopic Analysis (NMR Analysis)
NMR analyzer: trade name "DRX-500", manufactured by Bruker
Solvent: deuterated chloroform ($CDCl_3$)
Internal standard substance: tetramethylsilane (TMS)
Sample tube: 5 mm
$^1$H-NMR: resonance frequency: 500.1 MHz, number of integrations 4 times
$^{13}$C-NMR resonance frequency: 125.8 MHz, number of integrations 71 times The measurement sample was prepared by diluting 20 mg of the sample with 0.8 ml of the solvent.
Infrared Spectroscopic Analysis (IR Analysis)
FT-IR device: trade name "Spectrum One", manufactured by Perkin Elmer Co. Ltd., measurement range: 650 to 4000 $cm^{-1}$, measurement method: ATR method, number of integrations: 4 times, resolution: 4.00 $cm^{-1}$ For the measurement, the sample was dropped directly onto the cell of the apparatus and then analyzed.
Chemical Analysis
Ester value: measured according to JIS K-0070 (1992).
Acid value: measured according to JIS K-0070 (1992).
Iodine value: measured according to JIS K-0070 (1992).
Oxirane oxygen: measured according to "Method for Determination of Oxirane Oxygen (Part 1)" of Standard Fat Analysis Test Method 2.3.7.1-2013.
Hue: measured according to JIS K-0071 (1998) to obtain a Hazen unit color number.

Example 1

Esterification Reaction

A 2 L four-necked flask equipped with a thermometer, a decanter, a stirring blade and a reflux condenser was charged with 182.6 g (1.2 moles) of 4-cyclohexene-1,2-dicarboxylic anhydride (RICACID TH, manufactured by New Japan Chemical Co., Ltd.), 416 g (2.9 moles) of a saturated aliphatic alcohol containing 85.1% by weight of a linear-chain saturated aliphatic alcohol having 9 carbon atoms and 11.7% of a branched chain saturated aliphatic alcohol having 9 carbon atoms (LINEVOL 9, manufactured by Shell Chemicals Co., Ltd.: linear chain ratio (molar ratio): 85%), and 0.24 g of tetraisopropyl titanate as an esterification catalyst, and the esterification reaction was carried out at a reaction temperature of 200° C. The reaction was carried out until the acid value of the reaction solution became 0.5 mg KOH/g while removing the produced water out of the system by refluxing the alcohol under reduced pressure. After completion of the reaction, the unreacted alcohol was distilled out of the system under reduced pressure, and the system was neutralized, washed with water, and dehydrated according to a conventional method, thereby to obtain 449 g of an objective 4-cyclohexene-1,2-dicarboxylic acid diester (hereinafter referred to as "raw material ester 1").

The raw material ester 1 thus obtained had an ester value of 262 mg KOH/g, an acid value of 0.04 mg KOH/g, and a hue of 15.
Epoxidation Reaction Then, 423 g (1.0 mole) of the raw material ester 1 was charged into a 1 L four-necked flask equipped with a thermometer, a stirring blade and a cooling tube, and the temperature was raised to 60 to 70° C. After the temperature was raised, 76.6 g (1.35 moles) of 60% hydrogen peroxide water, 18.3 g (0.30 moles) of 76% formic acid, and 1.47 g (0.01 moles) of 75% phosphoric acid were slowly added dropwise over a period of 2.25 hours. After completion of the dropwise addition, the above temperature was maintained for further 4 hours, and the reaction was completed by aging. After completion of the reaction, the aqueous phase was removed to the outside of the system, followed by washing with water and dehydration in a conventional manner to obtain 397 g of an objective 4,5-epoxycyclohexane-1,2-dicarboxylic acid diester (hereinafter referred to as the "diester 1").

The obtained diester 1 was a transparent liquid and had an ester value of 256 mg KOH/g, an acid value of 0.06 mg KOH/g, an iodine value of 2.5 g $I_2$/100 g, an oxirane oxygen content of 3.5%, and a hue of 10.

Elemental analysis, NMR analysis, and IR analysis were carried out on the obtained diester 1, and the results were summarized in Table 1.

The isomer ratio (cis form/trans form, molar ratio) of the oxirane ring site of the present diester 1 calculated from the results of $^1$H-NMR analysis in Table 1 was 20/80.

Example 2

In the same manner as in Example 1 except that 400 g (2.5 moles) of a saturated aliphatic alcohol having 9 to 11 carbon atoms wherein the ratio (molar ratio) of 9 carbon atoms/10 carbon atoms/11 carbon atoms was 18:42:38 and the overall linear chain ratio was 84% (NEODOL 911, manufactured by Shell Chemicals Co., Ltd.) was added instead of 416 g of the saturated aliphatic alcohol (LINEVOL 9, manufactured by Shell Chemicals Co., Ltd.), 404 g of 4,5-epoxycyclohexane dicarboxylic acid diester (hereinafter referred to as the "diester 2") was obtained.

The obtained diester 2 had an ester value of 242 mg KOH/g, an acid value of 0.04 mg KOH/g, an iodine value of 1.9 g $I_2$/100 g, an oxirane oxygen content of 3.1%, and a hue of 10.

Elemental analysis, NMR analysis, and IR analysis were carried out on the obtained diester 2, and the results were summarized in Table 1.

The isomer ratio (cis form/trans form, molar ratio) of the oxirane ring site of the present diester 2 calculated from the results of $^1$H-NMR analysis in Table 1 was 20/80.

TABLE 1

| Example | Element analysis (%) Calcd. | Element analysis (%) Found | Characteristic infrared absorption (cm$^{-1}$) | $^1$H-NMR(CDCl$_3$) 500.1 MHz | | $^{13}$C-NMR(CDCl$_3$) 125.8 MHz | |
|---|---|---|---|---|---|---|---|
| 1 | C: 71.12<br>H: 10.56<br>O: 18.22 | C: 71.46<br>H: 9.81<br>O: 17.88 | 1178 | Absorption of oxirane ring and ester group | 0.89(t, CH3) | Proton of terminal methyl of ester-bonded alkyl group | 14.1(CH3) | Carbon of terminal methyl of ester-bonded alkyl group |
| | | | | | 1.27-1.30 (m, —CH2—) | Proton of methylene of ester-bonded alkyl group | 22.7, 24.8, 25.9, 28.5, 29.2, 29.2, 29.5(—O—CH2—) | Carbon of methylene of ester-bonded alkyl group |
| | | | 1353-1466 | Absorption of alkane bound to ester and cyclohexane ring | 1.62(t, —O—CH2—CH2) | Proton of β-methylene of ester-bonded alkyl group | 31.8(CyCH2) | Carbon of methylene of cyclohexane ring |
| | | | | | 2.19-2.30 (m, CyCH2) | Proton of methylene of cyclohexane ring | 37.7(CyCH) | Carbon of cyclohexane ring at α-position of carbonyl group |
| | | | 1732 | Absorption of ester group | 2.90(t, CyCH) | Proton of cyclohexane ring at α-position of carbonyl group | 50.9(HC—O—CH) | Carbon of methine of oxirane ring (cis form) |
| | | | | | 3.16 (s, HC—O—CH) | Proton of oxirane ring methine (cis form) | 51.6(HC—O—CH) | Carbon of methine of oxirane ring (trans form) |
| | | | 2855-2955 | Absorption of alkane bound to ester and cyclohexane ring | 3.24 (s, HC—O—CH) | Proton of oxirane ring methine (trans form) | 65.1 (—O—CH2—CH2) | Carbon of α-methylene of ester-bonded alkyl group |
| | | | | | 4.06(t, —O—CH2—CH2) | Proton of α-methylene of ester-bonded alkyl group | 173.0(C=O) | Carbon of carbonyl group |
| 2 | C: 72.13<br>H: 10.82<br>O: 17.05 | C: 72.38<br>H: 10.31<br>O: 16.67 | 1178 | Absorption of oxirane ring and ester group | 0.86-0.92 (m, CH3) | Proton of terminal methyl of ester-bonded alkyl group | 14.1, 14.1(CH3) | Carbon of terminal methyl of ester-bonded alkyl group |
| | | | | | 1.26-1.30 (m, —CH2—) | Proton of methylene of ester-bonded alkyl group | 22.7, 24.8, 25.9, 28.5, 29.3, 29.3, 29.5, 29.5, 29.6(—O—CH2—) | Carbon of methylene of ester-bonded alkyl group |
| | | | 1377-1466 | Absorption of alkane bound to ester and cyclohexane ring | 1.60(t, —O—CH2—CH2) | Proton of β-methylene of ester-bonded alkyl group | 31.8(CyCH2) | Carbon of methylene of cyclohexane ring |
| | | | | | 2.10-2.29 (m, CyCH2) | Proton of methylene of cyclohexane ring | 37.7(CyCH) | Carbon of cyclohexane ring at α-position of carbonyl group |
| | | | 1732 | Absorption of ester group | 2.74(t, CyCH) | Proton of cyclohexane ring at α-position of carbonyl group | 50.9(HC—O—CH) | Carbon of methine of oxirane ring (cis form) |
| | | | | | 3.16(s, HC—O—CH) | Proton of oxirane ring methine (cis form) | 51.6(HC—O—CH) | Carbon of methine of oxirane ring (trans form) |

TABLE 1-continued

| Example | Element analysis (%) Calcd. | Element analysis (%) Found | Characteristic infrared absorption (cm$^{-1}$) | Characteristic nuclear magnetic resonance absorption (ppm) $^1$H-NMR(CDCl$_3$) 500.1 MHz | | $^{13}$C-NMR(CDCl$_3$) 125.8 MHz | |
|---|---|---|---|---|---|---|---|
| | | | 2854-2955 Absorption of alkane bound to ester and cyclohexane ring | 3.24(S, HC—O—CH) | Proton of oxirane ring methine (trans form) | 65.11 (—O—CH2—CH2) | Carbon of α-methylene of ester-bonded alkyl group |
| | | | | 4.06(t, —O—CH2—CH2) | Proton of α-methylene of ester-bonded alkyl group | 173.0(C=O) | Carbon of carbonyl group |

Application Example 1

To 100 parts by weight of a versatile vinyl chloride-based resin (trade name "Zest 1000z", manufactured by Shin Dai-Ichi Vinyl Corporation) were respectively added 0.3 parts by weight of calcium stearate (manufactured by Nacalai Tesque, Inc.) and 0.2 parts by weight of zinc stearate (manufactured by Nacalai Tesque, Inc.), and the mixture was stirred and mixed with a mortar mixer, and then 50 parts by weight of the diester 1 obtained in Example 1 or the diester 2 obtained in Example 2 was added. The mixture was further mixed until uniform to obtain a vinyl chloride-based resin composition. This resin composition was melt-kneaded at 160 to 166° C. for 4 minutes using a 5×12 inches twin roll to prepare a roll sheet, followed by press molding at 162 to 168° C.×10 minutes to prepare a press sheet having a thickness of about 1 mm.

Subsequently, a versatile di-2-ethylhexyl phthalate (hereinafter referred to as DOP) instead of the diester according to the present invention, diisononyl 1,2-cyclohexanedicarboxylate (hereinafter referred to as DINCH) that is a cyclohexane dicarboxylic acid diester containing no epoxy group in the molecular structure, and di-2-ethylhexyl 4,5-epoxy-cyclohexane dicarboxylate (hereinafter referred to as E-DEHTH) having a structure outside the scope of the present invention were added in the same manner as above to prepare a vinyl chloride sheet (press sheet).

Using the vinyl chloride sheet obtained above, a tensile test, a cold resistance test, and a heat resistance test were carried out to compare physical properties between the vinyl chloride sheet blended with the diester according to the present invention and the vinyl chloride sheet blended with DOP, DINCH, or E-DEHTH outside the scope of the present invention.

The vinyl chloride sheet blended with the diester according to the present invention was confirmed to be excellent in plasticizer performances because it has very excellent properties as shown by 100% modulus and elongation of the tensile test results, such as flexibility and plasticizing performance equivalent to or better than those of the vinyl chloride sheet blended with other plasticizers.

Further, from the cold resistance test results, it was confirmed that the vinyl chloride sheet blended with the diester of the present invention was very excellent in cold resistance because the sheet has the softening temperature that was lower by 10° C. or more than that of the vinyl chloride sheet blended with other plasticizers such as E-DEHTH, etc.

Further, from the results of the heat resistance test, the volatile loss at 170° C. of the vinyl chloride sheet blended with the diester of the present invention is reduced to ¼ to ⅐ as compared with the vinyl chloride sheet blended with other plasticizer, and the vinyl chloride sheet of the present invention was confirmed to be very excellent in heat resistance.

At the same time, when the discoloration of the vinyl chloride sheet in the above heat resistance test was examined, the vinyl chloride sheet blended with other plasticizer markedly colored in about 1 hour, whereas the vinyl chloride sheet blended with the diester of the present invention was hardly colored, and thus the diester of the present invention was confirmed to acts as a plasticizer and as a stabilizer at the same time.

Application Example 2

To 100 parts by weight of a versatile vinyl chloride-based resin (trade name "Zest 1000z", manufactured by Shin Dai-Ichi Vinyl Corporation) was added 19 parts by weight of the diester 1 obtained in Example 1 or 10 parts by weight of the diester 2 obtained in Example 2, and then 3.0 parts by weight of a calcium-zinc complex stabilizer were further added thereto. The mixture was stirred and mixed with a mortar mixer to prepare a vinyl chloride-based resin composition. This resin composition was melt-kneaded at 170 to 176° C. for 4 minutes using a 5×12 inches twin roll to prepare a roll sheet, followed by press molding at 172 to 178° C.×10 minutes to prepare a press sheet having a thickness of about 0.5 mm.

Using the vinyl chloride sheet obtained above, a tensile test and a heat resistance test were carried out to compare the physical properties between the vinyl chloride sheet blended with the diester of the present invention and the vinyl chloride sheet being not blended with the diester, which is outside the scope of the present invention.

The vinyl chloride sheet not blended with the diester of the present invention begins to be colored in about 30 minutes at a high temperature of 170° C. and becomes markedly colored in about 1 hour, whereas the vinyl chloride sheet blended with the diester of the present invention had little discoloration even after 1 hour under such condition and the diester of the present invention was confirmed to effectively act as a stabilizer, too.

From the above results, it is clear that the diester of the present invention is very useful as a plasticizer and also as a stabilizer.

Second Embodiment of the Present Invention (1) Number of Carbon Atoms of Alkyl Group, and Ratio of Linear-Chain Alkyl Group The number of carbon atoms of alkyl group and the ratio of the linear-chain alkyl group in the plasticizer used in the examples and comparative examples of the present invention were determined by gas chromatography (hereinafter abbreviated as GC) of the composition in the raw material alcohol used for the production. The result was defined as the number of carbon atoms of alkyl group and the ratio of the linear-chain alkyl group in the plasticizer. The method of measuring the raw material alcohol by GC is the same as above.

(2) Evaluation of Physical Properties of Present Diester

The ester value, acid value, iodine value, oxirane oxygen, and hue of the diester obtained in the following production examples were analyzed in the same manner as described above.

(3) Molding Processability

Approximately 0.01 g of a sample obtained by mixing 10 g of a plasticizer with 2 g of a vinyl chloride-based resin (straight, polymerization degree 1050, trade name "Zest 1000Z", manufactured by Shin Dai-Ichi Vinyl Corporation) was dropped onto a slide glass. A cover glass was covered on the slide glass, and set to a melting point apparatus for micro-quantity of a sample. The temperature was raised at a rate of 5° C./min, and changes in the state of the particles of the vinyl chloride-based resin by heating were observed. The temperature at which the particles of the vinyl chloride-based resin start melting and the temperature at which the particles become transparent were defined as the gelation initiation temperature and the gelation termination temperature, respectively, and the average value of them was defined as the gelation temperature. The lower the gelation temperature, the faster the absorption rate of the plasticizer as well as the better the processability.

(4) Preparation of Vinyl Chloride Sheet (Sheet for Tensile Properties Test, Cold Resistance Test, and Heat Resistance Test)

To 100 parts by weight of a vinyl chloride resin (straight, degree of polymerization 1050, trade name "Zest 1000Z") were respectively added 0.3 parts by weight of calcium stearate (manufactured by Nacalai Tesque Co., Ltd.) and 0.2 parts by weight of zinc stearate (manufactured by Nacalai Tesque Co., Ltd.) as a stabilizer. The mixture was stirred and mixed with a mortar mixer, then 50 parts by weight of a plasticizer were added and mixed by hand until homogeneous to obtain a vinyl chloride-based resin composition. This resin composition was melt-kneaded at 160 to 166° C. for 4 minutes using a 5×12 inches twin roll to prepare a roll sheet. Subsequently, press molding of the roll sheet was performed at 162 to 168° C. for 10 minutes to prepare a press sheet having a thickness of about 1 mm.

[Evaluation of Physical Properties of Resin]

(5) Tensile Characteristics: The 100% modulus, the breaking strength and the breaking elongation of the press sheet were measured according to JIS K-6723 (1995). The measurement demonstrated that the smaller the 100% modulus, the more desirable the flexibility. The breaking strength and the breaking elongation are indications of the practical strength of the material. Generally, it can be said that the greater these values, the more superior the practical strength.

(6) Cold Resistance: The cold resistance was measured according to JIS K-6773(1999) using a Clash-Berg tester. The lower the softening temperature (° C.), the more superior the cold resistance. The softening temperature here means the temperature of the low-temperature limit at which a predetermined torsional rigidity rate ($3.17 \times 10^3$ kg/cm²) is obtained in the above measurement.

(7) Heat Resistance: The heat resistance was evaluated based on volatile loss and sheet discoloration.

a) Volatile loss: The roll sheet was heated in a gear oven at 170° C. for 60 minutes and 120 minutes, and a change in the weight was measured; then, the volatile loss (%) was calculated according to the following equation. The smaller the value of volatile loss, the higher the heat resistance.

Volatile loss (%)=((Weight before test−Weight after test)/Weight before test)×100 b) Sheet discoloration: The roll sheet was heated in a gear oven at 170° C. for 30 minutes and 60 minutes; thereafter, the intensity of discoloration of each roll sheet was visually evaluated on a six-level scale.
⊙: Discoloration was not observed.
○: Slight discoloration was observed.
○Δ: Insignificant discoloration was observed.
Δ: Discoloration was observed.
x: Strong discoloration was observed.
xx: Significant discoloration was observed.

Production Example 1

Esterification Reaction

A 2 L four-necked flask equipped with a thermometer, a decanter, a stirring blade and a reflux condenser was charged with 182.6 g of 4-cyclohexene-1,2-dicarboxylic anhydride (1.2 moles, RICACIDTH, manufactured by New Japan Chemical Co., Ltd.), 416 g (2.9 moles) of a saturated aliphatic alcohol containing 85.1% by weight of a linear-chain saturated aliphatic alcohol having 9 carbon atoms and 11.7% of a branched-chain saturated aliphatic alcohol having 9 carbon atoms (LINEVOL 9, manufactured by Shell Chemicals Co., Ltd.), and 0.24 g of tetraisopropyl titanate as an esterification catalyst, and then the esterification reaction was carried out at a reaction temperature of 200° C. The reaction was carried out until the acid value of the reaction solution became 0.5 mg KOH/g while removing the produced water out of the system by refluxing the alcohol under reduced pressure. After completion of the reaction, the unreacted alcohol was distilled out of the system under reduced pressure, and the system was neutralized, washed, and dehydrated according to a conventional method to obtain 449 g of an objective 4-cyclohexene-1,2-dicarboxylic acid diester (hereinafter referred to as "ester 1").

The ester 1 thus obtained had an ester value of 254 mg KOH/g, an acid value of 0.04 mg KOH/g, and a hue of 15.

Epoxidation Reaction

Then, 423 g (1.0 mole) of the ester 1 obtained in the above esterification reaction was charged into a 1 L four-necked flask equipped with a thermometer, a stirring blade and a cooling tube, and the temperature was raised to 60 to 70° C. After the temperature rise, 76.6 g (1.35 moles) of 60% hydrogen peroxide water, 18.3 g (0.30 moles) of 76% formic acid, and 1.47 g (0.01 moles) of 75% phosphoric acid were slowly added dropwise over a period of 2.25 hours. After completion of the dropwise addition, the above temperature was maintained for further 4 hours, and the reaction was completed by aging. After completion of the reaction, the aqueous phase was removed to the outside of the system, followed by washing with water and dehydration in a conventional manner to obtain 397 g of an objective 4,5-epoxycyclohexane dicarboxylic acid diester (hereinafter referred to as "epoxy 1").

The epoxy 1 thus obtained had an ester value of 256 mg KOH/g, an acid value of 0.06 mg KOH/g, an iodine value of 2.5 g $I_2$/100 g, an oxirane oxygen content of 3.5%, and a hue of 10.

Production Example 2

In the same manner as in Production Example 1 except that 400 g (2.5 moles) of mixed saturated aliphatic alcohols having 9 to 11 carbon atoms (NEODOL 911, manufactured by Shell Chemicals Co., Ltd.) wherein the ratio of 9 carbon atoms/10 carbon atoms/11 carbon atoms is 19:43:38 and the overall linear chain ratio was 84% was added instead of 416 g of the saturated aliphatic alcohol (LINEVOL 9, manufactured by Shell Chemicals Co., Ltd.), 404 g of a 4,5-epoxycyclohexane dicarboxylic acid diester (hereinafter referred to as "epoxy 2") was obtained.

The epoxy 2 thus obtained had an ester value of 242 mg KOH/g, an acid value of 0.04 mg KOH/g, an iodine value of 1.9 g $I_2$/100 g, an oxirane oxygen content of 3.1%, and a hue of 10.

Production Example 3

In the same manner as in Production Example 1 except that 251 g (1.7 moles) of n-nonyl alcohol and 167 g (1.2 moles) of isononyl alcohol were added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 3") was obtained.

The epoxy 3 thus obtained had an ester value of 250 mg KOH/g, an acid value of 0.02 mg KOH/g, an iodine value of 1.9 g $I_2$/100 g, an oxirane oxygen content of 3.3%, and a hue of 10.

Production Example 4

In the same manner as in Production Example 1 except that 374 g (2.9 moles) of 2-ethylhexanol was added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 4") was obtained.

The epoxy 4 thus obtained had an ester value of 273 mg KOH/g, an acid value of 0.04 mg KOH/g, an iodine value of 3.3 g $I_2$/100 g, an oxirane oxygen content of 3.5%, and a hue of 10.

Production Example 5

In the same manner as in Production Example 1 except that 416 g (2.9 moles) of isononyl alcohol was added instead of 416 g of the saturated aliphatic alcohol (LINEVOL 9, manufactured by Shell Chemicals Co., Ltd.), 379 g of 4,5-epoxycyclohexane dicarboxylic acid diester (hereinafter referred to as "epoxy 5") was obtained.

The epoxy 5 thus obtained had an ester value of 255 mg KOH/g, an acid value of 0.05 mg KOH/g, an iodine value of 1.6 g $I_2$/100 g, an oxirane oxygen content of 3.4%, and a hue of 10.

Production Example 6

In the same manner as in Production Example 1 except that 459 g (2.9 moles) of isodecyl alcohol was added instead of 416 g of the saturated aliphatic alcohol (LINEVOL 9, manufactured by Shell Chemicals Co., Ltd.), 410 g of 4,5-epoxycyclohexane dicarboxylic acid diester (hereinafter referred to as "epoxy 6") was obtained.

The epoxy 6 thus obtained had an ester value of 239 mg KOH/g, an acid value of 0.05 mg KOH/g, an iodine value of 2.0 g $I_2$/100 g, an oxirane oxygen content of 3.1%, and a hue of 10.

Example 1

According to the method described in "(3) Molding Processability" above, the molding processability (gelation temperature) was measured using the epoxycyclohexane dicarboxylic acid diester (epoxy 1) obtained in Production Example 1. The obtained results were shown in Table 2.

Subsequently, as described in "(4) Preparation of Vinyl Chloride Sheet", a soft vinyl chloride-based resin composition was prepared by using the epoxy 1 as a plasticizer, and from the obtained soft vinyl chloride-based resin composition, a vinyl chloride sheet was prepared. The sheet was subjected to a tensile test, a cold resistance test and a heat resistance test. The obtained results were summarized in Table 2.

Example 2

In the same manner as in Example 1 except that the epoxy 2 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, and a heat resistance test. The obtained results were summarized in Table 2.

Example 3

In the same manner as in Example 1 except that the epoxy 3 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, and a heat resistance test. The obtained results were summarized in Table 2.

Comparative Example 1

In the same manner as in Example 1 except that the epoxy 4 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, and a heat resistance test. The obtained results were summarized in Table 2.

Comparative Example 2

In the same manner as in Example 1 except that the epoxy 5 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, and a heat resistance test. The obtained results were summarized in Table 2.

Comparative Example 3

In the same manner as in Example 1 except that the epoxy 6 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, and a heat resistance test. The obtained results were summarized in Table 2.

Comparative Example 4

In the same manner as in Example 1 except that di-2-ethylhexyl phthalate (SANSO CIZER DOP, manufactured by New Japan Chemical Co., Ltd.) was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test and a heat resistance test. The obtained results were summarized in Table 2.

Comparative Example 5

In the same manner as in Example 1 except that diisononyl phthalate (SANSO CIZER DINP, manufactured by New Japan Chemical Co., Ltd.) was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test and a heat resistance test. The obtained results were summarized in Table 2.

Comparative Example 6

In the same manner as in Example 1 except that commercially available tri-2-ethylhexyl trimellitate (TOTM) was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test and a heat resistance test. The obtained results were summarized in Table 2.

diester of the present invention and when considering excellent molding processability, flexibility and cold resistance, usefulness of such a diester is obvious. Also, the results in Table 2 revealed that by using the 4,5-epoxycyclohexane dicarboxylic acid diester of the present invention (Examples 1 and 3) as a plasticizer, the cold resistance and heat resistance are greatly improved while maintaining equivalent molding processability and flexibility, when compared with the case in which the conventional 4,5-epoxycyclohexane dicarboxylic acid diester (Comparative Example 1) is used. In addition, such effect is clear as compared with the case of using the 4,5-epoxycyclohexane dicarboxylic acid diester (Comparative Examples 2 and 3) outside the scope of the present invention. Similarly, when the 4,5-epoxycyclohexane dicarboxylic acid diester of the present invention (Example 2) is used as a plasticizer, the molding processability equal to or higher than that of phthalic acid diester which is a versatile plasticizer is exhibited, and its cold resistance and heat resistance are further improved. Thus, it is understood that the 4,5-epoxycyclohexane dicarboxylic acid diester of the present invention is particularly useful when used in a more severe environment.

Third Embodiment of the Present Invention (1) Number of Carbon Atoms of Alkyl Group and Ratio of Linear-Chain Alkyl Group The number of carbon atoms of alkyl group and the ratio of the linear-chain alkyl group in the stabilizer used in examples and comparative examples of the present invention were determined by gas chromatography (hereinafter abbreviated as GC) of the composition of the raw material alcohol used for the production. The results were defined as the number of carbon atoms of alkyl group and the ratio of

TABLE 2

| | | | Example | | | Comparative Example | | | | | |
|---|---|---|---|---|---|---|---|---|---|---|---|
| Test items | | Unit (condition) | 1 | 2 | 3 | 1 | 2 | 3 | 4 | 5 | 6 |
| Plasticizer | Kind | | Epoxy 1 | Epoxy 2 | Epoxy 3 | Epoxy 4 | Epoxy 5 | Epoxy 6 | DOP | DINP | TOTM |
| | Ratio of linear-chain alkyl group (%) | | 87 | 84 | 60 | 0 | 5 | 0 | 0 | 5 | 0 |
| Molding processability | Gelation temperature | °C. | 118 | 122 | 118 | 105 | 120 | 128 | 112 | 118 | 135 |
| Tensile characteristics | 100% modulus | MPa | 9.9 | 10.5 | 10.3 | 9.8 | 10.6 | 11.6 | 9.4 | 10.2 | 13.1 |
| | Strength | MPa | 21.4 | 22.2 | 22.6 | 22.4 | 22.1 | 23.5 | 21.4 | 20.1 | 24.0 |
| | Elongation | % | 324 | 340 | 336 | 318 | 319 | 345 | 320 | 320 | 330 |
| Cold resistance | Softening temperature | °C. | −25 | −27 | −23 | −15 | −18 | −14 | −24 | −27 | −17 |
| Heat resistance | Volatile loss | % (170° C., 60 min) | 2.1 | 1.0 | 2.4 | 7.9 | 3.4 | 2.6 | 8.8 | 3.9 | 0.6 |
| | | % (170° C., 120 min) | 4.0 | 2.1 | 4.7 | 13.0 | 6.0 | 4.9 | 15.1 | 8.5 | 1.2 |
| | Sheet discoloration | (170° C., 30 min) | ◎ | ◎ | ◎ | ◎ | ◎ | ◎ | Δ | Δ | ◯ |
| | | (170° C., 60 min) | ◎ | ◎ | ◎ | ◎ | ◎ | ◎ | XX | XX | X |

The results of Table 2 revealed that by using the 4,5-epoxycyclohexane dicarboxylic acid diester of the present invention (Examples 1 to 3) as a plasticizer, the heat resistance, particularly heat discoloration property can be largely improved while maintaining molding processability, flexibility, and cold resistance equivalent to those of the phthalate diester which is currently the most frequently used plasticizer (Comparative Examples 4 and 5). Furthermore, although the volatility resistance is somewhat inferior as compared with the trimellitic acid ester (Comparative Example 6) which is frequently used as a heat resistant plasticizer, the heat resistant discoloration property is greatly improved in the 4,5-epoxycyclohexane dicarboxylic acid the linear-chain alkyl group in the stabilizer. The method of measuring the raw material alcohol by GC is the same as above.

(2) Evaluation of Physical Properties of Raw Material Ester and Present Diester

The ester value, acid value, iodine value, oxirane oxygen, and hue of the raw material ester and the present diester obtained in the following production examples were analyzed in the same manner as described above.

(3) Preparation of Vinyl Chloride Sheet

[Method 1: Hard and Semi-Hard Vinyl Chloride Sheet]

A prescribed amount of the stabilizer according to the present invention as shown in Table 3 was blended with 100 parts by weight of a vinyl chloride-based resin (straight, polymerization degree 1050, trade name "Zest 1000Z", manufactured by Shin Dai-Ichi Vinyl Corporation), and 3.0 parts by weight of a calcium-zinc composite stabilizer as a stabilizer outside the scope of the present invention was added thereto. The mixture was stirred and mixed with a mortar mixer to obtain a vinyl chloride-based resin composition. This resin composition was melt-kneaded at 170 to 176° C. for 4 minutes using a 5×12 inches twin roll to prepare a roll sheet. Subsequently, press molding of the roll sheet was carried out at 172 to 178° C. for 10 minutes to prepare a press sheet having a thickness of about 0.5 mm.

[Method 2: Soft Vinyl Chloride Sheet]

A prescribed amount of the stabilizer according to the present invention as shown in Table 4 was blended with 100 parts by weight of a vinyl chloride-based resin (straight, polymerization degree 1050, trade name "Zest 1000Z", manufactured by Shin Dai-Ichi Vinyl Corporation), and 0.3 parts by weight of calcium stearate (manufactured by Nacalai Tesque Co., Ltd.) and 0.2 parts by weight of zinc stearate (manufactured by Nacalai Tesque Co., Ltd.) were respectively added thereto as a stabilizer outside the scope of the present invention, and stirred and mixed in a mortar mixer to obtain a vinyl chloride-based resin composition. Subsequently, after stirring and mixing with a mortar mixer, 30 parts by weight of a plasticizer was further added and mixed by hand until uniform, thereby obtaining a soft vinyl chloride-based resin composition. This resin composition was melt-kneaded at 160 to 166° C. for 4 minutes using a 5×12 inches twin roll to prepare a roll sheet. Subsequently, press molding was performed at 162 to 168° C. for 10 minutes to prepare a press sheet having a thickness of about 1 mm.

[Evaluation of Physical Properties of Resin]

(4) Tensile Characteristics: Elastic modulus or 100% modulus, breaking strength, and breaking elongation of the press sheet were measured according to JIS K-6723 (1995). The smaller the elastic modulus or the 100% modulus, the better the flexibility. The breaking strength and breaking elongation are indications of the practical strength of the material. Generally, it can be said that the greater these values, the more superior the practical strength.

(5) Heat Resistance: The heat resistance was evaluated based on volatile loss and sheet discoloration.

a) Volatile loss: A roll sheet was heated in a gear oven at 170° C. for 30 minutes and 60 minutes, and the volatile loss (%) was calculated according to the following formula.

It can be said that the smaller the value, the more excellent the heat resistance, resulting in little reduction in the effect as a stabilizer.

Volatile loss (%)=((Weight before test−Weight after test)/Weight before test)×100 b) Sheet discoloration: A roll sheet was heated in a gear oven at 170° C. for 30 minutes and 60 minutes; thereafter, the intensity of discoloration of each roll sheet was visually evaluated on a six-level scale.

Although sheet discoloration is an evaluation of heat resistance, it is also an index of the effect (stabilization effect) as a stabilizer against heat. That is, it can be said that the less the discoloration, the more effectively the added stabilizer acts as a stabilizer resistant to heat, leading to suppression of such discoloration.

⊙: Discoloration was not observed.
○: Slight discoloration was observed.
○Δ: Insignificant discoloration was observed.
Δ: Discoloration was observed.
x: Strong discoloration was observed.
xx: Significant discoloration was observed.

(6) Heat resistance (aging property): According to JIS K-6723 (1995), a tensile test was conducted after heating at 120° C.×120 hours. The results were shown as a 100% modulus residual ratio (%) and a breaking elongation residual ratio (%) of the press sheet compared with a normal state.

The closer the result value is to 100, the less the change in physical properties after heating, and thus it can be said that the press sheet is excellent in heat aging resistance. Moreover, this test is not only a heat resistance test but also an index of the effect (stabilizing effect) as a stabilizer against heat. That is, it is thought that as the result value approaches 100, the added stabilizer effectively acts as a stabilizer against heat and suppresses aging.

100% modulus residual ratio %=(1−(100% modulus after heating−100% modulus before heating/ 100% modulus before heating))×100

Elongation residual ratio %=(breaking elongation after heating/breaking elongation before heating)×100

(7) Fogging Resistance

A press sheet (4 g) was placed in a glass-made sample bottle, and the bottle was set in a fogging tester adjusted to 100° C. Further, a glass plate lid was placed on the sample bottle, and a cooling plate with a cooling water flow adjusted to 20° C. was placed thereon, and a heat treatment was performed at 100° C. for 3 hours. After the heat treatment, the fogging degree (Haze) (%) of the glass plate was measured using a haze meter (Haze Guard II: manufactured by Toyo Seiki Seisakusho KK).

The smaller the haze value, the more superior the fogging resistance.

Production Example 1

Esterification Reaction

A 2 L four-necked flask equipped with a thermometer, a decanter, a stirring blade and a reflux condenser was charged with 182.6 g of 4-cyclohexene-1,2-dicarboxylic anhydride (1.2 moles, RICACIDTH, manufactured by New Japan Chemical Co., Ltd.), 416 g (2.9 moles) of a saturated aliphatic alcohol containing 85.1% by weight of a linear-chain saturated aliphatic alcohol having 9 carbon atoms and 11.7% of a branched-chain saturated aliphatic alcohol having 9 carbon atoms (LINEVOL 9, manufactured by Shell Chemicals Co., Ltd.: linear chain ratio (molar ratio): 85%), and 0.24 g of tetraisopropyl titanate as an esterification catalyst, and then the esterification reaction was carried out at a reaction temperature of 200° C. The reaction was carried out until the acid value of the reaction solution became 0.5 mg KOH/g while removing the produced water out of the system by refluxing the alcohol under reduced pressure. After completion of the reaction, the unreacted alcohol was distilled out of the system under reduced pressure, and the system was neutralized, washed, and dehydrated according to a conventional method to obtain 449 g of an objective 4-cyclohexene-1,2-dicarboxylic acid diester (hereinafter referred to as "ester 1").

The ester 1 thus obtained had an ester value of 262 mg KOH/g, an acid value of 0.04 mg KOH/g, and a hue of 15.

Epoxidation Reaction

Then, 423 g (1.0 mole) of the ester 1 obtained in the above esterification reaction was charged into a 1 L four-necked flask equipped with a thermometer, a stirring blade and a cooling tube, and the temperature was raised to 60 to 70° C.

After the temperature rise, 76.6 g (1.35 moles) of 60% hydrogen peroxide water, 18.3 g (0.30 moles) of 76% formic acid, and 1.47 g (0.01 moles) of 75% phosphoric acid were slowly added dropwise over a period of 2.25 hours. After completion of the dropwise addition, the above temperature was maintained for further 4 hours, and the reaction was completed by aging. After completion of the reaction, the aqueous phase was removed to the outside of the system, followed by washing with water and dehydration in a conventional manner to obtain 397 g of an objective 4,5-epoxycyclohexane dicarboxylic acid diester (hereinafter referred to as "epoxy 1").

The epoxy 1 thus obtained had an ester value of 256 mg KOH/g, an acid value of 0.06 mg KOH/g, an iodine value of 2.5 g $I_2$/100 g, an oxirane oxygen content of 3.5%, and a hue of 10.

Production Example 2

In the same manner as in Production Example 1 except that 400 g (2.5 moles) of mixed saturated aliphatic alcohols having 9 to 11 carbon atoms (NEODOL 911, manufactured by Shell Chemicals Co., Ltd.) wherein the ratio (molar ratio) of 9 carbon atoms/10 carbon atoms/11 carbon atoms is 18:42:38 and the overall linear chain ratio was 84% was added instead of 416 g of the saturated aliphatic alcohol (LINEVOL 9, manufactured by Shell Chemicals Co., Ltd.), 404 g of a 4,5-epoxycyclohexane dicarboxylic acid diester (hereinafter referred to as "epoxy 2") was obtained.

The epoxy 2 thus obtained had an ester value of 242 mg KOH/g, an acid value of 0.04 mg KOH/g, an iodine value of 1.9 g $I_2$/100 g, an oxirane oxygen content of 3.1%, and a hue of 10.

Production Example 3

In the same manner as in Production Example 1 except that 374 g (2.9 moles) of 2-ethylhexanol was added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 3") was obtained.

The epoxy 3 thus obtained had an ester value of 273 mg KOH/g, an acid value of 0.04 mg KOH/g, an iodine value of 3.3 g $I_2$/100 g, an oxirane oxygen content of 3.5%, and a hue of 10.

Example 1

According to the method described in "Method 1: Hard and Semi-Hard Vinyl Chloride Sheet" of "(3) Preparation of Vinyl Chloride Sheet", a vinyl chloride-based resin composition was prepared using 19 parts by weight of the epoxycyclohexane dicarboxylic acid diester (epoxy 1) as a stabilizer, and a vinyl chloride sheet was prepared from the obtained vinyl chloride-based resin composition. Then, the vinyl chloride sheet was subjected to a tensile test, a heat resistance test, and a fogging resistance test. The obtained results were summarized in Table 3.

The vinyl chloride sheet prepared above showed no signs of bleeding or the like at all even if left for 1 month at room temperature.

Example 2

A vinyl chloride-based resin composition was prepared in the same manner as in Example 1 except that 10 parts by weight of the epoxy 2 was used as a stabilizer instead of 19 parts by weight of the epoxy 1 to prepare a vinyl chloride-based resin composition. From the resin composition obtained, a vinyl chloride sheet was prepared and subjected to a tensile test, a heat resistance test, and a fogging resistance test. The obtained results were summarized in Table 3.

The vinyl chloride sheet prepared above showed no signs of bleeding or the like at all even if left for 1 month at room temperature.

Example 3

According to the method described in "Method 2: Soft Vinyl Chloride Sheet" of "(3) Preparation of Vinyl Chloride Sheet", a vinyl chloride-based resin composition was prepared using 19 parts by weight of the epoxycyclohexane dicarboxylic acid diester (epoxy 1) as a stabilizer and tri-2-ethylhexyl trimellitate (TOTM) as a plasticizer, and a vinyl chloride sheet was prepared from the obtained vinyl chloride-based resin composition. Then, the vinyl chloride sheet was subjected to a tensile test, a heat resistance test, and a fogging resistance test. The obtained results were summarized in Table 4.

Example 4

A vinyl chloride-based resin composition was prepared in the same manner as in Example 3 except that the epoxy 2 was used instead of the epoxy 1, and a vinyl chloride sheet was prepared from the obtained vinyl chloride-based resin composition, and subjected to a tensile test, a heat resistance test, and a fogging resistance test. The obtained results were summarized in Table 4.

Example 5

A vinyl chloride-based resin composition was prepared in the same manner as in Example 3 except that a trimellitic acid triester (TL9TM) of the saturated aliphatic alcohol (LINEVOL 9) was used instead of TOTM, and a vinyl chloride sheet was prepared from the obtained vinyl chloride-based resin composition. The vinyl chloride sheet was subjected to a tensile test, a heat resistance test, and a fogging resistance test. The obtained results were summarized in Table 4.

Comparative Example 1

A vinyl chloride-based resin composition was prepared in the same manner as in Example 1 except that the epoxy 1 was not added. Then, a vinyl chloride sheet was prepared from the obtained vinyl chloride-based resin composition, and subjected to a tensile test, a heat resistance test, and a fogging resistance test. The obtained results were summarized in Table 3.

Comparative Example 2

A vinyl chloride-based resin composition was prepared in the same manner as in Example 1 except that the epoxy 3 was used instead of the epoxy 1. Then, a vinyl chloride sheet was prepared from the obtained vinyl chloride-based resin composition, and subjected to a tensile test, a heat resistance test, and a fogging resistance test. The obtained results were summarized in Table 3.

Comparative Example 3

A vinyl chloride-based resin composition was prepared in the same manner as in Example 3 except that the epoxy 1 was not added. Then, a vinyl chloride sheet was prepared from the obtained vinyl chloride-based resin composition, and subjected to a tensile test, a heat resistance test, and a fogging resistance test. The obtained results were summarized in Table 4.

Comparative Example 4

A vinyl chloride-based resin composition was prepared in the same manner as in Example 3 except that the epoxy 3 was used instead of the epoxy 1. Then, a vinyl chloride sheet was prepared from the obtained vinyl chloride-based resin composition, and subjected to a tensile test, a heat resistance test, and a fogging resistance test. The obtained results were summarized in Table 4.

The results in Tables 3 and 4 revealed that by blending the epoxycyclohexane dicarboxylic acid diester of the present invention (Examples 1 to 5), discoloration due to heat and deterioration in physical properties due to heat, that is, thermal deterioration is remarkably reduced, compared with the case (Comparative Examples 1 and 3) wherein the diester was not blended. When a conventional epoxycyclohexane dicarboxylic acid diester, that is, an epoxycyclohexane dicarboxylic acid diester outside the scope of the present invention (Comparative Examples 2 and 4) is blended, a tendency to decrease the fogging property is observed, whereas when the epoxycyclohexane dicarboxylic acid diester (Examples 1 to 5) within the scope of the present invention is blended, almost no deterioration in fogging property is recognized. These tendencies are exactly the same as those observed from the hard composition to the soft composition to which a heat resistant plasticizer is added. From the above results, it is understood that the epoxycyclohexane dicarboxylic acid diester according to the present

TABLE 3

| Test items | | Unit (Condition) | Example 1 | Example 2 | Comparative Example 1 | Comparative Example 2 |
|---|---|---|---|---|---|---|
| Stabilizer | Kind | | Epoxy 1 | Epoxy 2 | — | Epoxy 3 |
| | Blending amount | (Parts by weight) | 19 | 10 | — | 19 |
| Tensile characteristics | Elastic modulus | MPa | 2080 | 2630 | 3270 | 2370 |
| | Strength | MPa | 39.6 | 48.6 | 61.3 | 50.0 |
| | Elongation | % | 221 | 120 | 44 | 67 |
| Heat resistance | Sheet discoloration | (170° C., 30 minutes) | ○ | ○ | Δ | ○ |
| | | (170° C., 60 minutes) | ○ | ○ | X | Δ |
| | Volatile loss | (170° C., 30 minutes) | 0.8 | 0.6 | 0.1 | 2.9 |
| | | (170° C., 60 minutes) | 1.6 | 1.2 | 0.2 | 4.5 |
| | Elongation residual ratio | % | 99 | 100 | 79 | 83 |
| Fogging resistance | | (100° C., 3 hours) | 0.6 | 0.5 | 0.3 | 8.9 |

TABLE 4

| Test items | | Unit (Condition) | Example 3 | Example 4 | Example 5 | Comparative Example 3 | Comparative Example 4 |
|---|---|---|---|---|---|---|---|
| Plasticizer | Kind | | TOTM | TOTM | TL9TM | TOTM | TOTM |
| Stabilizer | Kind | | Epoxy 1 | Epoxy 2 | Epoxy 1 | — | Epoxy 3 |
| | Blending amount | (Parts by weight) | 19 | 19 | 19 | — | 19 |
| Tensile characteristics | 100% modulus | MPa | 11.9 | 12.4 | 11.6 | 22.4 | 12.5 |
| | Strength | MPa | 22.8 | 22.7 | 23.5 | 29.9 | 23.1 |
| | Elongation | % | 329 | 316 | 354 | 270 | 320 |
| Heat resistance | Sheet discoloration | (170° C., 30 minutes) | ◎ | ◎ | ◎ | Δ | ◎ |
| | | (170° C., 60 minutes) | ◎ | ◎ | ◎ | X | ○ |
| | Volatile loss | (170° C., 30 minutes) | 0.5 | 0.3 | 0.5 | 0.3 | 1.3 |
| | | (170° C., 60 minutes) | 1.0 | 0.6 | 0.9 | 0.6 | 2.2 |
| | 100% modulus residual ratio | % | 101 | 100 | 101 | 100 | 130 |
| | Elongation residual ratio | % | 98 | 99 | 98 | 81 | 84 |
| Fogging resistance | | (100° C., 3 hours) | 0.5 | 0.3 | 0.3 | 0.2 | 6.7 | invention is widely useful as a very excellent stabilizer from hard applications to semi-hard or soft applications.

Fourth Embodiment of the Present Invention (1) Number of Carbon Atoms of Alkyl Group and Ratio of Linear-Chain Alkyl Group The number of carbon atoms of alkyl group and the ratio of the linear-chain alkyl group in the plasticizer used in examples and comparative examples of the present invention were determined by gas chromatography (hereinafter abbreviated as GC) of the composition in the raw material alcohol used for the production. The result was defined as the number of carbon atoms of alkyl group and the ratio of the linear-chain alkyl group in the plasticizer. The method of measuring the raw material alcohol by GC is the same as above.

(2) Evaluation of Physical Properties of Raw Material Ester and Present Diester

The ester value, acid value, iodine value, oxirane oxygen, and hue of the raw material ester and the present ester obtained in the following production examples were analyzed in the same manner as described above.

(3) Preparation of Vinyl Chloride Sheet

To 100 parts by weight of a vinyl chloride-based resin (straight, polymerization degree 1050, trade name "Zest 1000Z", manufactured by Shin Dai-Ichi Vinyl Corporation) were respectively added 0.3 parts by weight of calcium stearate (manufactured by Nacalai Tesque, Inc.) and 0.2 parts by weight of zinc stearate as a stabilizer other than the stabilizer outside the scope of the present invention, and the mixture was stirred and mixed with a mortar mixer to obtain a vinyl chloride-based resin composition. After stirring and mixing with a mortar mixer, a predetermined amount of the diester of the present invention as shown in Table 5 was added and mixed by hand until uniform, thereby obtaining a vinyl chloride-based resin composition. This resin composition was melt-kneaded at 160 to 166° C. for 4 minutes using a 5×12 inches twin roll to prepare a roll sheet. Subsequently, press molding was performed at 162 to 168° C. for 10 minutes to prepare a press sheet having a thickness of about 1 mm.

[Evaluation of Physical Properties of Resin]

(4) Tensile Characteristics: The 100% modulus, the breaking strength and the breaking elongation of the press sheet were measured according to JIS K-6723 (1995). The measurement demonstrated that the smaller the 100% modulus, the more desirable the flexibility. The breaking strength and the breaking elongation are indications of the practical strength of the material. Generally, it can be said that the greater these values, the more superior the practical strength.

(5) Cold Resistance: The softening temperature (° C.) of the press sheet was measured according to JIS K-6773 (1999) using a Clash-Berg tester. The lower the softening temperature (° C.), the more superior the cold resistance. The softening temperature here refers to a low temperature limit indicating a predetermined torsional rigidity rate ($3.17 \times 10^3$ kg/cm$^2$) in the above measurement.

(6) Heat Resistance (Volatility, Discoloration): The heat resistance was determined according to evaluation of volatile loss and sheet discoloration after heating.

a) Volatile loss: The roll sheet was heated in a gear oven at 170° C. for 60 minutes and 120 minutes, and a change in the weight was measured; then, the volatile loss (%) was calculated according to the following equation. The smaller the value of volatile loss, the higher the heat resistance.

Volatile loss (%)=((Weight before test−Weight after test)/Weight before test)×100 b) Sheet discoloration: The roll sheet was heated in a gear oven at 170° C. for 30 minutes and 60 minutes; thereafter, the intensity of discoloration of each roll sheet was visually evaluated on a six-level scale.

⊙: Discoloration was not observed.
◯: Slight discoloration was observed.
◯θA: Insignificant discoloration was observed.
Δ: Discoloration was observed.
x: Strong discoloration was observed.
xx: Significant discoloration was observed.

(7) Fogging Resistance

A press sheet (4 g) was placed in a glass-made sample bottle, and the bottle was set in a fogging tester adjusted to 100° C. Further, a glass plate lid was placed on the sample bottle, and a cooling plate with a cooling water flow adjusted to 20° C. was placed thereon, and a heat treatment was performed at 100° C. for 3 hours. After the heat treatment, the degree of fogging on the surface of the glass plate was visually observed and evaluated on the basis of four grades. The haze (%) of the glass plate was measured using a haze meter (HAZE GUARD II, manufactured by Toyo Seiki Seisakusho). The smaller the haze value, the more excellent the fogging resistance.

[Four-Grade Evaluation by Visual Observation]

⊙: No fogging occurred at all, and there was no influence on the field of view beyond the glass plate.
◯: Slight fogging occurred, which was not so much as to affect the field of view beyond the glass plate.
Δ: Fogging obviously occurred, and visibility beyond the glass plate was slightly affected.
x: The degree of fogging on the surface of the glass plate was so severe that the field of view beyond the glass plate has decreased.

(8) Heat-Aging Resistance: A tensile test was performed on the press sheet after heating under the conditions of 100° C. for 120 hours according to JIS K-6723 (1995). The results were shown as a 100% modulus residual ratio (%) and a breaking elongation residual ratio (%) of the press sheet after testing in a normal state. The closer the value is to 100%, the better the heat aging resistance.

100% modulus residual ratio (%)=(100% modulus of press sheet in tensile test after heating)/(100% modulus of press sheet in tensile test before heating)×100

Breaking elongation residual ratio=(breaking elongation of press sheet in tensile test after heating)/(breaking elongation of press sheet in tensile test before heating)×100

(9) Light Resistance: Yellow index (YI) after 200 hours irradiation test by a xenon weather meter (Suga Test Instruments Co., Ltd.) was measured.

Production Example 1

Esterification Reaction

A 2 L four-necked flask equipped with a thermometer, a decanter, a stirring blade and a reflux condenser was charged with 182.6 g of 4-cyclohexene-1,2-dicarboxylic anhydride (1.2 moles, RICACIDTH, manufactured by New Japan Chemical Co., Ltd.), 416 g (2.9 moles) of a saturated aliphatic alcohol containing 85.1% by weight of a linear-chain saturated aliphatic alcohol having 9 carbon atoms and 11.7% of a branched-chain saturated aliphatic alcohol having 9 carbon atoms (LINEVOL 9, the ratio of the linear-chain saturated aliphatic alcohol: 87%, manufactured by Shell Chemicals Co., Ltd.), and 0.24 g of tetraisopropyl titanate as an esterification catalyst, and then the esterification reaction was carried out at a reaction temperature of 200° C. The reaction was carried out until the acid value of the reaction solution became 0.5 mg KOH/g while removing the produced water out of the system by refluxing the alcohol under reduced pressure. After completion of the reaction, the unreacted alcohol was distilled out of the system under reduced pressure, and the system was neutralized, washed, and dehydrated according to a conventional method to obtain 449 g of an objective 4-cyclohexene-1,2-dicarboxylic acid diester (hereinafter referred to as "ester 1").

The ester 1 thus obtained had an ester value of 254 mg KOH/g, an acid value of 0.04 mg KOH/g, and a hue of 15.

Epoxidation Reaction

Then, 423 g (1.0 mole) of the ester 1 obtained in the above esterification reaction was charged into a 1 L four-necked flask equipped with a thermometer, a stirring blade and a cooling tube, and the temperature was raised to 60 to 70° C. After the temperature rise, 76.6 g (1.35 moles) of 60% hydrogen peroxide water, 18.3 g (0.30 moles) of 76% formic acid, and 1.47 g (0.01 moles) of 75% phosphoric acid were slowly added dropwise over a period of 2.25 hours. After completion of the dropwise addition, the above temperature was maintained for further 4 hours, and the reaction was completed by aging. After completion of the reaction, the aqueous phase was removed to the outside of the system, followed by washing with water and dehydration in a conventional manner to obtain 397 g of an objective 4,5-epoxycyclohexane dicarboxylic acid diester (hereinafter referred to as "epoxy 1").

The epoxy 1 thus obtained had an ester value of 256 mg KOH/g, an acid value of 0.06 mg KOH/g, an iodine value of 2.5 g I$_2$/100 g, an oxirane oxygen content of 3.5%, and a hue of 10.

Production Example 2

In the same manner as in Production Example 1 except that 400 g (2.5 moles) of mixed saturated aliphatic alcohols having 9 to 11 carbon atoms (NEODOL 911, manufactured by Shell Chemicals Co., Ltd.) wherein the ratio of 9 carbon atoms/10 carbon atoms/11 carbon atoms is 19:43:38 and the ratio of the linear-chain saturated aliphatic alcohol was 84% was added instead of 416 g of the saturated aliphatic alcohol (LINEVOL 9, manufactured by Shell Chemicals Co., Ltd.), 404 g of a 4,5-epoxycyclohexane dicarboxylic acid diester (hereinafter referred to as "epoxy 2") was obtained.

The epoxy 2 thus obtained had an ester value of 242 mg KOH/g, an acid value of 0.04 mg KOH/g, an iodine value of 1.9 g I$_2$/100 g, an oxirane oxygen content of 3.1%, and a hue of 10.

Production Example 3

In the same manner as in Production Example 1 except that 198 g (1.4 moles) of n-nonyl alcohol and 162 g (1.1 moles) of isononyl alcohol were added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 3") was obtained. The ratio of the linear-chain saturated aliphatic alcohol was 60%.

The epoxy 3 thus obtained had an ester value of 256 mg KOH/g, an acid value of 0.05 mg KOH/g, an iodine value of 2.5 g I$_2$/100 g, an oxirane oxygen content of 3.5%, and a hue of 10.

Production Example 4

In the same manner as in Production Example 1 except that 374 g (2.9 moles) of 2-ethylhexanol was added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 4") was obtained.

The epoxy 4 thus obtained had an ester value of 273 mg KOH/g, an acid value of 0.04 mg KOH/g, an iodine value of 3.3 g I$_2$/100 g, an oxirane oxygen content of 3.5%, and a hue of 10.

Production Example 5

In the same manner as in Production Example 1 except that 416 g (2.9 moles) of isononyl alcohol was added instead of 416 g of the saturated aliphatic alcohol (LINEVOL 9, manufactured by Shell Chemicals Co., Ltd.), 379 g of 4,5-epoxycyclohexane dicarboxylic acid diester (hereinafter referred to as "epoxy 5") was obtained.

The epoxy 5 thus obtained had an ester value of 255 mg KOH/g, an acid value of 0.05 mg KOH/g, an iodine value of 1.6 g I$_2$/100 g, an oxirane oxygen content of 3.4%, and a hue of 10.

Production Example 6

In the same manner as in Production Example 1 except that 459 g (2.9 moles) of isodecyl alcohol was added instead of 416 g of the saturated aliphatic alcohol (LINEVOL 9, manufactured by Shell Chemicals Co., Ltd.), 410 g of 4,5-epoxycyclohexane dicarboxylic acid diester (hereinafter referred to as "epoxy 6") was obtained.

The epoxy 6 thus obtained had an ester value of 239 mg KOH/g, an acid value of 0.05 mg KOH/g, an iodine value of 2.0 g I$_2$/100 g, an oxirane oxygen content of 3.1%, and a hue of 10.

Example 1

According to the method described in "(3) Preparation of Vinyl Chloride Sheet", a vinyl chloride-based resin composition was prepared by using a predetermined amount as shown in Table 5 of the epoxycyclohexane dicarboxylic acid diester (epoxy 1) obtained in Production Example 1. From the obtained vinyl chloride-based resin composition, a vinyl chloride sheet was prepared and then subjected to a tensile test, a cold resistance test, a heat resistance test, a light resistance test, and a fogging resistance test. The obtained results were summarized in Table 5.

Example 2

A vinyl chloride-based resin composition was prepared in the same manner as in Example 1 except that the epoxy 2 was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Example 3

A vinyl chloride-based resin composition was prepared in the same manner as in Example 1 except that the epoxy 3 was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Example 4

A vinyl chloride-based resin composition was prepared in the same manner as in Example 1 except that the blending amount of the epoxy 1 was reduced to 10 parts, and 40 parts of diisononyl 1,2-cyclohexane dicarboxylate (HEXAMOLL DINCH, manufactured by BASF) was used. A vinyl chloride sheet was prepared from the obtained vinyl chloride-based resin composition and subjected to a tensile test, a cold resistance test, a heat resistance test, a light resistance test, and a fogging resistance test. The obtained results were summarized in Table 5.

Example 5

A vinyl chloride-based resin composition was prepared in the same manner as in Example 2 except that the blending amount of the epoxy 2 was reduced to 10 parts, and 40 parts of diisononyl 1,2-cyclohexane dicarboxylate (HEXAMOLL DINCH, manufactured by BASF) was used. A vinyl chloride sheet was prepared from the obtained vinyl chloride-based resin composition and subjected to a tensile test, a cold resistance test, a heat resistance test, a light resistance test, and a fogging resistance test. The obtained results were summarized in Table 5.

Example 6

A vinyl chloride-based resin composition was prepared in the same manner as in Example 1 except that the blending amount of the epoxy 1 was reduced to 10 parts, and 40 parts of tri-2-ethylhexyl trimellitate (TOTM) was used. A vinyl chloride sheet was prepared from the obtained vinyl chloride-based resin composition and subjected to a tensile test, a cold resistance test, a heat resistance test, a light resistance test, and a fogging resistance test. The obtained results were summarized in Table 5.

Comparative Example 1

A vinyl chloride-based resin composition outside the scope of the present invention was prepared in the same manner as in Example 1 except that the epoxy 4 was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Comparative Example 2

A vinyl chloride-based resin composition outside the scope of the present invention was prepared in the same manner as in Example 1 except that the epoxy 5 was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Comparative Example 3

A vinyl chloride-based resin composition outside the scope of the present invention was prepared in the same manner as in Example 1 except that the epoxy 6 was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Comparative Example 4

A vinyl chloride-based resin composition outside the scope of the present invention was prepared in the same manner as in Example 1 except that diisononyl 1,2-cyclohexane dicarboxylate (HEXAMOLL DINCH, manufactured by BASF) was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Comparative Example 5

A vinyl chloride-based resin composition outside the scope of the present invention was prepared in the same manner as in Example 1 except that commercially available tri-2-ethylhexyl trimellitate (TOTM) was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

Comparative Example 6

A vinyl chloride-based resin composition outside the scope of the present invention was prepared in the same manner as in Example 1 except that commercially available diisononyl phthalate (SANSO CIZER DINP, manufactured by New Japan Chemical Co., Ltd.) was used instead of the epoxy 1, and a vinyl chloride sheet was prepared from the obtained vinyl chloride-based resin composition. The vinyl chloride sheet was subjected to a tensile test, a cold resistance test, a heat resistance test, a light resistance test, and a fogging resistance test. The obtained results were summarized in Table 5.

TABLE 5

| | | | Example | | | | | |
| --- | --- | --- | --- | --- | --- | --- | --- | --- |
| Test items | | Unit | 1 | 2 | 3 | 4 | 5 | 6 |
| Epoxy compound | Kind | | Epoxy 1 | Epoxy 2 | Epoxy 3 | Epoxy 1 | Epoxy 2 | Epoxy 1 |
| | Blending amount (Parts by weight) | | 50 | 50 | 50 | 10 | 10 | 10 |

TABLE 5-continued

| | | | | | | | | |
|---|---|---|---|---|---|---|---|---|
| Tensile characteristics | 100% modulus | MPa | 9.9 | 10.5 | 10.3 | 10.3 | 10.5 | 12.6 |
| | Strength | MPa | 21.4 | 22.2 | 22.6 | 22.2 | 21.8 | 22.4 |
| | Elongation | % | 324 | 340 | 336 | 373 | 347 | 323 |
| Cold resistance | Softening temperature | °C. | −25 | −27 | −23 | −27 | −30 | −19 |
| Heat resistance (volatilization) | Volatile loss | 60 minutes % | 2.1 | 1.0 | 2.8 | 6.8 | 6.3 | 0.8 |
| | | 120 minutes % | 4.0 | 2.1 | 5.2 | 12.1 | 11.4 | 1.8 |
| Heat resistance (discoloration) | Sheet discoloration | 30 minutes | ◎ | ◎ | ◎ | ◎ | ◎ | ◎ |
| | | 60 minutes | ◎ | ◎ | ◎ | ○ | ○ | ○ |
| Fogging resistance | Visual evaluation | | ◎ | ◎ | ◎-○ | | | |
| | Haze value | % | 1 | 0 | 1 | 5 | 3 | 1 |
| Heat resistance (aging) | 100% modulus residual ratio | % | 108 | 109 | 105 | 119 | 117 | 94 |
| | Elongation residual ratio | % | 100 | 99 | 98 | 60 | 65 | 100 |
| Light resistance (discoloration) | Sheet discoloration | 200 h | 6.7 | 6.8 | 6.9 | 9.4 | 9.0 | 10.5 |

| | | | Comparative Example | | | | | |
|---|---|---|---|---|---|---|---|---|
| Test items | | Unit | 1 | 2 | 3 | 4 | 5 | 6 |
| Epoxy compound | Kind | | Epoxy 4 | Epoxy 5 | Epoxy 6 | DINCH | TOTM | DINP |
| | Blending amount (Parts by weight) | | 50 | 50 | 50 | 50 | 50 | 50 |
| Tensile characteristics | 100% modulus | MPa | 9.8 | 10.6 | 11.6 | 10.8 | 13.1 | 10.2 |
| | Strength | MPa | 22.4 | 22.1 | 23.5 | 22.1 | 24.0 | 20.1 |
| | Elongation | % | 318 | 319 | 345 | 361 | 330 | 320 |
| Cold resistance | Softening temperature | °C. | −15 | −19 | −15 | −29 | −17 | −27 |
| Heat resistance (volatilization) | Volatile loss | 60 minutes % | 7.9 | 3.4 | 2.6 | 7.7 | 0.6 | 3.9 |
| | | 120 minutes % | 13.0 | 6.0 | 4.9 | 14.0 | 1.2 | 7.5 |
| Heat resistance (discoloration) | Sheet discoloration | 30 minutes | ◎ | ◎ | ◎ | ○ | ○ | Δ |
| | | 60 minutes | ◎ | ◎ | ◎ | X | Δ | XX |
| Fogging resistance | Visual evaluation | | X | | | X | ◎ | X |
| | Haze value | % | 12 | 2 | 1 | 6 | 1 | 8 |
| Heat resistance (aging) | 100% modulus residual ratio | % | 151 | 109 | 110 | 120 | 92 | 114 |
| | Elongation residual ratio | % | 85 | 95 | 86 | 45 | 90 | 62 |
| Light resistance (discoloration) | Sheet discoloration | 200 h | 7.0 | 7.4 | 8.0 | 15.7 | 16.0 | 11.1 |

The results in Table 5 revealed that by using the 4,5-epoxycyclohexane dicarboxylic acid diester (Examples 1 to 3) of the present invention as a plasticizer, heat resistance, particularly discoloration can be greatly improved while maintaining an equivalent level of molding processability, flexibility, and cold resistance, compared with the case using DINCH (Comparative Example 5) and DINP (Comparative Example 7) which are currently widely used. Furthermore, even when compared with the trimellitic acid ester (Comparative Example 6) which is frequently used as a heat resistant plasticizer, there is no significant difference in fogging resistance, but heat resistance, particularly discoloration is greatly improved. Considering excellent molding processability, flexibility, and cold resistance, it is apparent that the sheet of the present invention is useful as an automotive interior material. From the results in Table 5, it is understood that by using the 4,5-epoxycyclohexane dicarboxylic acid diester of the present invention (Examples 1 to 3) as a plasticizer, the cold resistance and the heat resistance are greatly improved while maintaining an equivalent level of molding processability and flexibility, when compared with the case using the conventional 4,5-epoxycyclohexane dicarboxylic acid diester (Comparative Example 1). Further, from the results of Examples 4 to 6, it is found that heat resistance, particularly discoloration can be greatly improved by adding the 4,5-epoxycyclohexane dicarboxylic acid diester of the present invention to DINCH or TOTM which is currently widely used. From the above results, it is found that the vinyl chloride-based resin composition for automotive interior containing the epoxycyclohexane dicarboxylic acid diester according to the present invention is particularly useful as interior materials of automobiles for cold district specifications and overseas specifications used in more severe environments.

Fifth Embodiment of the Present Invention (1) Number of Carbon Atoms of Alkyl Group and Ratio of Linear-Chain Alkyl Group The number of carbon atoms of alkyl group and the ratio of the linear-chain alkyl group in the plasticizer used in examples and comparative examples of the present invention were determined by gas chromatography (hereinafter abbreviated as GC) of the composition in the raw material alcohol used for the production. The result was defined as the number of carbon atoms of alkyl group and the ratio of the linear-chain alkyl group in the plasticizer. The method of measuring the raw material alcohol by GC is the same as above.

(2) Evaluation of Physical Properties of Raw Material Ester and Present Diester

The ester value, acid value, iodine value, oxirane oxygen, and hue of the raw material ester and the present ester obtained in the following production examples were analyzed in the same manner as described above.

(3) Molding Processability

Approximately 0.01 g of a sample obtained by mixing 10 g of a plasticizer with 2 g of a vinyl chloride-based resin (straight, polymerization degree 1050, trade name "Zest 1000Z", manufactured by Shin Dai-Ichi Vinyl Corporation) was dropped onto a slide glass. A cover glass was covered on the slide glass, and the sample was set to an optical microscope. The temperature was raised at a rate of 5° C./min, and changes in the state of the particles of the vinyl chloride-based resin by the temperature rise due to heating were observed. The temperature at which the particles of the vinyl chloride-based resin started melting and the temperature at which the particles became transparent were defined as the gelation initiation temperature and the gelation termination temperature, respectively, and the average value of them was defined as the gelation temperature. The lower the gelation temperature, the faster the absorption rate of the plasticizer and the better the processability.

(4) Preparation of Vinyl Chloride Sheet

To 100 parts by weight of a vinyl chloride resin (straight, polymerization degree 1050, trade name "Zest 1000Z", manufactured by Shin Dai-Ichi Vinyl Corporation) were respectively added 0.3 parts by weight of calcium stearate (manufactured by Nacalai Tesque, Inc.) and 0.2 parts by weight of zinc stearate (manufactured by Nacalai Tesque, Inc.) as a stabilizer, and the mixture was stirred and mixed with a mortar mixer to obtain a vinyl chloride-based resin composition. After stirring and mixing with a mortar mixer, 50 parts by weight of the diester of the present invention was added and mixed by hand until uniform, thereby obtaining a vinyl chloride-based resin for medical use. This resin composition was melt-kneaded at 160 to 166° C. for 4 minutes using a 5×12 inches twin roll to prepare a roll sheet. Subsequently, press molding was performed at 162 to 168° C. for 10 minutes to prepare a press sheet having a thickness of about 1 mm.

[Evaluation of Physical Properties of Resin]

(5) Tensile Characteristics: The 100% modulus, the breaking strength and the breaking elongation of the press sheet were measured according to JIS K-6723 (1995). The measurement demonstrated that the smaller the 100% modulus, the more desirable the flexibility. The breaking strength and the breaking elongation are indications of the practical strength of the material. Generally, it can be said that the greater these values, the more superior the practical strength.

(6) Cold Resistance: The softening temperature (° C.) of the press sheet was measured according to JIS K-6773 (1999) using a Clash-Berg tester. The lower the softening temperature (° C.), the more superior the cold resistance. The softening temperature here refers to a low temperature limit indicating a predetermined torsional rigidity rate ($3.17 \times 10^3$ kg/cm$^2$) in the above measurement.

(7) Heat Resistance (Volatility, Discoloration): The heat resistance was determined according to evaluation of volatile loss and sheet discoloration after heating.

a) Volatile loss: The roll sheet was heated in a gear oven at 170° C. for 60 minutes and 120 minutes, and a change in the weight was measured; then, the volatile loss (%) was calculated according to the following equation. The smaller the value of volatile loss, the higher the heat resistance.

Volatile loss (%)=((Weight before test−Weight after test)/Weight before test)×100 b) Sheet discoloration: The roll sheet was heated in a gear oven at 170° C. for 30 minutes and 60 minutes; thereafter, the intensity of discoloration of each roll sheet was visually evaluated on a five-level scale.

⊙: Discoloration was not observed.
○: Slight discoloration was observed.
Δ: Discoloration was observed.
x: Strong discoloration was observed.
xx: Significant discoloration was observed.

(8) Ultraviolet Irradiation Test

Yellow index (YI) of the press sheet was measured after 200 hours of measurement conditions (irradiance 120 W/m$^2$, temperature 63° C., humidity 50%) using a xenon weather meter manufactured by Suga Test Instruments Co., Ltd.

Production Example 1

Esterification Reaction

A 2 L four-necked flask equipped with a thermometer, a decanter, a stirring blade and a reflux condenser was charged with 182.6 g of 4-cyclohexene-1,2-dicarboxylic anhydride (1.2 moles, RICACIDTH, manufactured by New Japan Chemical Co., Ltd.), 416 g (2.9 moles) of a saturated aliphatic alcohol containing 85.1% by weight of a linear-chain saturated aliphatic alcohol having 9 carbon atoms and 11.7% of a branched-chain saturated aliphatic alcohol having 9 carbon atoms (LINEVOL 9, manufactured by Shell Chemicals Co., Ltd.), and 0.24 g of tetraisopropyl titanate as an esterification catalyst, and then the esterification reaction was carried out at a reaction temperature of 200° C. The reaction was carried out until the acid value of the reaction solution became 0.5 mg KOH/g while removing the produced water out of the system by refluxing the alcohol under reduced pressure. After completion of the reaction, the unreacted alcohol was distilled out of the system under reduced pressure, and the system was neutralized, washed, and dehydrated according to a conventional method to obtain 449 g of an objective 4-cyclohexene-1,2-dicarboxylic acid diester (hereinafter referred to as "ester 1").

The ester 1 thus obtained had an ester value of 262 mg KOH/g, an acid value of 0.04 mg KOH/g, and a hue of 20.

Epoxidation Reaction

Then, 423 g (1.0 mole) of the ester 1 obtained in the above esterification reaction was charged into a 1 L four-necked flask equipped with a thermometer, a stirring blade and a cooling tube, and the temperature was raised to 60 to 70° C. After the temperature rise, 76.6 g (1.35 moles) of 60% hydrogen peroxide water, 18.3 g (0.30 moles) of 76% formic acid, and 1.47 g (0.01 moles) of 75% phosphoric acid were slowly added dropwise over a period of 2.25 hours. After completion of the dropwise addition, the above temperature was maintained for further 4 hours, and the reaction was completed by aging. After completion of the reaction, the aqueous phase was removed to the outside of the system, followed by washing with water and dehydration in a conventional manner to obtain 397 g of an objective 4,5-epoxycyclohexane dicarboxylic acid diester (hereinafter referred to as "epoxy 1").

The epoxy 1 thus obtained had an ester value of 256 mg KOH/g, an acid value of 0.06 mg KOH/g, an iodine value of 1.7 g $I_2$/100 g, an oxirane oxygen content of 3.5%, and a hue of 10.

Production Example 2

In the same manner as in Production Example 1 except that 464 g (2.9 moles) of saturated aliphatic alcohols having 9 to 11 carbon atoms (NEODOL 911, manufactured by Shell Chemicals Co., Ltd.) wherein the ratio of 9 carbon atoms/10 carbon atoms/11 carbon atoms is 19:43:38 and the overall linear chain ratio was 84% was added instead of 416 g of the saturated aliphatic alcohol (LINEVOL 9, manufactured by Shell Chemicals Co., Ltd.), 404 g of a 4,5-epoxycyclohexane dicarboxylic acid diester (hereinafter referred to as "epoxy 2") was obtained.

The epoxy 2 thus obtained had an ester value of 242 mg KOH/g, an acid value of 0.04 mg KOH/g, an iodine value of 1.7 g $I_2$/100 g, an oxirane oxygen content of 3.1%, and a hue of 10.

Production Example 3

In the same manner as in Production Example 1 except that 251 g (1.7 moles) of n-nonyl alcohol and 167 g (1.2 moles) of isononyl alcohol were added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 3") was obtained.

The epoxy 3 thus obtained had an ester value of 250 mg KOH/g, an acid value of 0.02 mg KOH/g, an iodine value of 1.9 g $I_2$/100 g, an oxirane oxygen content of 3.3%, and a hue of 10.

Production Example 4

In the same manner as in Production Example 1 except that 378 g (2.9 moles) of 2-ethylhexanol was added instead of 416 g of the saturated aliphatic alcohol (LINEVOL 9, manufactured by Shell Chemicals Co., Ltd.), 390 g of 4,5-epoxycyclohexane dicarboxylic acid diester (hereinafter referred to as "epoxy 4") was obtained.

The epoxy 4 thus obtained had an ester value of 273 mg KOH/g, an acid value of 0.04 mg KOH/g, an iodine value of 2.6 g $I_2$/100 g, an oxirane oxygen content of 3.7%, and a hue of 10.

Production Example 5

In the same manner as in Production Example 1 except that 167 g (1.2 moles) of n-nonyl alcohol and 251 g (1.7 moles) of isononyl alcohol were added instead of 416 g of the saturated aliphatic alcohol (LINEVOL 9, manufactured by Shell Chemicals Co., Ltd.), 340 g of 4,5-epoxycyclohexane dicarboxylic acid diester (hereinafter referred to as "epoxy 5") was obtained.

The epoxy 5 thus obtained had an ester value of 257 mg KOH/g, an acid value of 0.06 mg KOH/g, an iodine value of 2.5 g $I_2$/100 g, an oxirane oxygen content of 3.3%, and a hue of 10.

Example 1

According to the method described in "(3) Molding Processability" above, the molding processability (gelation temperature) was measured using the epoxycyclohexane dicarboxylic acid diester (epoxy 1) obtained in Production Example 1. The obtained results were shown in Table 6.

Subsequently, as described in "(4) Preparation of Vinyl Chloride Sheet", the epoxy 1 was used as a plasticizer to prepare a soft vinyl chloride-based resin composition for medical (namely, medical vinyl chloride-based resin composition for use in soft materials), and a vinyl chloride sheet was prepared from the obtained soft vinyl chloride-based resin composition. The obtained sheet was subjected to a tensile test, a cold resistance test, a heat resistance test, and an ultraviolet irradiation test. The obtained results were shown in Table 6.

Example 2

In the same manner as in Example 1 except that the epoxy 2 was used instead of the epoxy 1, the molding processability was measured, and then a soft vinyl chloride-based resin composition for medical was prepared. From the obtained soft vinyl chloride-based resin composition, a vinyl chloride sheet was prepared and subjected to a tensile test, a cold resistance test, a heat resistance test, and an ultraviolet irradiation test. The obtained results were summarized in Table 6.

Example 3

In the same manner as in Example 1 except that the epoxy 3 was used instead of the epoxy 1, the molding processability was measured, and then a soft vinyl chloride-based resin composition for medical was prepared. From the obtained soft vinyl chloride-based resin composition, a vinyl chloride sheet was prepared and subjected to a tensile test, a cold resistance test, a heat resistance test, and an ultraviolet irradiation test. The obtained results were summarized in Table 6.

Comparative Example 1

In the same manner as in Example 1 except that the epoxy 4 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, a heat resistance test, and an ultraviolet irradiation test. The obtained results were summarized in Table 6.

Comparative Example 2

In the same manner as in Example 1 except that the epoxy 5 was used instead of the epoxy 1, the molding processability was measured, and then a soft vinyl chloride-based resin composition was prepared. From the obtained soft vinyl chloride-based resin composition, a vinyl chloride sheet was prepared and subjected to a tensile test, a cold resistance test, a heat resistance test, and an ultraviolet irradiation test. The obtained results were summarized in Table 6.

Comparative Example 3

In the same manner as in Example 1 except that diisononyl 1,2-cyclohexane dicarboxylate (HEXAMOLL DINCH, manufactured by BASF) was used instead of the epoxy 1, the molding processability was measured, and then a soft vinyl chloride-based resin composition was prepared.

From the obtained soft vinyl chloride-based resin composition, a vinyl chloride sheet was prepared and subjected to a tensile test, a cold resistance test, a heat resistance test, and an ultraviolet irradiation test. The obtained results were summarized in Table 6.

Comparative Example 4

In the same manner as in Example 1 except that di-2-ethylhexyl phthalate (SANSO CIZER DOP, manufactured by New Japan Chemical Co., Ltd.) was used instead of the epoxy 1, the molding processability was measured, and then a vinyl chloride-based resin composition for soft materials was prepared. From the obtained vinyl chloride-based resin composition for soft materials, a vinyl chloride sheet was prepared and subjected to a tensile test, a cold resistance test, a heat resistance test, and an ultraviolet irradiation test. The obtained results were summarized in Table 6.

Comparative Example 5

In the same manner as in Example 1 except that commercially available tri-2-ethylhexyl trimellitate was used instead of the epoxy 1, the molding processability was measured, and then a vinyl chloride-based resin composition for soft materials was prepared. From the obtained vinyl chloride-based resin composition for soft materials, a vinyl chloride sheet was prepared and subjected to a tensile test, a cold resistance test, a heat resistance test, and an ultraviolet irradiation test. The obtained results were summarized in Table 6.

only ultraviolet irradiation but also in sterilization or disinfection treatment by various radiation irradiation which is thought to cause discoloration with the same mechanism.

In addition, in comparison with the resin composition (Comparative Example 4) blended with a phthalate ester type plasticizer which is currently most widely used, the medical vinyl chloride-based resin compositions (Examples 1 to 3) also containing the epoxycyclohexane dicarboxylic acid diester of the present invention has less volatile loss and no discoloration by heat, and has reduced concerns regarding deterioration of flexibility due to volatilization of the plasticizer as well as degradation such as discoloration at the time of sterilization or disinfection treatment accompanied by heating such as boiling or heating in autoclave. Thus, these properties are found to be extremely useful.

Next, even when compared with the resin composition (Comparative Example 5) in which TOTM, namely a trimellitate ester type plasticizer that is beginning to be used recently as an excellent heat resistant one, is blended, it is understood that the discoloration of the vinyl chloride-based resin composition containing the epoxycyclohexane dicarboxylic acid diester after the UV irradiation test is very small.

In addition, by using the epoxycyclohexane dicarboxylic acid diester according to the present invention, the flexibility and cold resistance at the time of use are equal to or higher than the resin composition (Comparative Examples 1 and 2) blended with the epoxycyclohexane dicarboxylic acid diester outside the scope of the present invention. Furthermore, it is revealed that the composition of the invention is

TABLE 6

| | | | Example | | | Comparative Example | | | | |
|---|---|---|---|---|---|---|---|---|---|---|
| Test items | | Unit (Condition) | 1 | 2 | 3 | 1 | 2 | 3 | 4 | 5 |
| Plasticizer | | Kind | Epoxy 1 | Epoxy 2 | Epoxy 3 | Epoxy 4 | Epoxy 5 | DINCH | DOP | TOTM |
| | | Ratio of linear-chain alkyl group (%) | 87 | 83 | 60 | 0 | 40 | 10 | 0 | 0 |
| Molding processability | Gelation temperature | ° C. | 118 | 122 | 118 | 105 | 118 | 136 | 112 | 135 |
| Tensile characteristics | 100% modulus | MPa | 9.9 | 10.5 | 10.3 | 9.8 | 10.6 | 10.8 | 9.4 | 13.1 |
| | Strength | MPa | 21.4 | 22.2 | 22.6 | 22.4 | 22.7 | 22.1 | 21.4 | 24.0 |
| | Elongation | % | 324 | 340 | 336 | 318 | 337 | 361 | 320 | 330 |
| Cold resistance | Softening temperature | ° C. | −25 | −27 | −23 | −15 | −22 | −29 | −24 | −17 |
| Heat resistance | Volatile loss | % (170° C., 60 min.) | 2.2 | 0.9 | 2.4 | 7.9 | 2.8 | 7.9 | 8.8 | 0.6 |
| | | % (170° C., 120 mm.) | 4.2 | 2.1 | 4.7 | 13.0 | 5.3 | 13.8 | 15.1 | 1.2 |
| | Sheet discoloration | (170° C., 30 min.) | ◎ | ◎ | ◎ | ◎ | ◎ | Δ | Δ | ○ |
| | | (170° C., 60 min.) | ◎ | ◎ | ◎ | ◎ | ◯ | XX | XX | X |
| UV irradiation test | Sheet discoloration | (200 hours) | 6.7 | 6.8 | 6.9 | 7.0 | 6.9 | 10.8 | 10.9 | 15.7 |

The results of Table 6 clearly revealed that the vinyl chloride-based resin compositions for medical (Examples 1 to 3) in which the epoxycyclohexane dicarboxylic acid diester of the present invention was blended showed very small discoloration after the ultraviolet irradiation test as compared with the resin composition (Comparative Example 4) in which DOP was blended as a phthalic acid ester-type plasticizer that was currently most commonly used. Generally, discoloration of a molded body obtained from the vinyl chloride resin composition is due to formation of conjugated polyene by dehydrochlorination reaction of the vinyl chloride resin. Thus, irradiation with ultraviolet rays or radiation promotes such discoloration, so that it is known that discoloration occurs during sterilization or disinfection treatment. From the above results, it can be said that the same effect on discoloration may be exerted in not only ultraviolet irradiation but also in sterilization or disinfection treatment by various radiation irradiation which is thought to cause discoloration with the same mechanism.

very useful because it has less volatile loss as well as has reduced concerns regarding deterioration of flexibility due to volatilization of the plasticizer at the time of sterilization or disinfection treatment accompanied by heating such as boiling or autoclave heating.

INDUSTRIAL APPLICABILITY

The novel epoxycyclohexane dicarboxylic acid diester having an epoxy group in the molecular structure according to the present invention is excellent in plasticizing performance inherent in plasticizer for thermoplastic resin and rubber, is also excellent in heat resistance and cold resistance, and is therefore an excellent plasticizer capable of coping with demands for cold resistance and heat resistance which becomes increasingly severer in recent years, or is very useful as a stabilizer in a chlorine-containing resin. In particular, the epoxycyclohexane dicarboxylic acid diester of the present invention can be used as a plasticizer having also properties as a stabilizer in a chlorine-containing resin typified by vinyl chloride, and also can be used as a stabilizer in various material systems such as hard materials, semi-hard materials, and soft materials blended with other plasticizers. The resin composition blended with the epoxycyclohexane dicarboxylic acid diester having such performances and the resin molded body can be used in applications for electric wire covering and automobile parts, pipes such as water pipes, fittings for pipes, gutters such as rain gutters, window frame siding materials, flat plate, corrugated sheet, general film sheet applications (laminate, packaging, vehicle, miscellaneous goods, etc.), agricultural film applications, leather applications, compound applications, floor material applications, wallpaper applications, footwear applications, sealing material applications, fiber applications, hose applications, gasket applications, building material applications, paint applications, adhesive applications, paste applications, medical applications, and the like.

The invention claimed is:

1. An epoxycyclohexane dicarboxylic acid diester comprising a 4,5-epoxycyclohexane-1,2-dicarboxylic acid diester represented by the following general formula (1), wherein the molar ratio of the linear-chain alkyl group with respect to the total amount of the alkyl groups constituting the dicarboxylic acid diester is 50 to 99%:

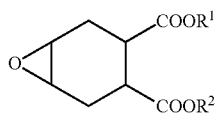

(1)

wherein R1 and R2 are the same or different and each represents a linear or branched-chain alkyl group having 7 to 13 carbon atoms,
wherein the molar ratio of cis isomer to trans isomer of the oxirane ring and the alkyloxycarbonyl group via the cyclohexane ring measured by proton nuclear magnetic resonance spectroscopy is 5/95 to 35/65.

2. The epoxycyclohexane dicarboxylic acid diester according to claim 1, wherein (i) the alkyl group is composed of 90% or more of an alkyl group having 9 to 11 carbon atoms, in which the molar ratio of alkyl group having 9 carbon atoms/alkyl group having 10 carbon atoms/alkyl group having 11 carbon atoms is in the range of 10 to 25/35 to 50/30 to 45, or (ii) the alkyl group contains an alkyl group having 9 carbon atoms in an amount of 90% or more molar ratio with respect to the total amount of the alkyl groups constituting the dicarboxylic acid diester.

3. The epoxycyclohexane dicarboxylic acid diester according to claim 1, wherein the molar ratio of the linear-chain alkyl group in the alkyl groups is 55 to 95%.

4. A plasticizer for vinyl chloride-based resins, comprising the epoxycyclohexane dicarboxylic acid diester according to claim 1.

5. A vinyl chloride-based resin composition comprising a vinyl chloride-based resin and the plasticizer for vinyl chloride-based resins according to claim 4.

6. The vinyl chloride-based resin composition according to claim 5, wherein the content of the plasticizer for vinyl chloride-based resins is 1 to 200 parts by weight with respect to 100 parts by weight of the vinyl chloride-based resin.

7. A vinyl chloride-based molded body obtained from the vinyl chloride-based resin composition according to claim 5.

8. A stabilizer for chlorine-containing resins, comprising the epoxycyclohexane dicarboxylic acid diester according to claim 1.

9. A chlorine-containing resin composition comprising a chlorine-containing resin and the stabilizer according to claim 8.

10. The chlorine-containing resin composition according to claim 9, wherein the content of the stabilizer is 1 to 30 parts by weight with respect to 100 parts by weight of the chlorine-containing resin.

11. The chlorine-containing resin composition according to claim 9, further comprising a plasticizer.

12. A chlorine-containing resin molded body obtained from the chlorine-containing resin composition according to claim 9.

13. A vinyl chloride-based resin composition for automotive interior, comprising a vinyl chloride-based resin and the epoxycyclohexane dicarboxylic acid diester according to claim 1.

14. An automotive interior material comprising the vinyl chloride-based resin composition for automotive interior according to claim 13.

15. A medical vinyl chloride-based resin composition comprising a vinyl chloride-based resin and the epoxycyclohexane dicarboxylic acid diester according to claim 1.

16. The medical vinyl chloride-based resin composition according to claim 15, further comprising a fatty acid calcium salt and/or a fatty acid zinc salt.

17. The medical vinyl chloride-based resin composition according to claim 15, further comprising a silane compound.

18. A medical material comprising the medical vinyl chloride-based resin composition according to claim 15.

19. A method for stabilizing a chlorine-containing resin by containing an epoxycyclohexane dicarboxylic acid diester comprising a 4,5-epoxycyclohexane-1,2-dicarboxylic acid diester represented by the following general formula (1), wherein the molar ratio of the linear-chain alkyl group with respect to the total amount of the alkyl groups constituting the dicarboxylic acid diester is 50 to 99%:

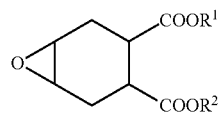

(1)

wherein R1 and R2 are the same or different and each represents a linear or branched-chain alkyl group having 7 to 13 carbon atoms,
wherein the molar ratio of cis isomer to trans isomer of the oxirane ring and the alkyloxycarbonyl group via the cyclohexane ring measured by proton nuclear magnetic resonance spectroscopy is 5/95 to 35/65.

* * * * *

UNITED STATES PATENT AND TRADEMARK OFFICE
CERTIFICATE OF CORRECTION

PATENT NO. : 10,836,739 B2
APPLICATION NO. : 15/576651
DATED : November 17, 2020
INVENTOR(S) : Takahiro Inoue Page 1 of 2

It is certified that error appears in the above-identified patent and that said Letters Patent is hereby corrected as shown below:

On the Title Page

Column 1, Item (73), Line 2, delete "LTD," and insert --LTD.,--.

Column 2, Item (56), Line 3, delete "vol. 1 No. 1," and insert --vol. 1, No. 1,--.

Column 2, Item (56), Line 8, delete "JP2016 065456." and insert --JP2016/065456.--.

In the Specification

Column 5, Line 38, delete "asunder" and insert --as under--.

Column 10, Line 22, delete "anyone" and insert --any one--.

Column 14, Line 5, delete "anyone" and insert --any one--.

Column 16, Line 45, delete "anyone" and insert --any one--.

Column 16, Line 58, delete "[item. 13]," and insert --[item 13],--.

Column 21, Line 49, delete "transform)" and insert --trans form)--.

Column 29, Line 22, delete "(e.g." and insert --e.g.--.

Column 31, Line 22, delete "poly[{" and insert --poly--.

Column 31, Line 24, delete "imino)" and insert --imino--.

Column 31, Line 26, delete "(2" and insert --2--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,836,739 B2

Column 34, Line 27, delete "trinellitate" and insert --trimellitate--.

Column 40, Line 18, delete "α" and insert --γ--.

Column 44, Line 11, delete "times" and insert --times.--.

Column 44, Line 17, delete "$cm^{-1}$" and insert --$cm^{-1}$.--.

Column 50, Line 22, delete "RICACIDTH," and insert --RICACID TH,--.

Column 56, Line 42, delete "RICACIDTH," and insert --RICACID TH,--.

Column 62, Line 11, delete "○θA" and insert --○Δ--.

Column 62, Line 62, delete "RICACIDTH," and insert --RICACID TH,--.

Column 70, Line 34, delete "RICACIDTH," and insert --RICACID TH,--.

Column 73, Line 46, delete "mm.)" and insert --min.)--.